United States Patent
Heil et al.

(10) Patent No.: US 9,609,868 B2
(45) Date of Patent: Apr. 4, 2017

(54) ALKOXIMINO-SUBSTITUTED ANTHRANILIC ACID DIAMIDES AS PESTICIDES

(71) Applicant: BAYER CROPSCIENCE AKTIENGESELLSCHAFT, Monheim (DE)

(72) Inventors: Markus Heil, Leichlingen (DE); Ruediger Fischer, Pulheim (DE); Susanne Kuebbeler, Duesseldorf (DE); Kerstin Ilg, Cologne (DE); Arnd Voerste, Cologne (DE); Ulrich Goergens, Ratingen (DE)

(73) Assignee: BAYER CROPSCIENCE AG, Monheim (DE)

( * ) Notice: Subject to any disclaimer, the term of this patent is extended or adjusted under 35 U.S.C. 154(b) by 8 days.

(21) Appl. No.: 14/770,097

(22) PCT Filed: Mar. 5, 2014

(86) PCT No.: PCT/EP2014/054268
§ 371 (c)(1),
(2) Date: Aug. 25, 2015

(87) PCT Pub. No.: WO2014/135588
PCT Pub. Date: Sep. 12, 2014

(65) Prior Publication Data
US 2016/0007603 A1    Jan. 14, 2016

(30) Foreign Application Priority Data

Mar. 6, 2013   (EP) .................................. 13157989

(51) Int. Cl.
| | | |
|---|---|---|
| A01N 43/56 | (2006.01) |
| A01N 43/713 | (2006.01) |
| C07D 401/14 | (2006.01) |
| C07D 401/04 | (2006.01) |
| C07D 405/14 | (2006.01) |
| C07D 409/14 | (2006.01) |

(52) U.S. Cl.
CPC ........... *A01N 43/56* (2013.01); *A01N 43/713* (2013.01); *C07D 401/04* (2013.01); *C07D 401/14* (2013.01); *C07D 405/14* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 7,541,377 B2 * | 6/2009 | Finkelstein ............ | A01N 43/56 514/406 |
| 8,143,292 B2 | 3/2012 | Schmidt et al. | |
| 8,324,390 B2 | 12/2012 | Fischer et al. | |
| 8,338,419 B2 | 12/2012 | Schmidt et al. | |
| 8,536,202 B2 | 9/2013 | Fischer et al. | |
| 8,772,289 B2 | 7/2014 | Schmidt et al. | |
| 8,791,139 B2 | 7/2014 | Fischer et al. | |
| 8,791,143 B2 | 7/2014 | Fischer et al. | |
| 8,980,886 B2 | 3/2015 | Fischer et al. | |
| 9,044,016 B2 | 6/2015 | Kaiser et al. | |
| 9,056,853 B2 | 6/2015 | Schmidt et al. | |
| 2012/0010250 A1 | 1/2012 | Fischer et al. | |
| 2014/0162875 A1 | 6/2014 | Deshmukh et al. | |
| 2014/0171316 A1 | 6/2014 | Deshmukh et al. | |
| 2014/0179519 A1 | 6/2014 | Kaiser et al. | |
| 2014/0200134 A1 | 7/2014 | Kaiser et al. | |
| 2014/0200135 A1 | 7/2014 | Kaiser et al. | |
| 2014/0243195 A1 | 8/2014 | Kordes et al. | |
| 2014/0243196 A1 | 8/2014 | Deshmukh et al. | |
| 2014/0243197 A1 | 8/2014 | Deshmukh et al. | |

FOREIGN PATENT DOCUMENTS

| | | |
|---|---|---|
| WO | 0170671 A2 | 9/2001 |
| WO | 03015518 A1 | 2/2003 |
| WO | 03015519 A1 | 2/2003 |
| WO | 03016282 A2 | 2/2003 |
| WO | 03016283 A1 | 2/2003 |
| WO | 03016284 A1 | 2/2003 |
| WO | 03024222 A1 | 3/2003 |
| WO | 03027099 A1 | 4/2003 |
| WO | 03062226 A1 | 7/2003 |

(Continued)

OTHER PUBLICATIONS

International Search Report from corresponding PCT/EP2014/054268, mailed Apr. 22, 2014.

*Primary Examiner* — Kamal Saeed
(74) *Attorney, Agent, or Firm* — McBee Moore Woodward Vanik IP LLC

(57) ABSTRACT

The present invention relates to novel anthranilic acid diamide derivatives of the general formula (I)

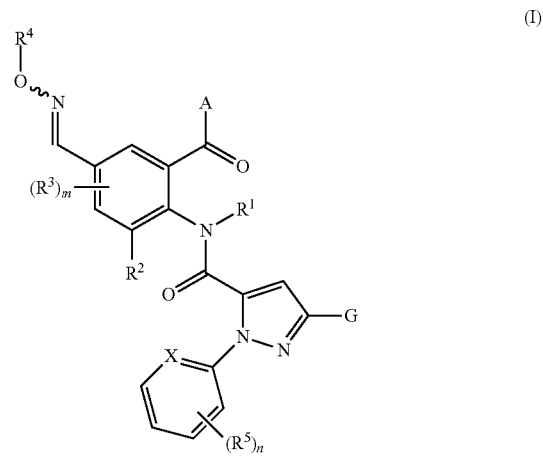

(I)

—in which $R^1$, $R^2$, $R^3$, $R^4$, $R^5$, A, G, X, m and n are as defined in the description—, to their use as insecticides and acaricides for controlling of animal pests, and to a plurality of processes for their preparation.

11 Claims, No Drawings

(56) References Cited

FOREIGN PATENT DOCUMENTS

| | | |
|---|---|---|
| WO | 2004027042 A2 | 4/2004 |
| WO | 2004033468 A1 | 4/2004 |
| WO | 2004046129 A2 | 6/2004 |
| WO | 2004067528 A1 | 8/2004 |
| WO | 2005077934 A1 | 8/2005 |
| WO | 2005085234 A2 | 9/2005 |
| WO | 2005118552 A2 | 12/2005 |
| WO | 2006000336 A2 | 1/2006 |
| WO | 2006023783 A1 | 3/2006 |
| WO | 2006040113 A2 | 4/2006 |
| WO | 2006111341 A1 | 10/2006 |
| WO | 2007006670 A1 | 1/2007 |
| WO | 2007020877 A1 | 2/2007 |
| WO | 2007024833 A1 | 3/2007 |
| WO | 2007043677 A1 | 4/2007 |
| WO | 2007080131 A2 | 7/2007 |
| WO | 2007093402 A1 | 8/2007 |
| WO | 2007144100 A1 | 12/2007 |
| WO | 2008126889 A1 | 10/2008 |
| WO | 2008126890 A1 | 10/2008 |
| WO | 2008126933 A2 | 10/2008 |
| WO | 2010069502 A2 | 6/2010 |
| WO | 2011128329 A1 | 10/2011 |
| WO | 2011157651 A1 | 12/2011 |
| WO | 2011157653 A1 | 12/2011 |
| WO | 2011157654 A1 | 12/2011 |
| WO | 2012004208 A1 | 1/2012 |
| WO | 2013024003 A1 | 2/2013 |
| WO | 2013024004 A1 | 2/2013 |
| WO | 2013024005 A1 | 2/2013 |
| WO | 2013024006 A1 | 2/2013 |
| WO | 2013024009 A1 | 2/2013 |
| WO | 2013024010 A1 | 2/2013 |
| WO | 2013024169 A1 | 2/2013 |
| WO | 2013024170 A1 | 2/2013 |
| WO | 2013024171 A1 | 2/2013 |

* cited by examiner

ALKOXIMINO-SUBSTITUTED ANTHRANILIC ACID DIAMIDES AS PESTICIDES

CROSS REFERENCE TO RELATED APPLICATIONS

This application is a §371 National Stage Application of PCT/EP2014/054268, filed 5 Mar. 2014, which claims priority to EP 13157989.8, filed 6 Mar. 2013.

BACKGROUND

Field of the Invention

The present invention relates to novel anthranilic acid diamide derivatives, to the use thereof as insecticides and acaricides for control of animal pests, and to several processes for preparation thereof.

Description of Related Art

Anthranilic acid derivatives having insecticidal properties have already been described in the literature, for example in WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO2007/020877, WO 2007/144100, WO2007/043677, WO2007/080131, WO2007/093402, WO2008/126889, WO2008/126890, WO2008/126933, WO2011/157653, WO2011/157654, WO2011/157651, WO2012/004208, WO 2010/069502, WO 2011/128329, WO 2013/024003, WO 2013/024004, WO 2013/024005, WO 2013/024006, WO 2013/024009, WO 2013/024010, WO 2013/024169, WO 2013/024170 and WO 2013/024171.

However, the active compounds already known according to the documents cited above have some disadvantages on application, whether because they exhibit only a narrow range of application or because they do not have satisfactory insecticidal or acaricidal activity.

SUMMARY

Novel anthranilic acid derivatives have now been found, which have advantages over the compounds already known, examples being better biological or environmental properties, a wider range of application methods, a better insecticidal or acaricidal activity, and also good compatibility with crop plants. The anthranilic acid derivatives can be used in combination with further agents for enhancing efficacy, particularly towards insects which are difficult to control.

The present invention therefore provides novel anthranilamides of the formula (I)

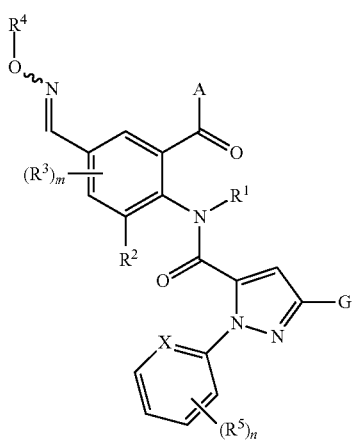

(I)

in which if

A represents $N(R^6)R^7$,

G represents fluoromethyl, difluoromethyl, chlorodifluoromethyl, $C_2$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, fluoromethoxy, fluoroethoxy, difluoroethoxy, tetrafluoroethoxy, chlorodifluoroethoxy, dichlorofluoroethoxy, $C_3$-$C_6$-haloalkoxy, $C_1$-$C_6$-haloalkoxy-$C_1$-$C_4$-alkyl, $C_2$-$C_4$-haloalkylthio, $C_2$-$C_4$-haloalkylsulfinyl, $C_2$-$C_4$-haloalkylsulfonyl or represents —W-Q, if A represents $N(R^8)$—$N(R^9)(R^{10})$, G represents $C_1$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, $C_1$-$C_6$-haloalkoxy, $C_1$-$C_6$-haloalkoxy-$C_1$-$C_4$-alkyl, $C_1$-$C_4$-haloalkylthio, $C_1$-$C_4$-haloalkylsulfinyl, $C_1$-$C_4$-haloalkylsulfonyl, halogen or represents —W-Q, if A represents $N(R^6)$-L, G represents $C_1$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, $C_1$-$C_6$-haloalkoxy, $C_1$-$C_6$-haloalkoxy-$C_1$-$C_4$-alkyl, $C_1$-$C_4$-haloalkylthio, $C_1$-$C_4$-haloalkylsulfinyl, $C_1$-$C_4$-haloalkylsulfonyl, halogen or represents —W-Q, $R^1$ represents hydrogen or represents $C_1$-$C_6$-alkyl, $C_2$-$C_6$-alkenyl, $C_2$-$C_6$-alkynyl or $C_3$-$C_6$-cycloalkyl, each of which is optionally mono- or polysubstituted by identical or different substituents, where the substituents may be selected independently of one another from the group consisting of halogen, cyano, nitro, hydroxy, $C_1$-$C_4$-alkoxy, $C_1$-$C_4$-alkylthio, $C_1$-$C_4$-alkylsulfinyl, $C_1$-$C_4$-alkylsulfonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl)-$C_3$-$C_6$-cycloalkylamino, $R^2$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, halogen, cyano, nitro or $C_3$-$C_6$-trialkylsilyl, $R^3$ independently of one another represent hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 2, $R^4$ represents $C_1$-$C_6$-alkyl, $C_3$-$C_6$-cycloalkyl, $C_2$-$C_6$-alkenyl, $C_2$-$C_6$-alkynyl, $C_1$-$C_6$-alkylsulfonyl, $C_1$-$C_4$-alkoxycarbonyl, $C_1$-$C_6$-alkylcarbonyl, aminocarbonyl, $C_1$-$C_6$-alkylaminocarbonyl or $C_1$-$C_6$-dialkylaminocarbonyl, each of which is optionally mono- or polysubstituted by identical or different substituents, where the substituents may be selected independently of one another from the group consisting of halogen, cyano, nitro, hydroxy, $C_1$-$C_6$ alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, $C_1$-$C_4$-alkoxycarbonyl, $R^5$ independently of one another represent hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, n represents 0 to 4, X represents N, CH, CF, CCl, CBr or CI, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_2$-$C_6$-alkoxycarbonyl or $C_2$-$C_6$-alkylcarbonyl, $R^7$ represents hydrogen or represents $C_1$-$C_6$-alkyl, $C_2$-$C_6$-alkenyl, $C_2$-$C_6$-alkynyl, each of which is optionally mono- or polysubstituted by identical or different substituents, where the substituents may be selected independently of one another from the group consisting of halogen, cyano, nitro, hydroxy, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl and $C_3$-$C_6$-trialkylsilyl, $R^7$ also furthermore represents optionally substituted aryl-$C_1$-$C_4$-alkyl, heteroaryl-$C_1$-$C_4$-alkyl, $C_3$-$C_{12}$-cycloalkyl, $C_3$-$C_{12}$-cycloalkyl-$C_1$-$C_6$-alkyl and $C_4$-$C_{12}$-bicycloalkyl, where the substituents may be selected independently of one another from the group consisting of halogen, cyano, nitro, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, $C_2$-$C_6$-alkylcarbonyl, $R^7$ furthermore represents a 5- or 6-membered aromatic or heteroaromatic ring, a 5- or 6-membered partially saturated ring or saturated heterocyclic ring, or a saturated or aromatic heterobicyclic ring which is mono- or polysubstituted by identical or different substituents and which may optionally contain one to three heteroatoms from the group consisting of O, S and N, where the substituents independently of one another may be selected from the group consisting of halogen, cyano, nitro, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl and $C_2$-$C_6$-alkylcarbonyl, $R^6$ and $R^7$ may be linked to one another via two to six carbon atoms and form a ring which optionally additionally contains a further nitrogen, sulfur or oxygen atom and may optionally be mono- to tetrasubstituted by $C_1$-$C_2$-alkyl, halogen, cyano, amino or $C_1$-$C_2$-alkoxy, $R^8$, $R^9$ independently of one another represent hydrogen, $C_2$-$C_6$-alkoxycarbonyl, $C_2$-$C_6$-alkylcarbonyl, $C_2$-$C_6$-alkylaminocarbonyl, $C_2$-$C_6$-dialkylaminocarbonyl, $C_2$-$C_6$-alkylsulfonyl, or represent $C_1$-$C_6$-alkyl, $C_1$-$C_6$-alkoxy, $C_2$-$C_6$-alkenyl, $C_3$-$C_6$-alkynyl, $C_3$-$C_6$-cycloalkyl, each of which may be mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, $C_2$-$C_6$-alkylcarbonyl and $C_3$-$C_6$-trialkylsilyl, or $R^8$, $R^9$ independently of one another represent a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)$NH_2$, $NO_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or $R^8$ and $R^9$ may be linked to one another via two to six carbon atoms and form a ring which optionally additionally contains a further nitrogen, sulfur or oxygen atom and may optionally be mono- to tetrasubstituted by $C_1$-$C_2$-alkyl, $C_1$-$C_2$-haloalkyl, halogen, cyano, amino, $C_1$-$C_2$-alkoxy or $C_1$-$C_2$-haloalkoxy, $R^{10}$ represents a group selected from the group consisting of —C(=S)—$R^{11}$, —C(=O)—$R^{11}$, —C(=O)—$OR^{12}$, —C(=S)—$OR^{12}$, —C(=O)—$SR^{13}$, —C(=S)—$SR^{13}$, —C(=O)—$NR^{14}R^{15}$, —C(=S)—$NR^{14}R^{15}$, —S(O)$_2$—$R^{16}$ and —S(O)$_2$—$NR^{17}R^{18}$, $R^{11}$, $R^{12}$, $R^{13}$, $R^{16}$ independently of one another represent $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or aryl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^{14}$, $R^{15}$, $R^{17}$, $R^{18}$ independently of one another represent hydrogen or represent $R^{11}$, L represents

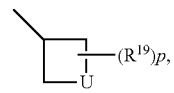

U represents O, S, SO, $SO_2$, S(O)=N—$R^{20}$, N—$R^{21}$, C=O, C=N—O—$R^{22}$, $R^{19}$ independently of one another represent hydrogen, $C_1$-$C_6$-alkyl, $C_1$-$C_6$-haloalkyl, $C_2$-$C_6$-alkenyl, $C_2$-$C_6$-alkynyl, halogen, cyano, nitro, hydroxy, COOH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl or $C_1$-$C_4$-haloalkylsulfonyl, $R^{20}$, $R^{21}$, $R^{22}$ independently of one another represent $C_1$-$C_6$-alkyl, P represents 0, 1, 2, 3, W represents a radical from the group consisting of —$CH_2$—, —$CH_2O$—, —$OCH_2$—, —$CH_2OCH_2$—, —$CH_2S$—, —$CH_2SCH_2$—, —CH(CN)—, —CH(F)—, —CH(Cl)—, —CH($C_1$-$C_6$-alkyl)-, —C(di-$C_1$-$C_6$-alkyl)-, —$CH_2CH_2$—, Q represents a 5- or 6-membered aromatic heterocyclic ring from the group of Q-1 to Q-61 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro or $C_1$-$C_2$-haloalkoxy,

Q-1

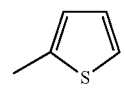

-continued
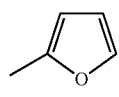 Q-2
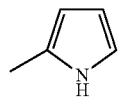 Q-3
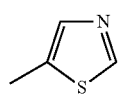 Q-4
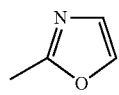 Q-5
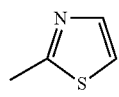 Q-6
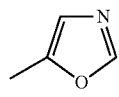 Q-7
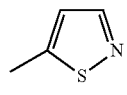 Q-8
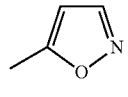 Q-9
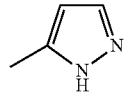 Q-10
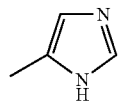 Q-11
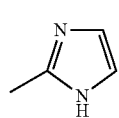 Q-12
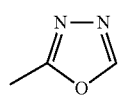 Q-13
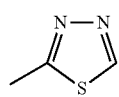 Q-14
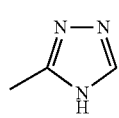 Q-15
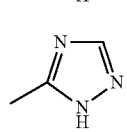 Q-16
-continued
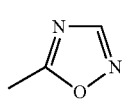 Q-17
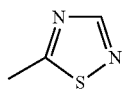 Q-18
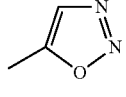 Q-19
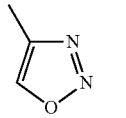 Q-20
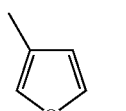 Q-21
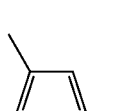 Q-22
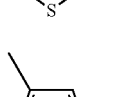 Q-23
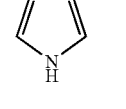 Q-24
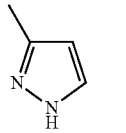 Q-25
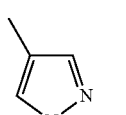 Q-26
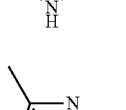 Q-27
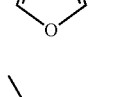 Q-28
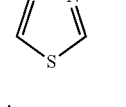
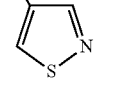

-continued
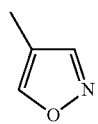
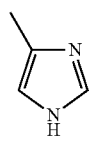
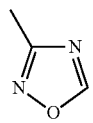
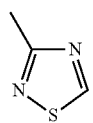
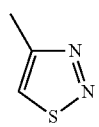
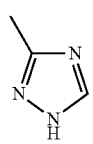
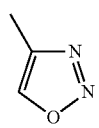
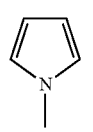
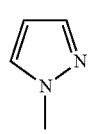
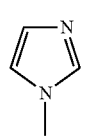
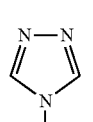
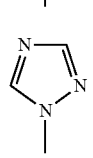
-continued
Q-29 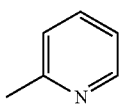
Q-30 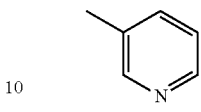
Q-31 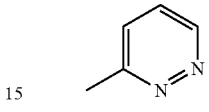
Q-32 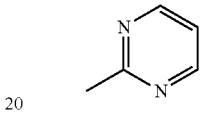
Q-33 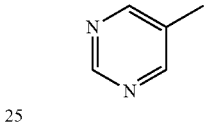
Q-34 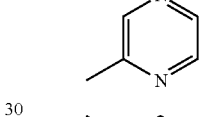
Q-35 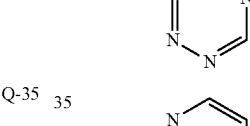
Q-36 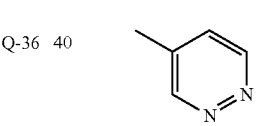
Q-37 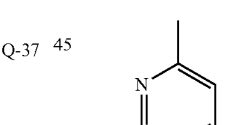
Q-38 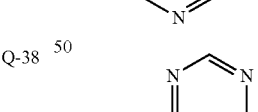
Q-39 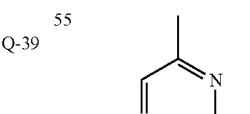
Q-40 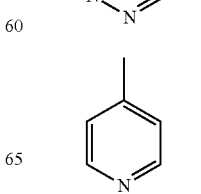
Q-41
Q-42
Q-43
Q-44
Q-45
Q-46
Q-47
Q-48
Q-49
Q-50
Q-51
Q-52
Q-53

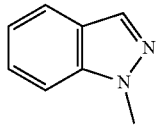
Q-54

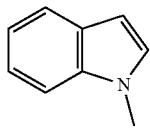
Q-55

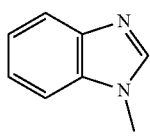
Q-56

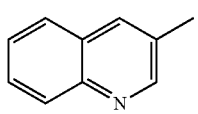
Q-57

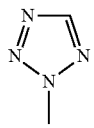
Q-58

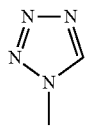
Q-59

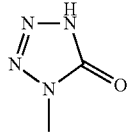
Q-60

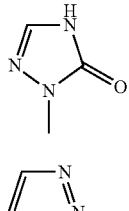
Q-61

Q-62

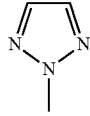
Q-63 where the compounds of the general formula (I) also include N-oxides and salts.

DETAILED DESCRIPTION OF A PREFERRED EMBODIMENT

Finally, it has been found that the compounds of the formula (I) according to the invention have very good insecticidal properties and can be used both in crop protection and in the protection of materials for control of undesirable pests such as insects.

The compounds according to the invention may optionally be present as mixtures of different possible isomeric forms, especially of stereoisomers, for example, E and Z isomers, threo and erythro isomers, and optical isomers, but if appropriate also of tautomers. Both the E and Z isomers, and the threo and erythro isomers, and also the optical isomers, any desired mixtures of these isomers, and the possible tautomeric forms are claimed.

A general definition of the anthranilamides according to the invention is provided by the formula (I). Preferred radical definitions for the formulae specified above and hereinafter are given below. These definitions apply to the end products of the formula (I) and likewise to all intermediates. Here:

if A preferably, particularly preferably or very particularly preferably represents $N(R^6)R^7$, G preferably represents fluoromethyl, difluoromethyl, chlorodifluoromethyl, $C_2$-$C_4$-haloalkyl, $C_2$-$C_4$-haloalkenyl, $C_2$-$C_4$-haloalkynyl, $C_3$-$C_4$-halocycloalkyl, $C_1$-$C_4$-alkoxy, fluoromethoxy, fluoroethoxy, difluoroethoxy, tetrafluoroethoxy, chlorodifluoroethoxy, dichlorofluoroethoxy, $C_3$-$C_4$-haloalkoxy, $C_1$-$C_4$-haloalkoxy-$C_1$-$C_4$-alkyl, $C_2$-$C_4$-haloalkylthio, $C_2$-$C_4$-haloalkylsulfinyl, $C_2$-$C_4$-haloalkylsulfonyl or represents —W-Q, G particularly preferably represents fluoromethyl, difluoromethyl, chlorodifluoromethyl, 1,1-difluoroethyl, 2,2-difluoroethyl, 1,2,2-trifluoroethyl, 1,1,2,2-tetrafluoroethyl, pentafluoroethyl, methoxy, ethoxy, n-propoxy, isopropoxy, fluoromethoxy, 2-fluoroethoxy, 2,2-difluoroethoxy, 2-chloro-2,2-difluoroethoxy, 2,2-difluoropropoxy, 3-chloro-1,1,2-trifluoropropoxy, difluoromethoxymethyl, trifluoromethoxymethyl, trifluoroethoxymethyl or represents —W-Q, G very particularly preferably represents fluoromethyl, difluoromethyl, methoxy, ethoxy, n-propoxy, isopropoxy, 2,2-difluoroethoxy, or represents —W-Q, if A preferably, particularly preferably or very particularly preferably represents $N(R^8)$—$N(R^9)(R^{10})$, if A furthermore preferably, particularly preferably or very particularly preferably represents $N(R^6)$-L, G preferably represents $C_1$-$C_4$-haloalkyl, $C_2$-$C_4$-haloalkenyl, $C_1$-$C_4$-alkoxy, $C_1$-$C_4$-haloalkoxy, $C_1$-$C_4$-haloalkoxy-$C_1$-$C_4$-alkyl, $C_1$-$C_4$-haloalkylthio, $C_1$-$C_4$-haloalkylsulfinyl, $C_1$-$C_4$-haloalkylsulfonyl, halogen or represents —W-Q, G particularly preferably represents halogen, fluoromethyl, difluoromethyl, trifluoromethyl, chlorodifluoromethyl, 1,1-difluoroethyl, 2,2-difluoroethyl, 1,2,2-trifluoroethyl, 1,1,2,2-tetrafluoroethyl, pentafluoroethyl, methoxy, ethoxy, n-propoxy, isopropoxy, fluoromethoxy, difluoromethoxy, trifluoromethoxy, fluoroethoxy, difluoroethoxy, trifluoroethoxy, 2-chloro-2,2-difluoromethoxy, 2,2-difluoropropoxy, 3-chloro-1,1,2-trifluoropropoxy, difluoromethoxymethyl, trifluoromethoxymethyl, trifluoroethoxymethyl, difluoromethylthio, trifluoromethylthio, difluoromethylsulfinyl, trifluoromethylsulfinyl, difluoromethylsulfonyl, trifluoromethylsulfonyl or represents —W-Q, G very particularly preferably represents chlorine, bromine, fluoromethyl, difluoromethyl, trifluoromethyl, methoxy, ethoxy, n-propoxy, isopropoxy, difluoromethoxy, trifluoromethoxy, 2,2-difluoroethoxy, trifluoroethoxy or represents —W-Q, R¹ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl or $C_1$-$C_4$-alkylsulfonyl-$C_1$-$C_4$-alkyl, R¹ particularly preferably represents hydrogen, methyl, cyclopropyl, cyanomethyl, methoxymethyl, methylthiomethyl, methylsulfinylmethyl or methylsulfonylmethyl, R¹ very particularly preferably represents hydrogen, R² preferably represents hydrogen, $C_1$-$C_4$-alkyl, halogen, cyano, $C_1$-$C_4$-alkoxy, R² particularly preferably represents methyl, ethyl, methoxy, ethoxy, F, Cl or Br, R² very particularly preferably represents methyl, Br, Cl, R² especially preferably represents methyl, R³ preferably represents hydrogen, $C_1$-$C_6$-alkyl, $C_1$-$C_4$-alkoxy, halogen, cyano or nitro, R³ particularly preferably represents hydrogen, methyl, methoxy, F, Cl or Br, R³ very particularly preferably represents hydrogen, m preferably represents 0 to 2, m particularly preferably represents 0 to 1, m very particularly preferably represents 0, R⁴ preferably represents $C_1$-$C_4$-alkyl, $C_3$-$C_6$-cycloalkyl, $C_2$-$C_4$-alkenyl, $C_2$-$C_4$-alkynyl, $C_1$-$C_4$-alkylsulfonyl, $C_1$-$C_4$-alkoxycarbonyl, $C_1$-$C_4$-alkylcarbonyl, aminocarbonyl, $C_1$-$C_4$-alkylaminocarbonyl, each of which is optionally mono- or polysubstituted by identical or different substituents, where the substituents independently of one another may be selected from the group consisting of halogen, cyano, $C_1$-$C_4$-alkyl, $C_1$-$C_4$-alkoxy, $C_1$-$C_4$-alkylthio, $C_1$-$C_4$-alkylsulfinyl or $C_1$-$C_4$-alkylsulfonyl, R⁴ particularly preferably represents methyl, ethyl, n-propyl, isopropyl, n-butyl, isobutyl, sec-butyl, tert-butyl, prop-2-enyl, prop-2-ynyl, methylsufonyl, methylcarbonyl, methoxycarbonyl, R⁴ very particularly preferably represents methyl, ethyl, isopropyl, R⁴ especially preferably represents methyl, R⁵ independently of one another preferably represents hydrogen, halogen, cyano, $C_1$-$C_4$-alkyl, $C_1$-$C_4$-alkoxy, $C_1$-$C_4$-haloalkyl, $C_1$-$C_4$-haloalkoxy, R⁵ independently of one another particularly preferably represents hydrogen, halogen or $C_1$-$C_4$-haloalkyl, R⁵ very particularly preferably represents fluorine, chlorine or bromine, R⁵ especially preferably represents 3-chloro, if n represents 1, n preferably represents 1, 2 or 3, n particularly preferably represents 1 or 2, n very particularly preferably represents 1, X preferably represents N, CH, CF or CCl, X particularly preferably represents N, CH or CF, X very particularly preferably represents N, R⁶ preferably represents hydrogen or $C_1$-$C_6$-alkyl, R⁶ particularly preferably represents hydrogen, methyl, ethyl, n-propyl, n-butyl, R⁶ very particularly preferably represents hydrogen or methyl, R⁷ preferably represents hydrogen or represents $C_1$-$C_6$-alkyl, $C_2$-$C_6$-alkenyl, $C_3$-$C_6$-alkynyl, each of which is optionally mono- or polysubstituted by identical or different substituents, where the substituents independently of one another may be selected from the group consisting of halogen, cyano, nitro, $C_1$-$C_6$-alkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_6$-alkoxycarbonyl, $C_1$-$C_6$-alkylcarbonyl, R⁷ also furthermore preferably represents optionally substituted phenylmethyl, pyridylmethyl, $C_3$-$C_6$-cycloalkyl, $C_3$-$C_6$-cycloalkyl-$C_1$-$C_4$-alkyl or $C_4$-$C_8$-bicycloalkyl, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, R⁷ also furthermore preferably represents phenyl, pyridyl, pyrimidinyl, thiazolyl, oxazolyl, pyrazolyl, thienyl or furanyl which is optionally mono- or polysubstituted by identical or different substituents, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl or $C_1$-$C_4$-alkylsulfonyl, $C_2$-$C_6$-alkoxycarbonyl, $C_2$-$C_6$-alkylcarbonyl, R⁷ particularly preferably represents hydrogen, represents $C_1$-$C_4$-alkyl, $C_2$-$C_4$-alkenyl, $C_3$-$C_4$-alkynyl, phenylmethyl, pyridylmethyl, $C_3$-$C_6$-cycloalkyl, $C_3$-$C_6$-cycloalkylmethyl, each of which is optionally mono- or polysubstituted by identical or different substituents, where the substituents independently of one another may be selected from the group consisting of halogen, cyano, methyl, ethyl, methoxy, ethoxy, methylthio, methylsufinyl, methylsulfonyl, methoxycarbonyl, methylcarbonyl, R⁷ very particularly preferably represents methyl, ethyl, n-propyl, isopropyl, n-butyl, isobutyl, sec-butyl or tert-butyl, cyclopropyl, cyclobutyl, 2-methylthio-1-methylethyl, cyclopropylmethyl, 1-cyclopropyl-1-methylethyl, 2-methoxy-1-methylethyl, propynyl, pyrid-2-ylmethyl, 2-methoxy-ethyl, 3-methoxy-prop-2-yl, R⁸, R⁹ independently of one another preferably represent hydrogen or represent $C_1$-$C_4$-alkyl, $C_2$-$C_4$-alkenyl, $C_3$-$C_4$-alkynyl, $C_3$-$C_4$-cycloalkyl, $C_2$-$C_4$-alkylcarbonyl or $C_2$-$C_4$-alkylsulfonyl, each of which is optionally mono- or polysubstituted by identical or different substituents, where the substituents independently of one another may be selected from the group consisting of halogen, cyano, nitro, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_4$-alkoxycarbonyl and $C_2$-$C_4$-alkylcarbonyl, R⁸, R⁹ independently of one another particularly preferably represent hydrogen, methyl, ethyl, n-propyl, isopropyl, n-butyl, isobutyl, sec-butyl or tert-butyl, cyclopropyl, prop-2-enyl, prop-2-ynyl, R⁸, R⁹ independently of one another very particularly preferably represent hydrogen, methyl, ethyl, methylcarbonyl, methylsulfonyl, R⁸, R⁹ independently of one another especially preferably represent hydrogen and methyl, R¹⁰ preferably represents a group selected from the group consisting of —C(=O)—R¹¹, —C(=O)—OR¹², —C(=O)—NR¹⁴R¹⁵, —S(O)₂—R¹⁶, R¹⁰ particularly preferably represents a group selected from the group consisting of —C(=O)—R¹¹, —C(=O)—OR¹², S(O)₂—R¹⁶, R¹⁰ very particularly preferably represents a group selected from the group consisting of —C(=O)—R¹¹, —C(=O)—OR¹², —S(O)₂—R¹⁶, R¹⁰ especially preferably represents the group —C(=O)—OR¹², R¹¹, R¹², R¹³, R¹⁶ independently of one another preferably represent $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl or aryl, each of which is optionally mono- or polysubstituted by identical or different substituents, where the substituents independently of one another may be selected from the group consisting of halogen, cyano, nitro, hydroxy, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^{11}$, $R^{12}$, $R^{13}$, $R^{16}$ independently of one another particularly preferably represent methyl, ethyl, n-propyl, isopropyl, n-, iso-, sec-, tert-butyl, propenyl, butenyl, propynyl, butynyl or phenyl, each of which is optionally mono- or polysubstituted by identical or different substituents, where the substituents independently of one another may be selected from the group consisting of halogen, cyano, methoxy, ethoxy, methylthio, methylsulfinyl, methylsulfonyl, methoxycarbonyl and methylcarbonyl, $R^{11}$, $R^{12}$, $R^{13}$, $R^{16}$ independently of one another very particularly preferably represent methyl, ethyl, n-propyl, isopropyl, prop-2-enyl, methoxyeth-2-yl, phenyl, $R^{12}$ especially preferably represents methyl, $R^{14}$, $R^5$, $R^{17}$, $R^{18}$ independently of one another preferably represent hydrogen or represent $R^{11}$, $R^{14}$, $R^{15}$, $R^{17}$, $R^{18}$ independently of one another particularly preferably represent hydrogen, methyl, ethyl, n-propyl, isopropyl, prop-2-enyl, methoxyeth-2-yl, phenyl, $R^{14}$, $R^{15}$, $R^{17}$, $R^{18}$ independently of one another very particularly preferably represent hydrogen or methyl, L preferably, particularly preferably and very particularly preferably represents

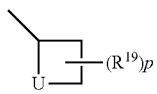

U preferably represents O, S, SO or $SO_2$,
U particularly preferably represents O, S, SO or $SO_2$,
U very particularly preferably represents O, S, SO or $SO_2$,
$R^{19}$ preferably represents hydrogen or $C_1$-$C_4$-alkyl,
$R^{19}$ particularly preferably represents hydrogen, methyl, ethyl, n-propyl, isopropyl,
$R^{19}$ very particularly preferably represents hydrogen or methyl,
p preferably represents 0, 1, 2,
p particularly preferably represents 0, 1, 2,
p very particularly preferably represents 0 or 1,
W preferably represents —$CH_2$—, —$CH_2O$—, —$OCH_2$—, —$CH_2OCH_2$—, —$CH_2S$—, —$CH_2SCH_2$—, —CH(CN)—, —CH($C_1$-$C_6$-alkyl)-, —C(di-$C_1$-$C_6$-alkyl)-, —$CH_2CH_2$—,
W particularly preferably represents —$CH_2$—, —$OCH_2$—, —CH($CH_3$), C($CH_3$)$_2$ or $CH_2CH_2$,
W very particularly preferably represents $CH_2$, or represents —$OCH_2$—,
W especially preferably represents —$OCH_2$, if Q represents Q-42.
W furthermore especially preferably represents $CH_2$, if Q represents Q-58.
Q preferably represents a 5- or 6-membered aromatic heterocyclic ring from the group of Q-15, Q-16, Q-24, Q-25, Q-34, Q-37, Q-38, Q-39, Q-40, Q-41, Q-42, Q-58, Q-59 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro or $C_1$-$C_2$-haloalkoxy, Q particularly preferably represents a 5- or 6-membered aromatic heterocyclic ring from the group of Q-37, Q-38, Q-39, Q-40, Q-41, Q-42, Q-58, Q-59 which is optionally mono- or polysubstituted, where the substituents independently of one another may be selected from the group consisting of chlorine, fluorine, iodine, cyano, trifluoromethyl and pentafluoroethyl, Q very particularly preferably represents the radicals

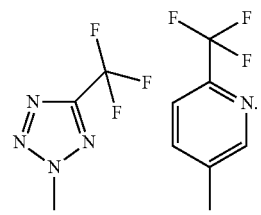

The above-recited general radical definitions and elucidations or those recited in preference ranges may be combined arbitrarily with one another, in other words including combinations between the respective ranges and preference ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Preparation Processes

Anthranilamides of the formula (I)

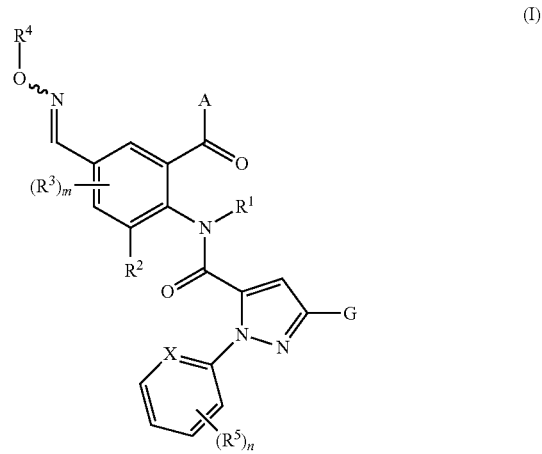

(I)

in which A, $R^1$, $R^2$, $R^3$, $R^4$, G, X, m and n have the meanings given above are obtained when, (A) for the synthesis of anthranilamides of the formula (I) in which $R^1$ represents hydrogen,
benzoxazinones of the formula (II)

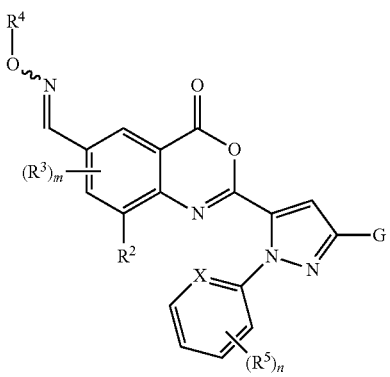

(II)

in which $R^2, R^3, R^4, R^5, G, X, m$ and $n$ have the meanings given above
are reacted with a compound of the formula (III)

A-H  (III)

in which A has the meanings given above
in the presence of a diluent.

(B) Anilines of the formula (IV)

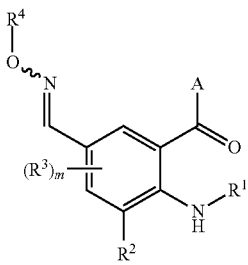

(IV)

in which $A, R^1, R^2, R^3, R^4$ and $m$ have the meanings given above
are reacted with carbonyl chlorides of the formula (V)

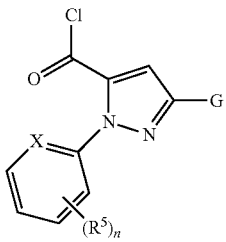

(V)

in which $R^5, G, X$ and $n$ have the meanings given above,
in the presence of an acid binder, (C) anilines of the formula (IV)

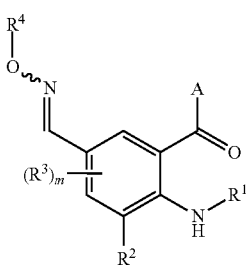

(IV)

in which $A, R^1, R^2, R^3, R^4$ and $m$ have the meanings given above
are reacted with a carboxylic acid of the formula (VI)

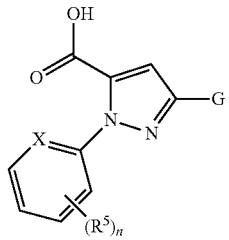

(VI)

in which $R^5, G, X$ and $n$ have the meanings given above,
in the presence of a condensing agent.

for the synthesis of anthranilamides of the formula (I) in which A represents $N(R^8)$—$N(R^9)(R^{10})$, (D) anthranilic hydrazides of the formula (VII)

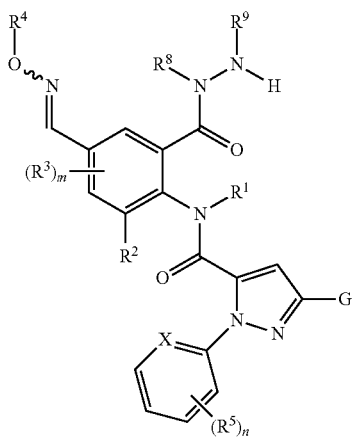

(VII)

in which $R^1, R^2, R^3, R^4, R^5, R^8, R^9, G, X, m$ and $n$ have the meanings given above,
are reacted with a unit Y—$R^{10}$, where $R^{10}$ has the meaning given above and Y represents a suitable leaving group such as, for example, halogen.

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned pests include:

pests from the phylum of: Arthropoda, in particular from the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Centruroides* spp.,

*Chorioptes* spp., *Dermanyssus gallinae*, *Dermatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis*, *Trichodectes* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp., *Stomoxys* spp., *Tabanus* spp., *Tannia* spp., *Tetanops* spp., *Tipula* spp.

From the order of the Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis*, *Solenopsis invicta*, *Tapinoma* spp., *Vespa* spp.

From the order of the Isopoda, for example, *Armadillidium vulgare*, *Oniscus asellus*, *Porcellio scaber*.

From the order of the Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*,

*Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Siphonaptera, for example, *Ceratophyllus* spp., *Ctenocephalides* spp., *Tunga penetrans, Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Zygentoma (=Thysanura), for example, *Lepisma saccharina, Thermobia domestica.*

For example *Lepisma saccharina, Thermobia domestica.*

Pests from the phylum of: Mollusca, especially from the class of the Bivalvia, for example *Dreissena* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Animal parasites from the phyla of: Plathelminthes and Nematoda, especially from the class of the helminths, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

Plant pests from the phylum of: Nematoda, i.e. phytoparasitic nematodes, especially *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

Subphylum: protozoa

It is also possible to control protozoa, such as *Eimeria.*

If appropriate, the compounds according to the invention can, at certain concentrations or application rates, also be used as herbicides, safeners, growth regulators or agents to improve plant properties, or as microbicides, for example as fungicides, antimycotics, bactericides, virices (including agents against viroids) or as agents against MLO (*mycoplasma*-like organisms) and RLO (*rickettsia*-like organisms). If appropriate, they can also be used as intermediates or precursors for the synthesis of other active compounds.

The present invention further relates to formulations and use forms prepared therefrom as crop protection compositions and/or pesticides, for example drench, drip and spray liquors, comprising at least one of the active compounds according to the invention. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemical active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the active compounds with auxiliaries, for example extenders, solvents and/or solid carriers and/or further auxiliaries, for example surfactants. The formulations are produced either in suitable facilities or else before or during application.

Auxiliaries used may be those substances which are suitable for imparting particular properties, such as particular physical, technical and/or biological properties, to the formulation of the active compound or to the use forms prepared from these formulations (for example ready-to-use crop protection compositions such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons such as xylene, toluene or alkylnaphthalenes, chlorinated aromatic or aliphatic hydrocarbons such as chlorobenzene, chloroethylene or methylene chloride, aliphatic hydrocarbons such as cyclohexane, paraffins, petroleum fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminum oxide and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Especially suitable are those extenders or carriers which are gaseous at standard temperature and under standard pressure, for example aerosol propellants such as halogenated hydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is advantageous when one of the active compounds and/or one of the inert carriers is insoluble in water and when application is carried out in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve the chemical and/or physical stability. Foam generators or antifoams may also be present.

In addition, the formulations and use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins, and synthetic phospholipids. Further possible auxiliaries are mineral and vegetable oils.

Optionally, further auxiliaries may be present in the formulations and the use forms derived therefrom.

Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive which is commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates, for example coconut fat ethoxylate (10) or isotridecyl ethoxylate (12), fatty acid esters, for example rapeseed oil methyl ester or soya oil methyl ester, fatty amine alkoxylates, for example tallowamine ethoxylate (15) or ammonium salts and/or phosphonium salts, for example ammonium sulfate or diammonium hydrogenphosphate.

The formulations contain generally between 0.01 and 98% by weight of active compound, preferably between 0.5 and 90%.

The active compounds according to the invention can be used as such or in formulations thereof, including in a mixture with one or more suitable fungicides, bactericides, acaricides, nematicides, insecticides, microbiologicals, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. In general, combination of the active compounds according to the invention and mixing partners gives synergistic effects, meaning that the efficacy of the mixture in question is greater than the efficacy of the individual components. It is generally possible to use the combinations in premixes, tankmixes or readymixes, and also in seed applications.

Particularly favorable mixing partners are, for example, the following:

The active compounds mentioned here under their "common names" are known and are described for example in The Pesticide Manual, 14th Ed., British Crop Protection Council 2006, or can be searched for on the Internet (e.g. http://www.alanwood.net/pesticides).

(1) Acetylcholinesterase (AChE) inhibitors, for example
  carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
  organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example
  cyclodiene organochlorines, for example chlordane and endosulfan; or
  phenylpyrazoles (fiproles), for example ethiprole and fipronil.

(3) Sodium channel modulators/voltage-dependent sodium channel blockers, for example
  pyrethroids, for example acrinathrin, allethrin, d-cis-trans allethrin, d-trans allethrin, bifenthrin, bioallethrin, bioallethrin S-cyclopentenyl isomer, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrine (pyrethrum), resmethrin, silafluofen, tefluthrin, tetramethrin, tetramethrin [(1R) isomers], tralomethrin and transfluthrin; or
  DDT; or methoxychlor.

(4) Nicotinergic acetylcholine receptor (nAChR) agonists, for example
  neonicotinoids, for example acetamiprid, clothianidin, dinotefuran, imidacloprid, nitenpyram, thiacloprid and thiamethoxam; or
  nicotine; or
  sulfoxaflor.

(5) Nicotinergic acetylcholine receptor (nAChR) allosteric activators, for example
  spinosyns, for example spinetoram and spinosad.

(6) Chloride channel activators, for example
  avermectins/milbemycins, for example abamectin, emamectin benzoate, lepimectin and milbemectin.

(7) Juvenile hormone imitators, for example
  juvenile hormone analogs, for example hydroprene, kinoprene and methoprene; or fenoxycarb; or pyriproxyfen.

(8) Active compounds having unknown or nonspecific mechanisms of action, for example
  alkyl halides, for example methyl bromide and other alkyl halides; or
  chloropicrin; or sulfuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, e.g. *Bacillus thuringiensis* subspecies *israelensis*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1; or
  *Bacillus sphaericus*.

(12) Oxidative phosphorylation inhibitors, ATP disruptors, for example diafenthiuron; or
  organotin compounds, e.g. azocyclotin, cyhexatin and fenbutatin oxide; or propargite; or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Molting disruptors, dipteran, for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example METI acaricides, e.g. fenazaquin, fenpyroximate, pyrimidifen, pyridaben, tebufenpyrad and tolfenpyrad; or
   rotenone (Derris).

(22) Voltage-gated sodium channel blockers, for example indoxacarb; or metaflumizone.

(23) Inhibitors of acetyl-CoA carboxylase, for example
   tetronic and tetramic acid derivatives, e.g. spirodiclofen, spiromesifen and spirotetramat.

(24) Complex-IV electron transport inhibitors, for example
   phosphines, for example aluminum phosphide, calcium phosphide, phosphine and zinc phosphide; or cyanide.

(25) Complex-II electron transport inhibitors, for example cyenopyrafen and cyflumetofen.

(28) Ryanodine receptor effectors, for example
   diamides, e.g. chlorantraniliprole, cyantraniliprole and flubendiamide.

Further active compounds having an unknown mechanism of action, such as, for example, amidoflumet, azadirachtin, benclothiaz, benzoximate, bifenazate, bromopropylate, chinomethionat, cryolite, dicofol, diflovidazin, fluensulfone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM 1-1582, for example VOTiVO™, BioNem), and the following known active compounds:

3-bromo-N-{2-bromo-4-chlor-6-[(1-cyclopropylethyl) carbamoyl]phenyl}-1-(3-chloropyridin-2-yl)-1H-pyrazole-5-carboxamide (known from WO 2005/077934), 4-{[(6-bromopyrid-3-yl)methyl](2-fluoroethyl)amino}furan-2 (5H)-one (known from WO 2007/115644), 4-{[(6-fluoropyrid-3-yl)methyl](2,2-difluoroethyl)amino}furan-2 (5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl) methyl](cyclopropyl)amino}furan-2(5H)-one (known from WO 2007/115643), 4-{[(6-chloropyrid-3-yl)methyl](cyclopropyl)amino}furan-2(5H)-one (known from EP A 0 539 588), 4-{[(6-chloropyrid-3-yl)methyl](methyl) amino}furan-2(5H)-one (known from EP A 0 539 588), {[1-(6-chloropyridin-3-yl)ethyl](methyl)oxido-$\lambda^4$-sulfanylidene}cyanamide (known from WO 2007/149134) and its diastereomers {[(1R)-1-(6-chloropyridin-3-yl)ethyl] (methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (likewise known from WO 2007/149134) and also diastereomers [(R)-methyl(oxido) {(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-2-sulfanylidene]cyanamide (A2), identified as diastereomer group A (known from WO 2010/074747, WO 2010/074751), [(R)-methyl (oxido){(1S)-1-[6-(trifluoromethyl)pyridin-3-yl]ethyl}-$\lambda^4$-sulfanylidene]cyanamide (B1) and [(S)-methyl(oxido) {(1R)-1-[6-(trifluoromethyl)pyridin-3-yl]ethyl}-$\lambda^4$-sulfanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5] dec-3-en-2-one (known from WO 2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO 2006/043635), afidopyropen (known from WO 2008/066153), 2-cyano-3-(difluoromethoxy)-N,N-dimethylbenzolsulfonamide (known from WO 2006/056433), 2-cyano-3-(difluoromethoxy)-N-methylbenzolsulfonamide (known from WO 2006/100288), 2-cyano-3-(difluoromethoxy)-N-ethylbenzenesulfonamide (known from WO 2005/035486), 4-(difluoromethoxy)-N-ethyl-N-methyl-1,2-benzothiazol-3-amine-1,1-dioxid (known from WO 2007/057407), N-[1-(2,3-dimethylphenyl)-2-(3,5-dimethylphenyl)ethyl]-4,5-dihydro-1,3-thiazol-2-amine (known from WO 2008/104503), {1'-[(2E)-3-(4-chlorophenyl)prop-2-en-1-yl]-5-fluorospiro [indol-3,4'-piperidine]-1(2H)-yl}(2-chloropyridin-4-yl) methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl) amino}-1,3-oxazol-2(5H)-one, 4-{[(6-chloropyridin-3-yl) methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl) amino}-1,3-oxazol-2(5H)-one (all known from WO 2010/005692), pyflubumide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl] carbonyl}amino)benzoyl]-1,2-diethylhydrazinecarboxylate (known from WO 2005/085216), methyl 2-[3,5-dibromo-2-

({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N$^1$-cyano-N-(2,2-difluoroethyl)ethanimidamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN 102057925), methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO 2011/049233), heptafluthrin, pyriminostrobin, flufenoxystrobin and 3-chloro-N$^2$-(2-cyanopropan-2-yl)-N$^1$-[4-(1,1,1,2,3,3,3-heptafluoropropan-2-yl)-2-methylphenyl]phthalamide (known from WO 2012/034472).

Fungicides (1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide, O-[1-(4-methoxyphenoxy)-3,3-dimethylbutan-2-yl]1H-imidazole-1-carbothioate and pyrisoxazole.

(2) Respiration inhibitors (respiratory chain inhibitors) at complex I and II of the respiratory chain, for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and the anti-empimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, benzovindiflupyr, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethyl-2,3-dihydro-1H-inden-4-yl)-1H-pyrazole-4-carboxamide, 1,3,5-trimethyl-N-(1,1,3-trimethyl-2,3-dihydro-1H-inden-4-yl)-1H-pyrazole-4-carboxamide, 1-methyl-3-(trifluoromethyl)-N-(1,1,3-trimethyl-2,3-dihydro-1H-inden-4-yl)-1H-pyrazole-4-carboxamide, 1-methyl-3-(trifluoromethyl)-N-[(3R)-1,1,3-trimethyl-2,3-dihydro-1H-inden-4-yl]-1H-pyrazole-4-carboxamide, 1-methyl-3-(trifluoromethyl)-N-[(3S)-1,1,3-trimethyl-2,3-dihydro-1H-inden-4-yl]-1H-pyrazole-4-carboxamide, 3-(difluoromethyl)-1-methyl-N-[(3S)-1,1,3-trimethyl-2,3-dihydro-1H-inden-4-yl]-1H-pyrazole-4-carboxamide, 3-(difluoromethyl)-1-methyl-N-[(3R)-1,1,3-trimethyl-2,3-dihydro-1H-inden-4-yl]-1H-pyrazole-4-carboxamide, 1,3,5-trimethyl-N-[(3R)-1,1,3-trimethyl-2,3-dihydro-1H-inden-4-yl]-1H-pyrazole-4-carboxamide, 1,3,5-trimethyl-N-[(3S)-1,1,3-trimethyl-2,3-dihydro-1H-inden-4-yl]-1H-pyrazole-4-carboxamide, benodanil, 2-chloro-N-(1,1,3-trimethyl-2,3-dihydro-1H-inden-4-yl)pyridine-3-carboxamide, isofetamid.

(3) Respiration inhibitors (respiratory chain inhibitors) at complex III of the respiratory chain, for example ametoctradin, amisulbrom, azoxystrobin, cyazofamid, coumethoxystrobin, coumoxystrobin, dimoxystrobin, enoxastroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylacetamide, fenaminostrobin, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyacrylate, N-(3-ethyl-3,5,5-trimethylcyclohexyl)-3-formamido-2-hydroxybenzamide, 2-{2-[(2,5-dimethylphenoxy)methyl]phenyl}-2-methoxy-N-methylacetamide and 2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4] triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulfur and sulfur preparations, for example calcium polysulfide, thiram, tolylfluanid, zineb, ziram and anilazin.

(6) Resistance inductors, for example acibenzolar-S-methyl, isotianil, probenazole, tiadinil and laminarin.

(7) Amino acid and protein biosynthesis inhibitors, for example andoprim, blasticidin-S, cyprodinil, kasugamycin, kasugamycin hydrochloride hydrate, mepanipyrim, pyrimethanil, 3-(5-fluoro-3,3,4,4-tetramethyl-3,4-dihydroisoquinolin-1-yl)quinoline, oxytetracyclines and streptomycin.

(8) Inhibitors of ATP production, for example, fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A, valifenalate and polyoxin B.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid and octhilinone.

(13) Signal transduction inhibitors, for example chlozolinate, fenpiclonil, fludioxonil, iprodione, procymidone, quinoxyfen, vinclozolin and proquinazid.

(14) Decouplers, for example binapacryl, dinocap, ferimzone, fluazinam and meptyldinocap.

(15) Further compounds, for example benthiazole, bethoxazine, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulfate, diphenylamine, EcoMate, fenpyrazamine, flumetover, fluoroimide, flusulfamide, flutianil, fosetyl-aluminum, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, oxamocarb, oxyfenthiin, pentachlorophenol and its salts, phenothrin, phosphoric acid and its salts, propamocarb-fosetylate, propanosine-sodium, pyrimorph, pyrrolnitrin, tebufloquin, tecloftalam, tolnifanide, triazoxide, trichlamide, zarilamid, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-[5-phenyl-4,5-dihydro-1,2-oxazol-3-yl]-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl] pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl(2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-{(E)-[(cyclopropylmethoxy)imino][6-(difluoromethoxy)-2,3-difluorophenyl]methyl}-2-phenylacetamide, N—{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylene]amino}oxy)methyl]pyridin-2-yl}carbamate, phenazine-1-carboxylic acid, quinolin-8-ol, quinolin-8-ol sulfate (2:1), tert-butyl {6-[({[(1-methyl-1H-tetrazol-5-yl)(phenyl)methylene]

amino}oxy)methyl]pyridin-2-yl}carbamate, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]nicotinamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)nicotinamide, 2-chloro-N-[4'-(3,3-dimethylbut-1-yn-1-yl)biphenyl-2-yl]nicotinamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]nicotinamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]nicotinamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid, but-3-yn-1-yl {6-[({[(Z)-(1-methyl-1H-tetrazol-5-yl)(phenyl)methylene]amino}oxy)methyl]pyridin-2-yl}carbamate, 4-amino-5-fluoropyrimidin-2-ol (tautomeric form: 4-amino-5-fluoropyrimidin-2(1H)-one), propyl 3,4,5-trihydroxybenzoate, 1,3-dimethyl-N-(1,1,3-trimethyl-2,3-dihydro-1H-inden-4-yl)-1H-pyrazole-4-carboxamide, 1,3-dimethyl-N-[(3R)-1,1,3-trimethyl-2,3-dihydro-1H-inden-4-yl]-1H-pyrazole-4-carboxamide, 1,3-dimethyl-N-[(3S)-1,1,3-trimethyl-2,3-dihydro-1H-inden-4-yl]-1H-pyrazole-4-carboxamide, [3-(4-chloro-2-fluorophenyl)-5-(2,4-difluorophenyl)-1,2-oxazol-4-yl](pyridin-3-yl)methanol, (S)-[3-(4-chloro-2-fluorophenyl)-5-(2,4-difluorophenyl)-1,2-oxazol-4-yl](pyridin-3-yl)methanol, (R)-[3-(4-chloro-2-fluorophenyl)-5-(2,4-difluorophenyl)-1,2-oxazol-4-yl](pyridin-3-yl)methanol, 2-{[3-(2-chlorophenyl)-2-(2,4-difluorophenyl)oxiran-2-yl]methyl}-2,4-dihydro-3H-1,2,4-triazole-3-thione, 1-{[3-(2-chlorophenyl)-2-(2,4-difluorophenyl)oxiran-2-yl]methyl}-1H-1,2,4-triazol-5-yl thiocyanate, 5-(allylsulfanyl)-1-{[3-(2-chlorophenyl)-2-(2,4-difluorophenyl)oxiran-2-yl]methyl}-1H-1,2,4-triazole, 2-[1-(2,4-dichlorophenyl)-5-hydroxy-2,6,6-trimethylheptan-4-yl]-2,4-dihydro-3H-1,2,4-triazole-3-thione, 2-{[rel(2R,3S)-3-(2-chlorophenyl)-2-(2,4-difluorophenyl)oxiran-2-yl]methyl}-2,4-dihydro-3H-1,2,4-triazole-3-thione, 2-{[rel(2R,3R)-3-(2-chlorophenyl)-2-(2,4-difluorophenyl)oxiran-2-yl]methyl}-2,4-dihydro-3H-1,2,4-triazole-3-thione, 1-{[rel(2R,3S)-3-(2-chlorophenyl)-2-(2,4-difluorophenyl)oxiran-2-yl]methyl}-1H-1,2,4-triazol-5-yl thiocyanate, 1-{[rel(2R,3R)-3-(2-chlorophenyl)-2-(2,4-difluorophenyl)oxiran-2-yl]methyl}-1H-1,2,4-triazol-5-yl thiocyanate, 5-(allylsulfanyl)-1-{[rel(2R,3S)-3-(2-chlorophenyl)-2-(2,4-difluorophenyl)oxiran-2-yl]methyl}-1H-1,2,4-triazole, 5-(allylsulfanyl)-1-{[rel(2R,3R)-3-(2-chlorophenyl)-2-(2,4-difluorophenyl)oxiran-2-yl]methyl}-1H-1,2,4-triazole, 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, 2-[(2R,4R,5R)-1-(2,4-dichlorophenyl)-5-hydroxy-2,6,6-trimethylheptan-4-yl]-2,4-dihydro-3H-1,2,4-triazole-3-thione, 2-[(2S,4R,5R)-1-(2,4-dichlorophenyl)-5-hydroxy-2,6,6-trimethylheptan-4-yl]-2,4-dihydro-3H-1,2,4-triazole-3-thione, 2-[(2S,4S,5R)-1-(2,4-dichlorophenyl)-5-hydroxy-2,6,6-trimethylheptan-4-yl]-2,4-dihydro-3H-1,2,4-triazole-3-thione, 2-[(2R,4S,5R)-1-(2,4-dichlorophenyl)-5-hydroxy-2,6,6-trimethylheptan-4-yl]-2,4-dihydro-3H-1,2,4-triazole-3-thione, 2-[(2R,4R,5S)-1-(2,4-dichlorophenyl)-5-hydroxy-2,6,6-trimethylheptan-4-yl]-2,4-dihydro-3H-1,2,4-triazole-3-thione, 2-[(2S,4R,5S)-1-(2,4-dichlorophenyl)-5-hydroxy-2,6,6-trimethylheptan-4-yl]-2,4-dihydro-3H-1,2,4-triazole-3-thione, 2-fluoro-6-(trifluoromethyl)-N-(1,1,3-trimethyl-2,3-dihydro-1H-inden-4-yl)benzamide, 2-(6-benzylpyridin-2-yl)quinazoline, 2-[6-(3-fluoro-4-methoxyphenyl)-5-methylpyridin-2-yl]quinazoline, 3-(4,4-difluoro-3,3-dimethyl-3,4-dihydroisoquinolin-1-yl)quinoline, abscisic acid, 3-(difluoromethyl)-N-methoxy-1-methyl-N-[1-(2,4,6-trichlorophenyl)propan-2-yl]-1H-pyrazole-4-carboxamide, N'-[5-bromo-6-(2,3-dihydro-1H-inden-2-yloxy)-2-methylpyridin-3-yl]-N-ethyl-N-methylimidoformamide, N'-{5-bromo-6-[1-(3,5-difluorophenyl)ethoxy]-2-methylpyridin-3-yl}-N-ethyl-N-methylimidoformamide, N'-{5-bromo-6-[(1R)-1-(3,5-difluorophenyl)ethoxy]-2-methylpyridin-3-yl}-N-ethyl-N-methylimidoformamide, N'-{5-bromo-6-[(1S)-1-(3,5-difluorophenyl)ethoxy]-2-methylpyridin-3-yl}-N-ethyl-N-methylimidoformamide, N'-{5-bromo-6-[(cis-4-isopropylcyclohexyl)oxy]-2-methylpyridin-3-yl}-N-ethyl-N-methylimidoformamide, N'-{5-bromo-6-[(trans-4-isopropylcyclohexyl)oxy]-2-methylpyridin-3-yl}-N-ethyl-N-methylimidoformamide, N-cyclopropyl-3-(difluoromethyl)-5-fluoro-N-(2-isopropylbenzyl)-1-methyl-1H-pyrazole-4-carboxamide, N-cyclopropyl-N-(2-cyclopropylbenzyl)-3-(difluoromethyl)-5-fluoro-1-methyl-1H-pyrazole-4-carboxamide, N-(2-tert-butylbenzyl)-N-cyclopropyl-3-(difluoromethyl)-5-fluoro-1-methyl-1H-pyrazole-4-carboxamide, N-(5-chloro-2-ethylbenzyl)-N-cyclopropyl-3-(difluoromethyl)-5-fluoro-1-methyl-1H-pyrazole-4-carboxamide, N-(5-chloro-2-isopropylbenzyl)-N-cyclopropyl-3-(difluoromethyl)-5-fluoro-1-methyl-1H-pyrazole-4-carboxamide, N-cyclopropyl-3-(difluoromethyl)-N-(2-ethyl-5-fluorobenzyl)-5-fluoro-1-methyl-1H-pyrazole-4-carboxamide, N-cyclopropyl-3-(difluoromethyl)-5-fluoro-N-(5-fluoro-2-isopropylbenzyl)-1-methyl-1H-pyrazole-4-carboxamide, N-cyclopropyl-N-(2-cyclopropyl-5-fluorobenzyl)-3-(difluoromethyl)-5-fluoro-1-methyl-1H-pyrazole-4-carboxamide, N-(2-cyclopentyl-5-fluorobenzyl)-N-cyclopropyl-3-(difluoromethyl)-5-fluoro-1-methyl-1H-pyrazole-4-carboxamide, N-cyclopropyl-3-(difluoromethyl)-5-fluoro-N-(2-fluoro-6-isopropylbenzyl)-1-methyl-1H-pyrazole-4-carboxamide, N-cyclopropyl-3-(difluoromethyl)-N-(2-ethyl-5-methylbenzyl)-5-fluoro-1-methyl-1H-pyrazole-4-carboxamide, N-cyclopropyl-3-(difluoromethyl)-5-fluoro-N-(2-isopropyl-5-methylbenzyl)-1-methyl-1H-pyrazole-4-carboxamide, N-cyclopropyl-N-(2-cyclopropyl-5-methylbenzyl)-3-(difluoromethyl)-5-fluoro-1-methyl-1H- pyrazole-4-carboxamide, N-(2-tert-butyl-5-methylbenzyl)-N-cyclopropyl-3-(difluoromethyl)-5-fluoro-1-methyl-1H-pyrazole-4-carboxamide, N-[5-chloro-2-(trifluoromethyl)benzyl]-N-cyclopropyl-3-(difluoromethyl)-5-fluoro-1-methyl-1H-pyrazole-4-carboxamide, N-cyclopropyl-3-(difluoromethyl)-5-fluoro-1-methyl-N-[5-methyl-2-(trifluoromethyl)benzyl]-1H-pyrazole-4-carboxamide, N-[2-chloro-6-(trifluoromethyl)benzyl]-N-cyclopropyl-3-(difluoromethyl)-5-fluoro-1-methyl-1H-pyrazole-4-carboxamide, N-[3-chloro-2-fluoro-6-(trifluoromethyl)benzyl]-N-cyclopropyl-3-(difluoromethyl)-5-fluoro-1-methyl-1H-pyrazole-4-carboxamide, N-cyclopropyl-3-(difluoromethyl)-N-(2-ethyl-4,5-dimethylbenzyl)-5-fluoro-1-methyl-1H-pyrazole-4-carboxamide, N-cyclopropyl-3-(difluoromethyl)-5-fluoro-N-(2-isopropylbenzyl)-1-methyl-1H-pyrazol-4-carbothioamide, 3-(difluoromethyl)-N-(7-fluoro-1,1,3-trimethyl-2,3-dihydro-1H-inden-4-yl)-1-methyl-1H-pyrazole-4-carboxamide, 3-(difluoromethyl)-N-[(3R)-7-fluoro-1,1,3-trimethyl-2,3-dihydro-1H-inden-4-yl]-1-methyl-1H-pyrazole-4-carboxamide, 3-(difluoromethyl)-N-[(3S)-7-fluoro-1,1,3-trimethyl-2,3-dihydro-1H-inden-4-yl]-1-methyl-1H-pyrazole-4-carboxamide.

All the mixing partners mentioned in classes (1) to (15), as the case may be, may form salts with suitable bases or acids if they are capable of doing so on the basis of their functional groups.

The active compounds mentioned here under their "common names" are known and are described for example in The Pesticide Manual, 14th Ed., British Crop Protection Council 2006, or can be searched for on the Internet (e.g. http://www.alanwood.net/pesticides).

Another possibility is a mixture with other known active compounds, such as herbicides, fertilizers, growth regulators, safeners, semiochemicals, or else with agents for improving the plant properties.

When used as insecticides, the active compounds according to the invention may also be present in their commercially available formulations and in the use forms, prepared from these formulations, in a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, in mixtures with inhibitors which reduce degradation of the active compound after use in the environment of the plant, on the surface of parts of plants or in plant tissues.

The active compound content of the use forms prepared from the commercially available formulations may vary within wide limits. The active compound concentration of the use forms may be from 0.00000001 to 95% by weight of active compound, preferably between 0.00001 and 1% by weight.

The application is accomplished in a customary manner appropriate for the use forms.

All plants and plant parts can be treated in accordance with the invention. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights.

Plant parts are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Parts of plants also include harvested material and vegetative and generative propagation material, for example cuttings, tubers, rhizomes, slips and seed.

The treatment according to the invention of the plants and plant parts with the active compounds is carried out directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts" and "parts of plants" or "plant parts" have been elucidated above.

Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, increased storage life and/or processability of the harvested products.

The preferred transgenic plants or plant cultivars (those obtained by genetic engineering) which are to be treated in accordance with the invention include all plants which, through the genetic modification, received genetic material which imparts particular advantageous useful properties ("traits") to these plants.

Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya, potatoes, cotton, tobacco and oilseed rape. Traits that are particularly emphasized are the improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain herbicidally active compounds, for example imidazolinones, sulfonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the commercial names Roundup Ready® (tolerance to glyphosate e.g. maize, cotton, soya), Liberty Link® (tolerance to phosphinothricin, e.g. oilseed rape), IMI® (tolerance to imidazolinones) and STS® (tolerance to sulfonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are yet to be developed and will be developed and/or marketed in the future.

The plants listed can be treated in accordance with the invention in a particularly advantageous manner with the compounds of the general formula I and/or the active compound mixtures according to the invention. The areas of preference stated above for the active compounds or mixtures also apply to the treatment of these plants. Particular emphasis is given to the treatment of plants with the compounds or mixtures specifically mentioned in the present text.

In addition, the active compounds according to the invention can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health sector, i.e. in the field of veterinary medicine, the active compounds according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phtirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp. (e.g. *Supella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honey bees. The animals also include domestic animals—also referred to as companion animals—for example dogs, cats, caged birds, aquarium fish, and what are known as test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the active compounds according to the invention enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active compounds act by reducing the occurrence of the parasite in question in an animal infested with such parasites to harmless levels. More specifically, "control" as used herein means that the active compound kills the parasite in question, retards its growth or inhibits its proliferation.

In general, the active compounds according to the invention can be employed directly when they are used for the treatment of animals. They are preferably employed in the form of pharmaceutical compositions which may comprise pharmaceutically acceptable excipients and/or auxiliaries known in the prior art.

In the sector of animal health and in animal husbandry, the active compounds are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of molded articles containing the active compound, such as collars, earmarks, tailmarks, limb bands, halters, marking devices, etc. The active compounds can be formulated as a shampoo or as suitable formulations applicable in aerosols or unpressurized sprays, for example pump sprays and atomizer sprays.

In the case of employment for livestock, poultry, domestic pets, etc., the active compounds according to the invention can be employed as formulations (for example powders, wettable powders ["WP"], emulsions, emulsifiable concentrates ["EC"], free-flowing compositions, homogeneous solutions and suspension concentrates ["SC"]), which contain the active compounds in an amount of 1% to 80% by weight, directly or after dilution (e.g. 100- to 10 000-fold dilution), or they can be used as a chemical bath.

It has also been found that the compounds according to the invention have strong insecticidal action against insects which destroy industrial materials.

The following insects may be mentioned as examples and as preferred—but without limitation:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus;*

Dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccharina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

With regard to possible additional mixing partners, reference is made to the abovementioned insecticides and fungicides.

Moreover, the compounds according to the invention can be employed for protecting objects which come into contact with saltwater or brackish water, in particular hulls, screens, nets, buildings, moorings and signaling systems, against fouling.

In addition, the compounds according to the invention can be used as antifouling compositions, alone or in combinations with other active compounds.

The active compounds are also suitable for controlling animal pests in the domestic sector, in the hygiene sector and in the protection of stored products, in particular insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longilpalpa*.

From the order of the Saltatoria, for example, *Acheta domesticus*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active compounds, such as phosphoric esters, carbamates, pyrethroids, neonicotinoids, growth regulators or active compounds from other known classes of insecticides.

Application is effected in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Description of the Preparation Processes and Intermediates

Process (A)

Using, for example, 2-[1-(3-chloropyridin-2-yl)-3-(2,2-difluoroethoxy)-1H-pyrazol-5-yl]-8-methyl-4-oxo-4H-3,1-benzoxazine-6-carbaldehyde O-methyl oxime and methyl 1-methylhydrazinecarboxylate, the course of process (A) can be illustrated by the formula scheme below.

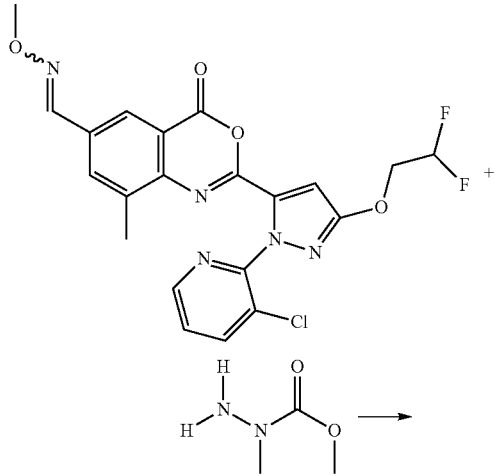

-continued

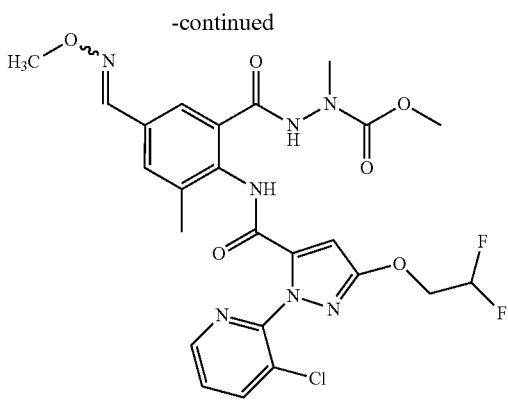

The formula (II) provides a general definition of the benzoxazinones required as starting materials for carrying out process (A).

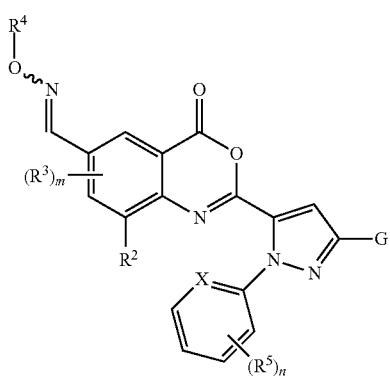

In this formula (II), $R^2$, $R^3$, $R^4$, $R^5$, G, X, m and n have the meaning given above.

Benzoxazinones of the formula (II) are novel. They are obtained, for example, by reacting pyrazolecarboxylic acid derivatives of the formula (VI)

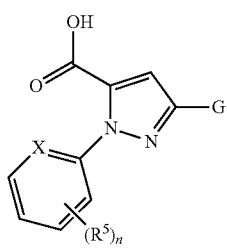

in which $R^5$, G, X and n have the meaning given above with anthranilic acids of the formula (VIII)

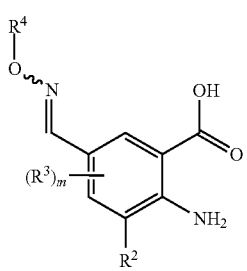

in which $R^2$, $R^3$, $R^4$ and m have the meanings given above, in the presence of a base (for example triethylamine or pyridine) and in the presence of a sulfonyl chloride (for example methanesulfonyl chloride) and, if appropriate, in the presence of a diluent (for example acetonitrile).

Some of the anthranilic acids of the formula (VIII) are known (WO 2013/024005). They can be obtained analogously to generally known process from aldehydes of the formula (IX)

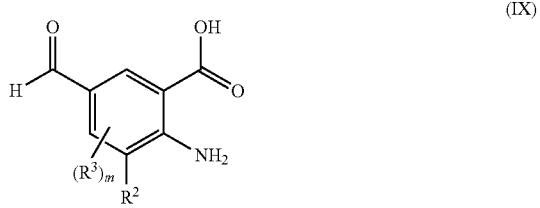

in which $R^2$, $R^3$ and m have the meanings given above by reaction with hydroxylamines of the formula (X)

$$R^4\text{—O—NH}_2 \qquad (X).$$

Some of the aldehydes of the formula (IX) are known (WO 2013/024005). They can be obtained analogously to generally known process from anthranilic acids of the formula (IX)

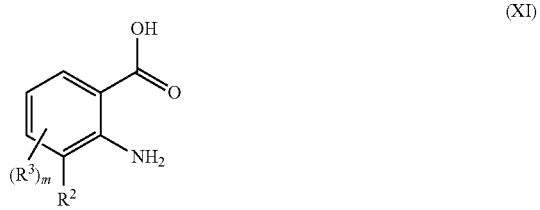

by reaction with formylating agents such as, for example, formaldehyde analogously to known compounds (e.g. FR 1377226 (1964)).

Anthranilic acids of the formula (XI) are commercially available, known from the literature or can be synthesized analogously to known processes.

The pyrazolecarboxylic acids of the formula (VI) required as starting materials for carrying out process

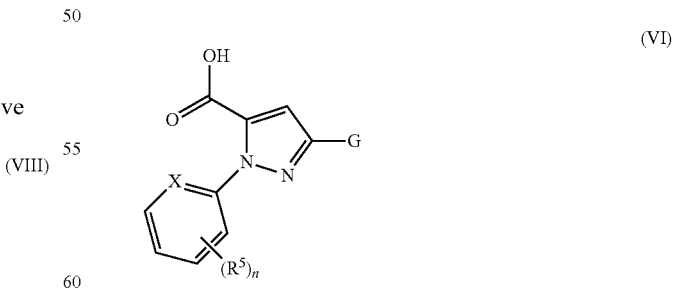

in which G, X, n and $R^5$ have the meaning given above are novel, known from the literature or can be prepared analogously to processes known from the literature.

Examples include:
3-bromo-1-(3-chloropyridin-2-yl)-1H-pyrazole-5-carboxylic acid (lit.: WO 2003/016283)

1-(3-chloropyridin-2-yl)-3-(trifluoromethyl)-1H-pyrazole-5-carboxylic acid (lit.: WO 2002/048115)
1-(3-chloropyridin-2-yl)-3-(2,2,2-trifluoroethoxy)-1H-pyrazole-5-carboxylic acid (lit.: WO 2003/015518)
1-(3-chloropyridin-2-yl)-3-(difluoromethoxy)-1H-pyrazole-5-carboxylic acid (lit.: Bioorganic & Medicinal Chemistry Letters (2007), 17(22), 6274-6279)
1-(3-chloropyridin-2-yl)-3-methoxy-1H-pyrazole-5-carboxylic acid (lit.: GB 2463318)
1-(3-chloropyridin-2-yl)-3-(difluoromethyl)-1H-pyrazole-5-carboxylic acid (lit.: WO 2007/093402)
1-(3-chloropyridin-2-yl)-3-{[5-(trifluoromethyl)-2H-tetrazol-2-yl]methyl}-1H-pyrazole-5-carboxylic acid (lit.: WO 2011/157664)

Process (B)

Using, for example, 2-amino-5-[(E)-(methoxyimino)methyl]-N,3-dimethylbenzamide and 1-(3-chloropyridin-2-yl)-3-(2,2-difluoroethoxy)-1H-pyrazole-5-carbonyl chloride as starting materials, the course of process (A) can be illustrated by the formula scheme below.

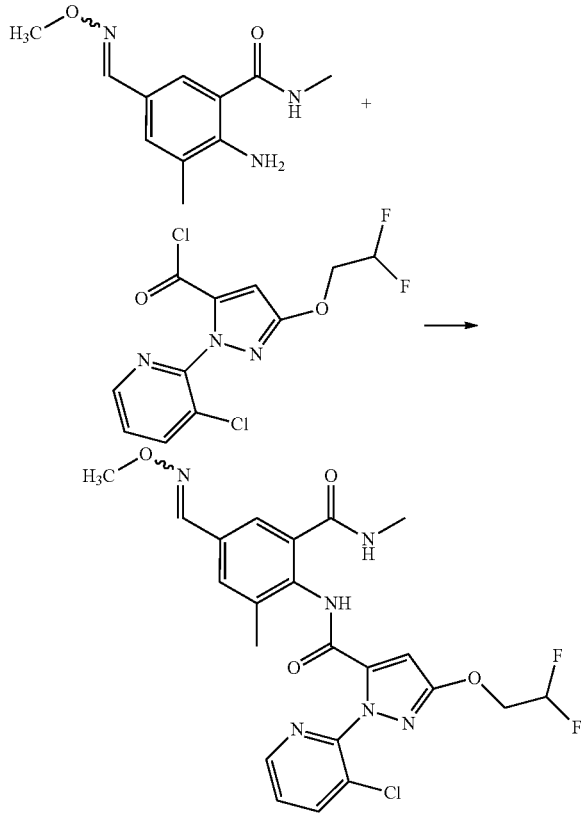

The formula (IV) provides a general definition of the aminobenzamides required as starting materials for carrying out process (B).

(IV)

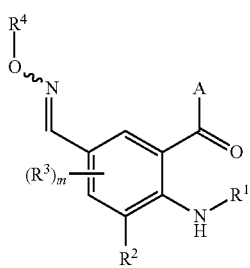

In this formula (IV), A, $R^1$, $R^2$, $R^3$, $R^4$ and m have the meaning given above.

The process (B) is carried out in the presence of an acid binder. Suitable for this purpose are all inorganic or organic bases customary for such coupling reactions. Preference is given to using hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). It is also possible to use optionally polymer-supported acid binders, such as, for example, polymer-supported diisopropylamine and polymer-supported dimethylaminopyridine.

The process (B) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl keton or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

Compounds of the formula (IV) are novel. Compounds of the formula (IV) can be obtained, for example, by reacting compounds of the formula (IVa)

(IVa)

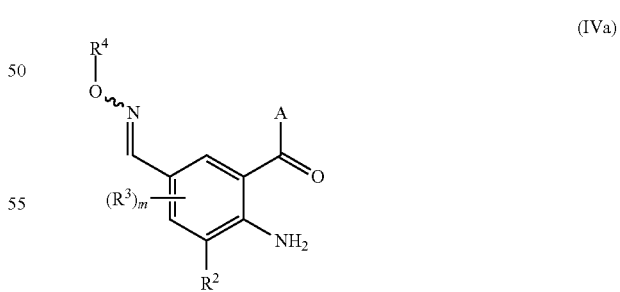

in which A, $R^2$, $R^3$, $R^4$ and m have the meaning given above according to a generally known reaction with compounds $R^1$—Y, where Y represents a leaving group such as, for example, halogen, in the presence of a base.

Compounds of the formula (IVa) are novel. Compounds of the formula (IVa) can be obtained, for example, by reacting anthranilic acids of the formula (VIII)

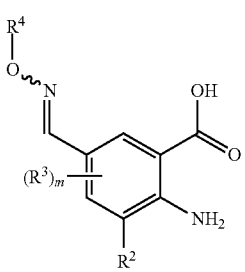

(VIII)

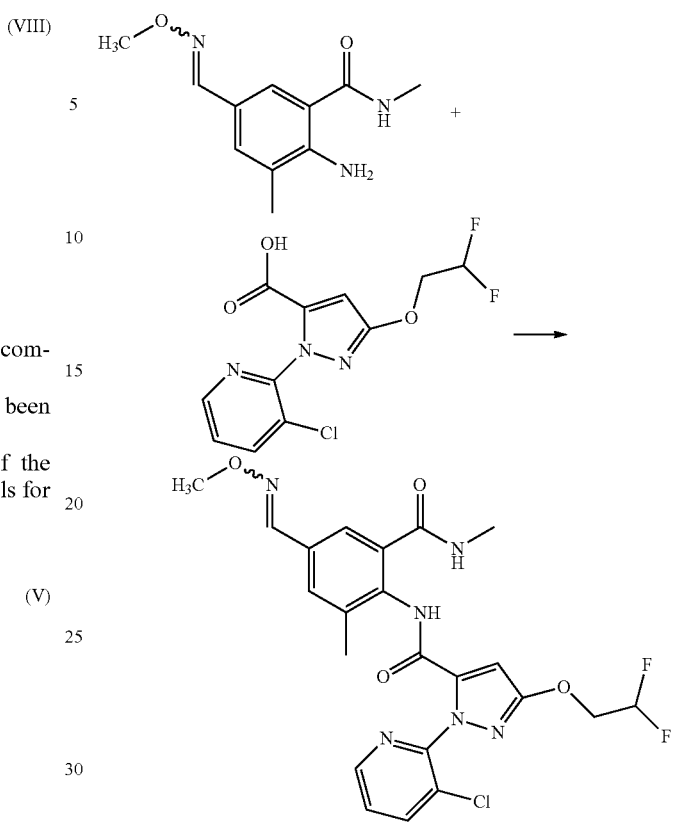

according to a generally known reaction with amino compounds A-H in the presence of an activating agent.

Compounds of the formula (VIII) have already been described in connection with process (A).

The formula (V) provides a general definition of the pyrazolecarbonyl chlorides required as starting materials for carrying out process (A).

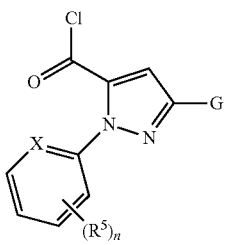

(V)

In this formula (V), G, X, n and $R^5$ have the meaning given above.

Pyrazolcarbonyl chlorides of the formula (V) are known from the literature or can be prepared analogously to processes known from the literature by reacting pyrazolecarboxylic acid derivatives of the formula (VI)

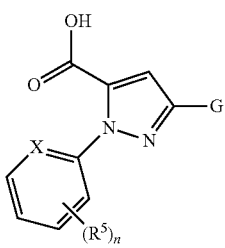

(VI)

in which G, X, n and $R^5$ have the meaning given above with a chlorinating agent (for example thionyl chloride or oxalyl chloride) in the presence of an inert diluent (for example toluene or dichloromethane) in the presence of a catalytic amount of N,N-dimethylformamide.

Pyrazolecarboxylic acids of the formula (VI) have already been described in connection with process (A).

Process (C)

Using, for example, 2-amino-5-[(E)-(methoxyimino) methyl]-N,3-dimethylbenzamide and 1-(3-chloropyridin-2-yl)-3-(2,2-difluoroethoxy)-1H-pyrazole-5-carboxylic acid as starting materials, the course of the process (B) can be illustrated by the formula scheme below.

The anthranilamides of the formula (IV) required as starting materials for carrying out process (C) have already been described in connection with process (B).

The pyrazolecarboxylic acids furthermore required as starting materials for carrying out process (B) have already been described for process (A).

The process (C) is carried out in the presence of a condensing agent. Suitable agents for this purpose are all agents customary for such coupling reactions. Acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methansulfonyl chloride; carbodiimides, such as N,N'-dicyclohexylcarbodiimide (DCC) or other customary condensing agents, such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris(dimethylamino)phosphonium hexafluorphosphate may be mentioned by way of example. It is likewise possible to use polymer-supported reagents, for example polymer-bound cyclohexylcarbodiimide.

Process (C) is, if appropriate, carried out in the presence of a catalyst. 4-Dimethylaminopyridine, 1-hydroxybenzotriazole or dimethylformamide may be mentioned by way of example.

Process (C) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Process (D)

Using, for example, 1-(3-chloropyridin-2-yl)-3-(difluoromethoxy)-N-{2-(hydrazinocarbonyl)-4-[(E)-(methoxyimino)methyl]-6-methylphenyl}-1H-pyrazole-5-carboxamide and methyl chloroformate as starting materials, the course of the process (D) can be illustrated by the formula scheme below.

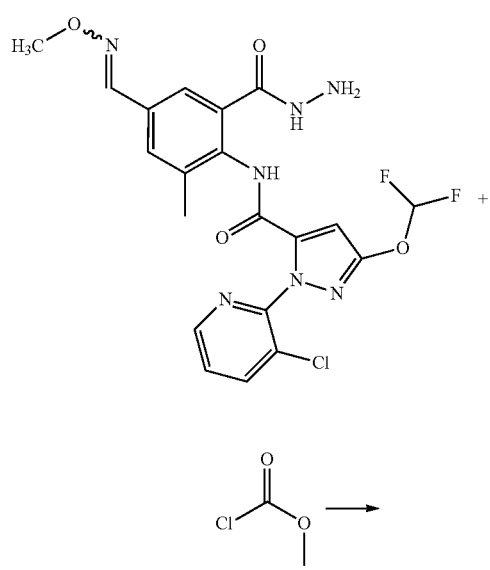

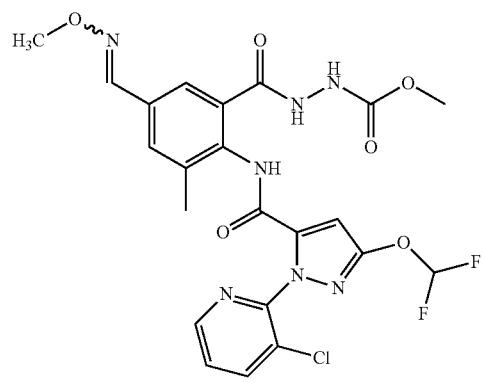

The formula (VII) provides a general definition of the hydrazides required as starting materials for carrying out process (D).

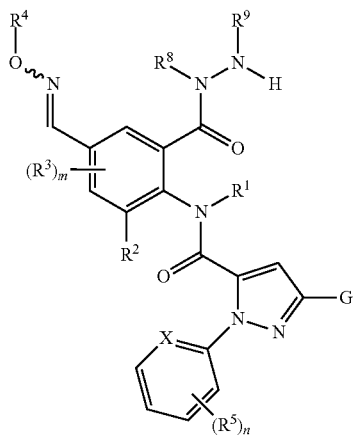

In this formula (VII), $R^1$, $R^2$, $R^3$, $R^4$, $R^5$, $R^8$, $R^9$, G, X, m and n have the meaning given above.

Process (D) is carried out in the presence of an acid binder as described in connection with process (B).

Compounds of the formula (VII) are novel. Compounds of the formula (VII) can be obtained, for example, by reacting benzoxazinones of the formula (II)

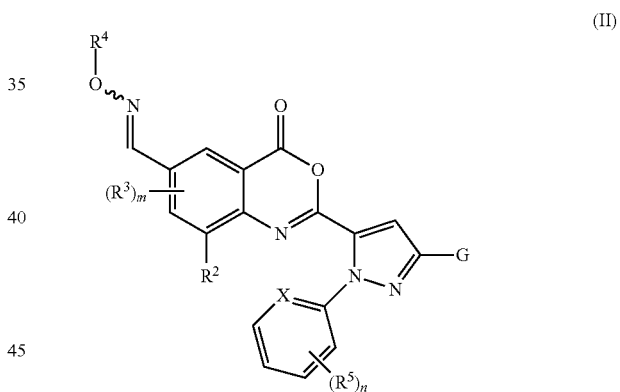

in which $R^2$, $R^3$, $R^4$, $R^5$, G, X, m and n have the meaning given above analogously to process (A) with hydrazines of the formula (XII)

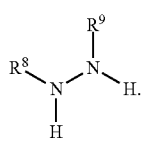

Compounds of the formula (II) have already been described in connection with process (A).

Synthesis of Pyrazolecarboxylic Acids of the Formula (VI)

1-(3-Chloropyridin-2-yl)-3-(2,2-difluoroethoxy)-1H-pyrazole-5-carboxylic acid

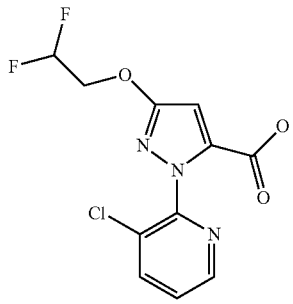 [SMILES: O=C(O)c1cc(OCC(F)F)nn1-c1ncccc1Cl]

Step 1: Ethyl 1-(3-chloropyridin-2-yl)-3-(2,2-difluoroethoxy)-1H-pyrazole-5-carboxylate 1.00 g (3.73 mmol) of ethyl 1-(3-chloropyridin-2-yl)-3-hydroxy-1H-pyrazole-5-carboxylate (lit.: WO 2004046129) were initially charged in 6 ml of pyridine, and 1.08 g (5.60 mmol) of 2-iodo-1,1-difluoroethane and 1.03 g (7.47 mmol) of potassium carbonate were successively added. The mixture was then heated at 100° C. for 18 hours. After cooling, the reaction mixture was poured onto water and the precipitated solid was filtered off and dried. This gave 670 mg (52% of theory) of ethyl 1-(3-chloropyridin-2-yl)-3-hydroxy-1H-pyrazole-5-carboxylate.

HPLC-MS: log P=2.74; mass (m/z): 331.9 (M+H)$^+$; $^1$H-NMR (400 MHz, CD$_3$CN, δ, ppm): 1.17 (t, 3H), 4.15 (q, 2H), 4.44 (m, 2H), 6.20 (t, 1H), 6.56 (s, 1H), 7.53 (m, 1H), 8.02 (d, 1H), 8.50 (m, 1H).

Step 2: 1-(3-Chloropyridin-2-yl)-3-(2,2-difluoroethoxy)-1H-pyrazole-5-carboxylic acid 670 mg (1.57 mmol) of ethyl 1-(3-chloropyridin-2-yl)-3-(2,2-difluoroethoxy)-1H-pyrazole-5-carboxylate were initially charged in 3.4 ml of ethanol, and 182 mg (2.04 mmol) of a 45% strength NaOH solution were added. The mixture was then stirred at room temperature for 18 hours. The reaction mixture was poured onto water and acidified with dilute hydrochloric acid, and the precipitated solid was filtered off and dried. This gave 475 mg (96% of theory) of 1-(3-chloropyridin-2-yl)-3-(2,2-difluoroethoxy)-1H-pyrazole-5-carboxylic acid.

HPLC-MS: log P=1.59; mass (m/z): 304.1 (M+H)$^+$; $^1$H-NMR (400 MHz, CD$_3$CN, δ, ppm): 4.40 (m, 2H), 6.20 (t, 1H), 6.54 (s, 1H), 7.52 (m, 1H), 8.02 (d, 1H), 8.49 (m, 1H).

The following were obtained analogously:

1-(3-chloropyridin-2-yl)-3-ethoxy-1H-pyrazole-5-carboxylic acid

HPLC-MS: log P=1.47; mass (m/z): 268.0 (M+H)$^{30}$ ; $^1$H-NMR (400 MHz, CD$_3$CN, δ, ppm): 1.36 (t, 3H), 4.22 (m, 2H), 6.47 (s, 1H), 7.50 (m, 1H), 8.00 (d, 1H), 8.47 (m, 1H).

1-(3-chloropyridin-2-yl)-3-isopropoxy-1H-pyrazole-5-carboxylic acid

HPLC-MS: log P=1.76; mass (m/z): 282.0 (M+H)$^+$; $^1$H-NMR (400 MHz, CD$_3$CN, δ, ppm): 1.32 (d, 6H), 4.80 (m, 2H), 6.43 (s, 1H), 7.50 (m, 1H), 8.00 (d, 1H), 8.47 (m, 1H).

1-(3-chloropyridin-2-yl)-3-{[6-(trifluoromethyl)pyridin-3-yl]methoxy}-1H-pyrazole-5-carboxylic acid HPLC-MS: log P=1.59; mass (m/z): 304.1 (M+H)$^+$; $^1$H-NMR (400 MHz, CD$_3$CN, δ, ppm): 5.38 (s, 2H), 6.54 (s, 1H), 7.7-7-8 (m, 2H), 7.9-8.1 (m, 2H), 8.50 (d, 1H), 8.80 (s, 1H).

1-(3-chloropyridin-2-yl)-3-(fluoromethyl)-1H-pyrazole-5-carboxylic acid

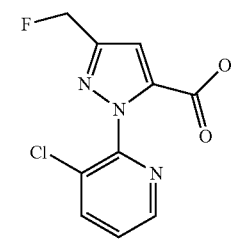 [SMILES: O=C(O)c1cc(CF)nn1-c1ncccc1Cl]

Step 1: Methyl 1-(3-chloropyridin-2-yl)-3-(fluoromethyl)-1H-pyrazole-5-carboxylate 4.00 g (14.9 mmol) of methyl 1-(3-chloropyridin-2-yl)-3-(hydroxymethyl)-1H-pyrazole-5-carboxylate (lit.: DE 102006032168) were initially charged in 60 ml of dichloromethane, and 2.65 g (16.4 mmol) of diethylaminosulfur trifluoride were slowly added dropwise at 0° C. The mixture was then stirred for 18 hours with warming to room temperature. The reaction mixture was poured onto 10% strength sodium bicarbonate solution and extracted with ethyl acetate. The organic phases were dried over magnesium sulfate, the solvent was distilled off under reduced pressure on a rotary evaporator and the crude product was chromatographed on silica gel using cyclohexane/ethyl acetate (1:1). This gave 1.07 g (24% of theory) of methyl 1-(3-chloropyridin-2-yl)-3-(fluoromethyl)-1H-pyrazole-5-carboxylate.

HPLC-MS: log P=1.90; mass (m/z): 270.0 (M+H)$^+$; $^1$H-NMR (400 MHz, CD$_3$CN, δ, ppm): 3.73 (s, 3H), 5.45 (d, 2H), 7.18 (s, 1H), 7.57 (m, 1H), 8.07 (d, 1H), 8.51 (m, 1H).

Step 2: 1-(3-Chloropyridin-2-yl)-3-(fluoromethyl)-1H-pyrazole-5-carboxylic acid 406 mg (1.50 mmol) of methyl 1-(3-chloropyridin-2-yl)-3-(fluoroethoxy)-1H-pyrazole-5-carboxylate were initially charged in 6.4 ml of ethanol, and 288 mg (12.0 mmol) of lithium hydroxide dissolved in 2.1 ml of water were added. The mixture was then stirred at 0° C. for 30 min. The reaction mixture was poured onto water and acidified with dilute hydrochloric acid, and the precipitated solid was filtered off and dried. This gave 250 mg (65% of theory) of 1-(3-chloropyridin-2-yl)-3-(fluoromethyl)-1H-pyrazole-5-carboxylic acid.

HPLC-MS: log P=1.03; mass (m/z): 255.9 (M+H)$^+$; $^1$H-NMR (400 MHz, CD$_3$CN, δ, ppm): 5.44 (d, 2H), 7.17 (s, 1H), 7.55 (m, 1H), 8.04 (d, 1H), 8.50 (m, 1H).

PREPARATION EXAMPLES

The preparation processes described above can be used to give the compounds of the formula (I)—for example the following compounds of the formula (I):

Synthesis Example No. 1

Methyl 2-{2-({[1-(3-chloropyridin-2-yl)-3-(2,2-difluoroethoxy)-1H-pyrazol-5-yl]carbonyl}amino)-5-[(E)-(methoxyimino)methyl]-3-methylbenzoyl}-1-methylhydrazinecarboxylate (Compound No. A-01)

Step 1: 2-Amino-5-formyl-3-methylbenzoic acid (IX-1)

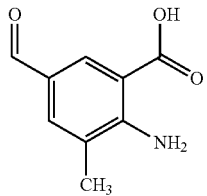

A mixture of 13.4 g (228 mmol) of 2-amino-3-methylbenzoic acid, 10.3 g (125 mmol) of paraformaldehyde, 35.1 g (250 mmol) of hexamethylenetetramine and 28.5 ml of glacial acetic acid were stirred at 100° C. for 2 hours. The mixture was then diluted with 75 ml of hot water, 58 ml of 37% strength hydrochloric acid were added carefully and the mixture was then stirred at 90° C. for a further 10 minutes. After cooling, the pH was adjusted to 4 using aqueous sodium hydroxide solution with ice cooling, resulting in the precipitation of the product, which was filtered off. The crude product was triturated with hot acetonitrile, filtered off with suction and dried. This gave 13.8 g (32.8% of theory) of 2-amino-5-formyl-4-methylbenzoic acid.

HPLC-MS: log P=1.02; mass (m/z): 180.0 (M+H)$^+$; $^1$H-NMR (400 MHz, CD$_3$CN, δ, ppm): 2.15 (s, 3H), 3.85 (s, 3H), 6.8-6.9 (br s, 2H), 7.69 (s, 1H), 8.23 (s, 1H), 9.68 (s, 1H).

Step 2: 2-Amino-5-[(E)-(methoxyimino)methyl]-3-methylbenzoic acid (VIII-1)

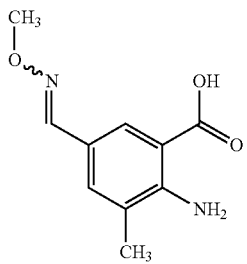

4.87 g (58.3 mmol) of O-methylhydroxylamine hydrochloride were initially charged in 20 ml of pyridine, and a solution of 10 g (53.0 mmol) of 2-amino-5-formyl-3-methylbenzoic acid in 50 ml of pyridine was added. The mixture was then heated at 70° C. for 18 hours. After cooling, the reaction mixture was poured onto water and extracted with ethyl acetate. The organic phase was dried over magnesium sulfate and the solvent was distilled off on a rotary evaporator under reduced pressure. The crude product was recrystallized from isopropanol, giving 7.50 g (63% of theory) of 2-amino-5-[(E)-(methoxyimino)methyl]-3-methylbenzoic acid.

HPLC-MS: log P=1.73; mass (m/z): 209.0 (M+H)$^+$; $^1$H-NMR (400 MHz, CD$_3$CN, δ, ppm): 2.15 (s, 3H), 3.85 (s, 3H), 6.4-6.5 (br s, 2H), 7.52 (s, 1H), 7.84 (s, 1H), 7.95 (s, 1H).

Step 3: 2-[1-(3-Chloropyridin-2-yl)-3-(2,2-difluoroethoxy)-1H-pyrazol-5-yl]-8-methyl-4-oxo-4H-3,1-benzoxazine-6-carbaldehyde O-methyl oxime

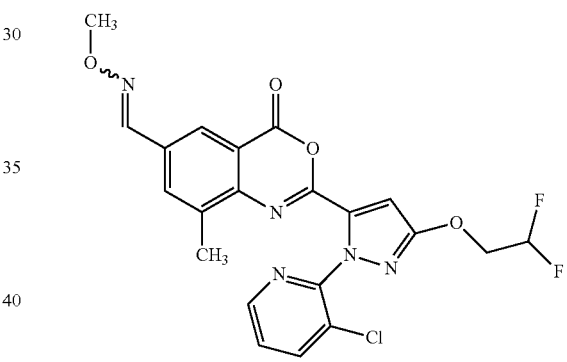

0.980 g (3.13 mmol) of methansulfonyl chloride was initially charged in 25 ml of acetonitrile and cooled to −5° C. A solution of 1.9 g (6.25 mmol) of 1-(3-chloropyridin-2-yl)-3-(2,2-difluoroethoxy)-1H-pyrazole-5-carboxylic acid and 1.2 g of 2.6-dimethylpyridine in 30 ml of acetenitrile was then added dropwise. After 15 min of stirring at 0° C., a mixture of 1.3 g (6.25 mmol) of 2-amino-5-[(E)-(methoxyimino)methyl]-3-methylbenzoic acid was added a little at a time, and the mixture was stirred for another 15 min at 0° C. Another 0.980 g (3.13 mmol) of methanesulfonyl chloride in 15 ml of acetonitrile were then added dropwise and stirring was continued for 18 hours with warming to room temperature. The reaction mixture was poured onto water, resulting in the precipitation of the desired product. Drying at room temperature gave 2.34 g (79% of theory) of 2-[1-(3-chloropyridin-2-yl)-3-(2,2-difluoroethoxy)-1H-pyrazol-5-yl]-8-methyl-4-oxo-4H-3,1-benzoxazine-6-carbaldehyde O-methyl oxime.

HPLC-MS: log P=3.92; mass (m/z): 476.1 (M+H)$^+$; $^1$H-NMR (400 MHz, CD$_3$CN, δ, ppm): 2.14 (s, 3H), 3.94 (s, 3H), 4.50 (m, 2H), 6.23 (m, 1H), 6.78 (s, 1H), 7.57 (m, 1H), 7.86 (s, 1H), 8.0-8.2 (m, 3H) 8.55 (m, 1H).

Step 4: Methyl 2-{2-({[1-(3-chloropyridin-2-yl)-3-(2,2-difluoroethoxy)-1H-pyrazol-5-yl]carbonyl}amino)-5-[(E)-(methoxyimino)methyl]-3-methylbenzoyl}-1-methylhydrazinecarboxylate

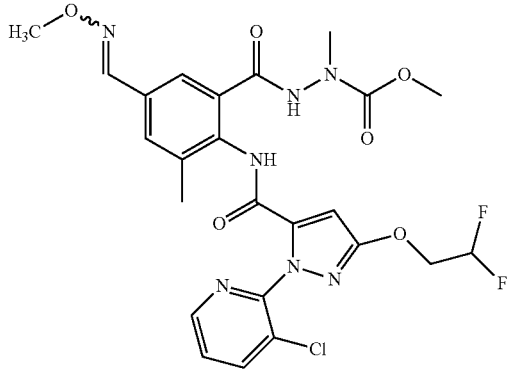 [SMILES: CON=Cc1cc(C)c(NC(=O)c2cc(OCC(F)F)nn2-c2ncccc2Cl)c(C(=O)NN(C)C(=O)OC)c1]

80.0 mg (0.16 mmol) of 2-[1-(3-chloropyridin-2-yl)-3-(2,2-difluoroethoxy)-1H-pyrazol-5-yl]-8-methyl-4-oxo-4H-3,1-benzoxazine-6-carbaldehyde O-methyl oxime were initially charged in 4.8 ml of tetrahydrofuran, and 700 mg (6.72 mmol) of methyl 1-methylhydrazinecarboxylate were added. After 18 hours of stirring at reflux temperature, the reaction mixture was cooled and poured onto water. The precipitated product was filtered off, dried and recrystallized from isopropanol. This gave 10.0 g (10% of theory) of methyl 2-{2-({[1-(3-chloropyridin-2-yl)-3-(2,2-difluoroethoxy)-1H-pyrazol-5-yl]carbonyl}amino)-5-[(E)-(methoxyimino)methyl]-3-methylbenzoyl}-1-methylhydrazinecarboxylate.

HPLC-MS: log P=2.58; mass (m/z): 580.1 (M+H)$^+$;
$^1$H-NMR (400 MHz, CD$_3$CN, δ, ppm): 2.22 (s, 3H), 3.08 (s, 3H), 3.55 (m, 3H), 3.93 (s, 3H), 4.47 (m, 2H), 6.23 (m, 1H), 6.60 (s, 1H), 7.45 (m, 1H), 7.62 (s, 1H), 7.07 (d, 1H), 8.10 (s, 1H), 8.43 (d, 1H), 8.84 (br. s, 1H), 9.20 (br. S, 1H).

Synthesis Example No. 2

Methyl 2-{2-({[1-(3-chloropyridin-2-yl)-3-(difluoromethoxy)-1H-pyrazol-5-yl]carbonyl}amino)-5-[(E)-(methoxyimino)methyl]-3-methylbenzoyl}hydrazinecarboxylate (Compound No. A-02)

Step 1: 2-[1-(3-Chloropyridin-2-yl)-3-(difluoromethoxy)-1H-pyrazol-5-yl]-8-methyl-4-oxo-4H-3,1-benzoxazine-6-carbaldehyde O-methyl oxime

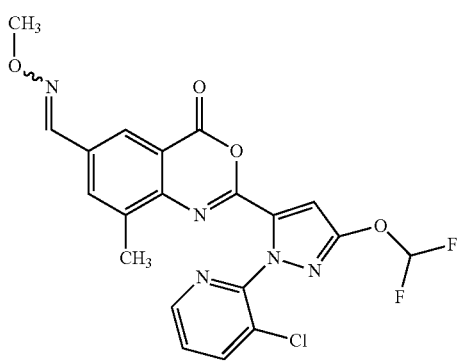 [SMILES: CON=Cc1cc(C)c2nc(-c3cc(OC(F)F)nn3-c3ncccc3Cl)oc(=O)c2c1]

Synthesis analogously to Synthesis Example 1, Step 3 from 393 mg (1.35 mmol) of 1-(3-chloropyridin-2-yl)-3-(2,2-difluoromethoxy)-1H-pyrazole-5-carboxylic acid and 283 mg (1.35 mmol) of 2-amino-5-[(E)-(methoxyimino)methyl]-3-methylbenzoic acid gave 494 mg (78% of theory) of 2-[1-(3-chloropyridin-2-yl)-3-(difluoromethoxy)-1H-pyrazol-5-yl]-8-methyl-4-oxo-4H-3,1-benzoxazine-6-carbaldehyde O-methyl oxime.

HPLC-MS: log P=3.93; mass (m/z): 462.0 (M+H)$^+$;
$^1$H-NMR (400 MHz, CD$_3$CN, δ, ppm): 2.11 (s, 3H), 3.94 (s, 3H), 6.96 (s, 1H), 7.01 (s, 1H), 7.27 (s, 1H), 7.59-7.63 (m, 1H), 7.88 (s, 1H), 8.0-8.2 (m, 3H) 8.56 (m, 1H).

Step 2: 1-(3-Chloropyridin-2-yl)-3-(difluoromethoxy)-N-{2-(hydrazinocarbonyl)-4-[(E)-(methoxyimino)methyl]-6-methylphenyl}-1H-pyrazole-5-carboxamide

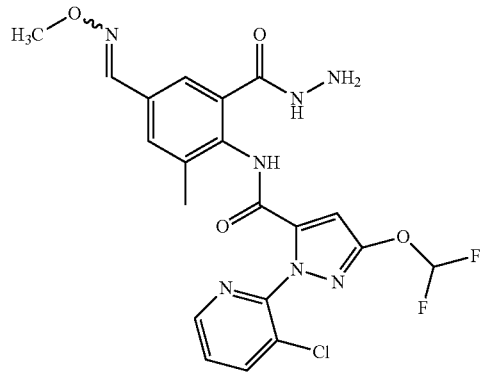 [SMILES: CON=Cc1cc(C)c(NC(=O)c2cc(OC(F)F)nn2-c2ncccc2Cl)c(C(=O)NN)c1]

Synthesis analogously to Synthesis Example 1, Step 4 from 100 mg (0.21 mmol) of 2-[1-(3-chloropyridin-2-yl)-3-(difluoromethoxy)-1H-pyrazol-5-yl]-8-methyl-4-oxo-4H-3,1-benzoxazine-6-carbaldehyde O-methyl oxime and 13.5 mg (0.21 mmol) of hydrazine hydrate gave 84.0 mg (65% of theory) of 1-(3-chloropyridin-2-yl)-3-(difluoromethoxy)-N-{2-(hydrazinocarbonyl)-4-[(E)-(methoxyimino)methyl]-6-methylphenyl}-1H-pyrazole-5-carboxamide.

HPLC-MS: log P=2.12; mass (m/z): 494.1 (M+H)$^+$;
$^1$H-NMR (400 MHz, CD$_3$CN, δ, ppm): 2.11 (s, 3H), 3.92 (s, 3H), 5.21 (s, 1H), 6.23 (m, 1H), 6.60 (s, 1H), 7.45-7.56 (m, 3H), 7.90-8.10 (m, 3H), 8.19 (br. S, 1H), 8.47 (d, 1H).

Step 3: Methyl 2-{2-({[1-(3-chloropyridin-2-yl)-3-(difluoromethoxy)-1H-pyrazol-5-yl]carbonyl}amino)-5-[(E)-(methoxyimino)methyl]-3-methylbenzoyl}hydrazinecarboxylate

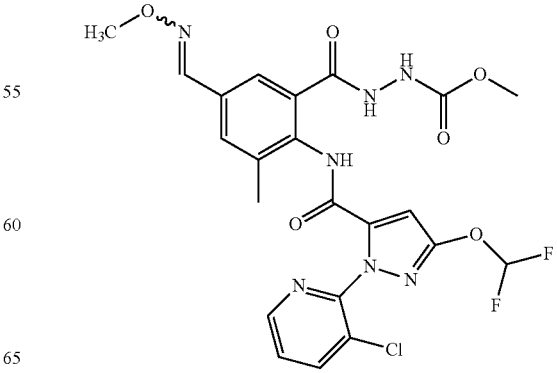

64.0 mg (0.13 mmol) of 1-(3-chloropyridin-2-yl)-3-(difluoromethoxy)-N-{2-(hydrazinocarbonyl)-4-[(E)-(methoxyimino)methyl]-6-methylphenyl}-1H-pyrazole-5-carboxamide were initially charged in 8 ml of pyridine, and 13.9 mg (0.14 mmol) of methyl chloroformate were added. The reaction mixture was stirred at reflux temperature for 18 hours and then poured onto water and extracted with ethyl acetate. The organic phase was dried and concentrated. The residue was recrystallized from isopropanol, giving 43.0 mg (82% of theory):methyl 2-{2-({[1-(3-chloropyridin-2-yl)-3-(difluoromethoxy)-1H-pyrazol-5-yl]carbonyl}amino)-5-[(E)-(methoxyimino)methyl]-3-methylbenzoyl}hydrazinecarboxylate.

HPLC-MS: log P=2.28; mass (m/z): 552.1 (M+H)$^+$; $^1$H-NMR (400 MHz, CD$_3$CN, δ, ppm): 2.12 (s, 3H), 3.68 (br. s, 3H), 3.95 (s, 3H), 5.21 (s, 1H), 6.80 (s, 1H), 7.01 (s, 1H), 7.45-7.51 (m, 1H), 7.65 (d, 1H), 7.98 (d, 1H), 8.07 (s, 1H), 8.46 (d, 1H), 8.61 (br. s, 1H), 9.33 (br. S, 1H).

The examples below in Tables A to C can be obtained in an analogous manner:

TABLE A[#)]

(I-A)

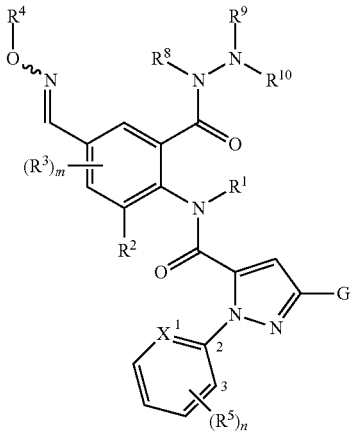

where R$^1$ and (R$^3$)$_m$ represent H, R$^2$ and R$^4$ represent CH$_3$, X represents N and (R$^5$)$_n$ represents 3-Cl and G, R$^8$, R$^9$ and R$^{10}$ have the meaning given in Table A.

| No. | G | R$^8$ | R$^9$ | R$^{10}$ | (M + H)$^{+\,a)}$ | log p $^{a)}$ |
|---|---|---|---|---|---|---|
| A-01 | OCH$_2$CHF$_2$ | H | Me | —C(O)0Me | 580.1 | 2.58 |
| A-02 | OCHF$_2$ | H | H | —C(O)OMe | 552.1 | 2.38 |
| A-03 | Br | Me | H | —C(O)OMe | 578.1 | 2.74 |
| A-04 | CF$_3$ | H | H | —C(O)OMe | 553.2 | 2.65 |
| A-05 | Br | Me | H | —C(O)OPh | 640.1 | 3.46 |
| A-06 | Br | H | H | —C(O)OiPr | 592.0 | 2.88 |
| A-07 | Br | Me | H | —C(O)OCH$_2$CH═CH | 604.1 | 3.12 |
| A-08 | Br | H | H | —C(O)OCH$_2$C≡CH | 587.9 | 2.58 |
| A-09 | Br | H | H | —S(O)$_2$Me | 584.1 | 2.30 |
| A-10 | Br | Me | H | —C(O)OEt | 592.0 | 2.97 |
| A-11 | Br | —C(O)Me | H | —C(O)Me | 590.1 | 2.67 |
| A-12 | Br | —S(O)$_2$Me | H | —S(O)$_2$Me | 662.1 | 2.99 |
| A-13 | Br | Me | H | —C(O)O(CH$_2$)$_2$OMe | 622.1 | 2.72 |
| A-14 | Br | Me | H | —C(O)Me | 562.1 | 2.31 |
| A-15 | Br | H | H | —C(O)OPh | 626.1 | 3.03 |
| A-16 | Br | Me | H | —C(O)OiPr | 606.1 | 3.28 |
| A-17 | CF$_3$ | H | H | —C(O)OEt | 568.0 | 2.92 |
| A-18 | CF$_3$ | H | H | —C(O)OiPr | 582.1 | 3.17 |
| A-19 | CF$_3$ | H | H | —C(O)OPh | 616.1 | 3.02 |
| A-20 | CF$_3$ | H | H | —C(O)O(CH$_2$)$_2$OMe | 598.1 | 2.74 |
| A-21 | CF$_3$ | H | H | —C(O)OCH$_2$CH═CH | 580.1 | 3.04 |
| A-22 | CF$_3$ | H | H | —C(O)OCH$_2$C≡CH | 578.1 | 2.86 |
| A-23 | CF$_3$ | H | H | —S(O)$_2$Me | 574.1 | 2.63 |
| A-24 | CF$_3$ | Me | H | —C(O)OEt | 582.1 | 3.31 |
| A-25 | CF$_3$ | Me | H | —C(O)OiPr | 596.1 | 3.57 |
| A-26 | CF$_3$ | Me | H | —C(O)OPh | 630.1 | 3.72 |
| A-27 | CF$_3$ | Me | H | —C(O)O(CH$_2$)$_2$OMe | 612.1 | 3.05 |
| A-28 | CF$_3$ | Me | H | —C(O)OCH$_2$CH═CH | 594.1 | 3.41 |
| A-29 | CF$_3$ | Me | H | —C(O)OCH$_2$C≡CH | 592.1 | 3.16 |
| A-30 | CF$_3$ | Me | H | —C(O)Me | 552.1 | 2.75 |
| A-31 | CF$_3$ | Me | H | —S(O)$_2$Me | 588.1 | 2.88 |
| A-32 | CF$_3$ | H | H | —C(O)Me | 538.1 | 2.38 |
| A-33 | OCH$_2$CF$_3$ | H | H | —C(O)OMe | 584.1 | 2.70 |
| A-34 | OEt | H | H | —C(O)OMe | 530.1 | 2.26 |
| A-35 | OiPr | H | H | —C(O)OMe | 544.1 | 2.54 |

TABLE A#)-continued

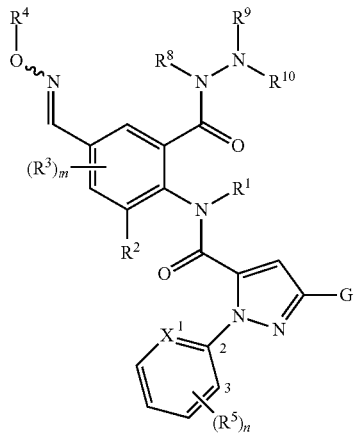

(I-A)

where R¹ and (R³)ₘ represent H, R² and R⁴ represent CH₃, X represents N and (R⁵)ₙ represents 3-Cl and G, R⁸, R⁹ and R¹⁰ have the meaning given in Table A.

| No. | G | R⁸ | R⁹ | R¹⁰ | (M + H)⁺ ᵃ⁾ | log p ᵃ⁾ |
|---|---|---|---|---|---|---|
| A-36 | (pyridine-CF₃ group with OCH₂) | H | H | —C(O)OMe | 661.1 | 2.87 |
| A-37 | OCH₂CHF₂ | H | H | —C(O)OMe | 566.1 | 2.37 |
| A-38 | OMe | H | H | —C(O)OMe | 516.1 | 2.00 |
| A-39 | CHF₂ | H | H | —C(O)OMe | 536.1 | 2.26 |
| A-40 | OMe | H | H | —C(O)OMe | 515.1 | 2.45 |
| A-41 | CHF₂ | H | Me | —C(O)OMe | 549.9 | 2.46 |
| A-42 | Br | H | H | —C(O)OMe | 565.1 | 2.38 |
| A-43 | OMe | H | Me | —C(O)OMe | 530.2 | 2.19 |
| A-44 | CH₂F | H | H | —C(O)OMe | 517.9 | 2.02 |
| A-45 | Br | H | Me | —C(O)OMe | 580.0 | 2.50 |
| A-46 | CF₃ | H | Me | —C(O)OMe | 568.1 | 2.85 |
| A-47 | CHF₂ | H | Me | —C(O)OMe | 532.1 | 2.21 |
| A-48 | CF₃ | Me | H | —C(O)OMe | 568.1 | 3.00 |
| A-49 | OCHF₂ | H | Me | —C(O)OMe | 566.2 | 2.60 |

Abbreviations: Me = methyl, Et = ethyl, iPr = isopropyl

TABLE B #)

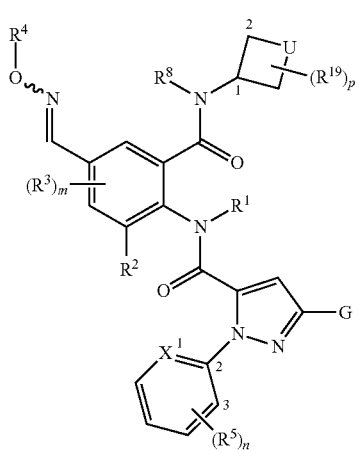

(I-B)

where R¹, R⁶ and (R³)ₘ represent H, R² and R⁴ represent CH₃, X represents N, and (R⁵)ₙ represents 3-Cl and G, U and (R¹⁹)ₚ have the meaning given in Table B.

TABLE B #)-continued

| No. | G | U | (R¹⁹)ₚ | (M + H)⁺ ᵃ⁾ | log p ᵃ⁾ |
|---|---|---|---|---|---|
| B-01 | Br | S | 1-Me | 578.1 | 3.22 |
| B-02 | CF₃ | O | H | 537.0 | 2.78 |
| B-03 | Br | O | H | 547.1 | 2.44 |
| B-04 | CF₃ | SO₂ | H | 585.1 | 2.78 |
| B-05 | CF₃ | SO | H | 569.0 | 2.51 |
| B-06 | CF₃ | S | H | 553.1 | 3.46 |
| B-07 | OiPr | O | H | 527.1 | 2.57 |
| B-08 | 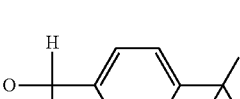 | O | H | 645.1 | 2.97 |
| B-09 | OCH₂CHF₂ | O | H | 549.1 | 2.44 |
| B-10 | OMe | O | H | 499.1 | 2.04 |
| B-11 | CHF₂ | O | H | 519.1 | 2.31 |
| B-12 | CH₂F | O | H | 500.9 | 2.04 |

Abbreviations: Me = methyl

TABLE C #)

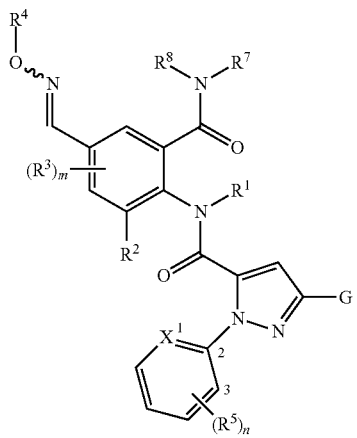

(I-C)

where $R^1$ and $(R_3)_m$ represent H, $R^2$ represents $CH_3$, X represents N and $(R^5)_n$ represents 3-Cl and $R^4$, $R^6$, $R^7$ and G have the meaning given in Table C.

| No. | G | $R^4$ | $R^6$ | $R^7$ | $(M+H)^{+ a)}$ | log p $^{a)}$ |
|---|---|---|---|---|---|---|
| C-01 | CH₂-tetrazole-CF₃ | Me | H | tBu | 619.1 | 3.74 |
| C-02 | CH₂-tetrazole-CF₃ | Me | H | Me | 577.1 | 2.94 |
| C-03 | CH₂-tetrazole-CF₃ | iPr | H | tBu | 648.1 | 4.38 |
| C-04 | CH₂-tetrazole-CF₃ | Et | H | tBu | 634.1 | 4.04 |
| C-05 | $CF_3$ | Me | H | $CH(Me)CH_2SMe$ | 569.1 | 3.72 |
| C-06 | OiPr | Me | H | cPr | 511.1 | 2.98 |
| C-07 | OiPr | Me | H | iPr | 513.1 | 3.29 |
| C-08 | OiPr | Me | H | CH(Me)cPr | 540.1 | 3.65 |
| C-09 | OiPr | Me | H | tBu | 528.1 | 3.74 |
| C-10 | OEt | Me | H | Me | 471.1 | 2.48 |
| C-11 | OEt | Me | H | tBu | 513.2 | 3.42 |
| C-12 | O-CH₂-(6-CF₃-pyridin-3-yl) | Me | H | Me | 602.2 | 3.05 |
| C-13 | O-CH₂-(6-CF₃-pyridin-3-yl) | Me | H | tBu | 645.1 | 3.96 |

TABLE C #)-continued (I-C)

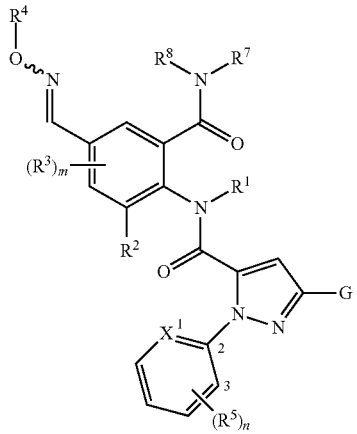

where $R^1$ and $(R_3)_m$ represent H, $R^2$ represents $CH_3$, X represents N and $(R^5)_n$ represents 3-Cl and $R^4$, $R^6$, $R^7$ and G have the meaning given in Table C.

| No. | G | $R^4$ | $R^6$ | $R^7$ | $(M+H)^{+\ a)}$ | log p $^{a)}$ |
|---|---|---|---|---|---|---|
| C-14 | ![5-(trifluoromethyl)pyridin-2-yl-methyloxy] | Me | H | CH(Me)cPr | 657.1 | 3.92 |
| C-15 | ![5-(trifluoromethyl)pyridin-2-yl-methyloxy] | Me | H | iPr | 631.1 | 3.61 |
| C-16 | ![5-(trifluoromethyl)pyridin-2-yl-methyloxy] | Me | H | cPr | 629.1 | 3.35 |
| C-17 | OCH$_2$CHF$_2$ | Me | H | cPr | 533.9 | 2.91 |
| C-18 | OCH$_2$CHF$_2$ | Me | H | CH(Me)cPr | 561.2 | 3.39 |
| C-19 | OCH$_2$CHF$_2$ | Me | H | iPr | 535.1 | 3.07 |
| C-20 | OCH$_2$CHF$_2$ | Me | H | Me | 507.1 | 2.57 |
| C-21 | OCH$_2$CHF$_2$ | Me | H | tBu | 549.1 | 3.43 |
| C-22 | OMe | Me | H | Me | 457.1 | 2.15 |
| C-23 | OMe | Me | H | cPr | 483.1 | 2.40 |
| C-24 | OMe | Me | H | iPr | 485.1 | 2.65 |
| C-25 | OMe | Me | H | CH(Me)cPr | 511.1 | 3.02 |
| C-26 | OMe | Me | H | tBu | 499.1 | 3.06 |
| C-27 | OEt | Me | H | CH(Me)cPr | 525.1 | 3.38 |
| C-28 | CHF$_2$ | Me | H | Me | 477.1 | 2.48 |
| C-29 | CHF$_2$ | Me | H | iPr | 504.2 | 2.98 |
| C-30 | OMe | Me | H | cPr | 482.1 | 2.97 |
| C-31 | OMe | Me | H | CH(Me)cPr | 510.1 | 3.66 |
| C-32 | OMe | Me | H | iPr | 484.1 | 3.22 |
| C-33 | OMe | Me | H | Me | 456.1 | 2.70 |
| C-34 | CHF$_2$ | Me | H | cPr | 503.1 | 2.72 |
| C-35 | CHF$_2$ | Me | H | tBu | 519.2 | 3.34 |
| C-36 | CHF$_2$ | Me | H | CH(Me)cPr | 531.3 | 3.29 |
| C-37 | OMe | Me | H | tBu | 498.1 | 3.71 |
| C-38 | OCH$_2$CHF$_2$ | Me | Me | Me | 521.1 | 2.61 |
| C-39 | OCH$_2$CHF$_2$ | Me | H | CH(Me)CH$_2$OMe | 565.2 | 2.93 |
| C-40 | OMe | Me | Me | Me | 471.1 | 2.16 |
| C-41 | OMe | Me | H | CH(Me)CH$_2$OMe | 515.3 | 2.51 |
| C-42 | CH$_2$F | Me | H | cPr | 485.1 | 2.38 |
| C-43 | CH$_2$F | Me | H | CH(Me)cPr | 513.1 | 2.96 |
| C-44 | CH$_2$F | Me | H | tBu | 501.1 | 3.00 |
| C-45 | CH$_2$F | Me | H | Me | 459.2 | 2.14 |
| C-46 | OCH$_2$CHF$_2$ | Me | H | Et | 521.2 | 2.81 |
| C-47 | OMe | Me | H | Et | 471.1 | 2.41 |
| C-48 | OMe | Me | H | CH$_2$C≡CH | 481.2 | 2.40 |
| C-49 | CH$_2$F | Me | H | iPr | 487.1 | 2.65 |

TABLE C #)-continued

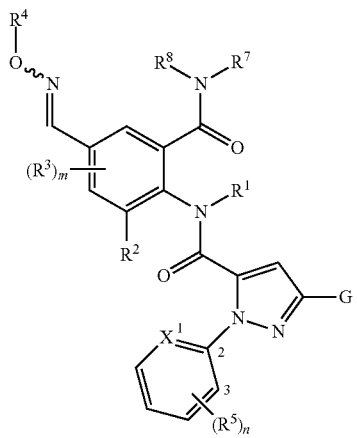

(I-C)

where R¹ and (R₃)ₘ represent H, R² represents CH₃, X represents N and (R⁵)ₙ represents 3-Cl and R⁴, R⁶, R⁷ and G have the meaning given in Table C.

| No. | G | R⁴ | R⁶ | R⁷ | (M + H)⁺ ᵃ⁾ | log p ᵃ⁾ |
|---|---|---|---|---|---|---|
| C-50 | OCH₂CHF₂ | Me | H | CH₂-(2-pyridyl) | 584.1 | 2.19 |
| C-51 | OMe | Me | H | CH₂-(2-pyridyl) | 534.1 | 1.81 |
| C-52 | OCH₂CHF₂ | Me | H | CH₂C≡CH | 531.2 | 2.78 |
| C-53 | CH₂F | Me | H | Et | 473.1 | 2.39 |
| C-54 | CH₂F | Me | H | CH(Me)CH₂OMe | 517.1 | 2.47 |
| C-55 | CH₂F | Me | Me | Me | 473.1 | 2.19 |
| C-56 | CH₂F | Me | H | CH₂CH₂OMe | 503.1 | 2.27 |
| C-57 | CH₂F | Me | H | CH₂C≡CH | 483.2 | 2.38 |
| C-58 | CHF₂ | Me | H | CH₂-(2-pyridyl) | 554.1 | 1.68 |
| C-59 | CHF₂ | Me | H | CH₂CH₂OMe | 521.2 | 2.53 |
| C-60 | CHF₂ | Me | H | CH(Me)CH₂OMe | 535.1 | 2.84 |
| C-61 | CHF₂ | Me | Me | Me | 491.1 | 2.47 |
| C-62 | CHF₂ | Me | H | CH₂C≡CH | 501.2 | 2.69 |
| C-63 | CHF₂ | Me | H | Et | 491.1 | 2.71 |
| C-64 | CHF₂ | Me | H | CH₂-(2-pyridyl) | 553.1 | |
| C-65 | OiPr | Me | H | Me | 485.2 | 2.75 |

Abbreviations: Me = methyl, Et = ethyl, iPr = isopropyl, cPr = cyclopropyl, tBu = tertiary butyl

) The alkoximino compounds listed in Tables A, B and C are generally present as mixtures of the E and the Z isomer at the alkoximino function. Here, the E isomer forms the main component (>90%) and the Z isomer the minor component (<10%). Unless indicated otherwise, the given data refer to the E isomer.

a) The determination of the M⁺ by LC-MS in the acidic range is effected at pH 2.7, acetonitrile (contains 0.1% formic acid) and water as eluents; linear gradient from 10% acetonitrile to 95% acetonitrile, instrument: Agilent 1100 LC system, Agilent MSD system, HTS PAL.

The log P values reported in the tables and Preparation Examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the log P values are known.

| 1H NMR data[b] |
| --- |

Compound No. A-01,
see Synthesis Example No. 1
Compound No. A-02,
see Synthesis Example No. 2
Compound No. A-03, solvent: [CD3CN],
9.024 (0.51); 8.4837 (1.59); 8.48 (1.7); 8.4719 (1.76); 8.4683 (1.69); 8.0875 (0.35); 8.0331 (5.3); 8.0134 (1.37); 8.0105 (1.38); 7.8714 (0.7); 7.5397 (1.41); 7.5279 (1.36); 7.5195 (1.42); 7.5076 (1.59); 7.4979 (2.28); 7.4257 (0.38); 7.4195 (0.39); 7.3092 (1.31); 7.1717 (0.46); 7.1653 (0.53); 7.1518 (4.25); 4.0854 (1.09); 4.0676 (3.19); 4.0497 (3.24); 4.0319 (1.1); 3.9431 (0.34); 3.9354 (1.33); 3.9227 (1.61); 3.9106 (16); 3.5639 (4.44); 3.1516 (4.55); 3.0805 (0.38); 2.9577 (0.34); 2.8217 (0.38); 2.8097 (0.35); 2.2305 (1.23); 2.209 (5.73); 2.1885 (1.04); 2.1513 (142.72); 2.1201 (0.62); 2.1139 (0.73); 2.1077 (0.85); 2.1015 (0.63); 2.0953 (0.34); 1.972 (15.18); 1.9646 (4.25); 1.9583 (6.29); 1.9526 (48.81); 1.9465 (91.2); 1.9403 (127.15); 1.9341 (87.58); 1.9279 (44.96); 1.7749 (0.53); 1.7687 (0.75); 1.7626 (0.52); 1.3717 (7.76); 1.3402 (0.46); 1.2849 (0.98); 1.2765 (8.93); 1.2215 (4.12); 1.2037 (8.06); 1.1858 (4); 0.1459 (0.83); 0.008 (8.74); −0.0002 (203.53); −0.0086 (8.52); −0.1496 (0.84)
Compound No. A-04, solvent: [DMSO],
10.397 (2.78); 10.1569 (2.99); 9.2812 (0.78); 8.5449 (2.05); 8.5412 (2.22); 8.5331 (2.23); 8.5295 (2.16); 8.2519 (5.43); 8.2392 (2.01); 8.2356 (1.96); 8.2189 (2.04); 8.2153 (1.93); 7.7245 (3.53); 7.6822 (2.07); 7.6704 (2.18); 7.6619 (2.49); 7.6501 (2.79); 7.6326 (2.71); 3.944 (0.75); 3.9145 (16); 3.6222 (2.61); 3.4601 (0.39); 3.4148 (0.41); 3.4045 (0.39); 3.3404 (35.16); 2.6749 (0.79); 2.6707 (1.05); 2.6664 (0.82); 2.5062 (118.09); 2.5017 (151.83); 2.4973 (114.91); 2.3329 (0.84); 2.3285 (1.11); 2.3241 (0.85); 2.1718 (9.78); 0.1459 (0.32); 0.0078 (4.08); −0.0002 (76.61); −0.1496 (0.35)
Compound No. A-05, solvent: [CD3CN],
8.4944 (1.2); 8.4849 (1.31); 8.4526 (0.38); 8.076 (4.25); 8.042 (1.14); 8.0186 (1.29); 7.5861 (1.11); 7.5681 (1.47); 7.5466 (1.14); 7.5344 (1.29); 7.5263 (1.24); 7.5143 (1.16); 7.4932 (2.34); 7.4727 (4.92); 7.4537 (3.78); 7.4089 (1.87); 7.3515 (2.34); 7.3298 (6.58); 7.327 (5.85); 7.3078 (4.52); 7.2501 (0.8); 7.2331 (0.95); 7.2219 (0.76); 7.2038 (1.1); 7.1826 (0.99); 7.1649 (1.31); 6.9943 (0.36); 6.8985 (0.36); 6.8636 (1.74); 6.845 (1.78); 6.8064 (0.93); 6.787 (0.86); 4.2719 (0.39); 4.2541 (0.33); 3.9212 (16); 3.8884 (0.36); 3.239 (0.52); 3.1927 (5.89); 2.4644 (1.09); 2.4594 (0.78); 2.2649 (6.18); 2.2296 (1.24); 2.1535 (1297.42); 2.1203 (5.11); 2.1141 (5.81); 2.1078 (6.49); 2.1017 (4.59); 2.0955 (2.67); 1.9646 (14.52); 1.9528 (319.99); 1.9467 (608.75); 1.9405 (868.35); 1.9343 (598.94); 1.9282 (308.23); 1.7813 (1.98); 1.7751 (3.71); 1.7689 (5.27); 1.7628 (3.6); 1.7565 (1.94); 1.7202 (0.46); 1.346 (0.5); 1.3281 (0.71); 1.3107 (0.48); 1.269 (0.96); 1.2542 (0.5); 0.1459 (5.26); 0.0783 (0.37); 0.0078 (45.59); −0.0002 (1133.78); −0.0085 (43.79); −0.1496 (5.3)
Compound No. A-06, solvent: [CD3CN],
8.4773 (1.43); 8.4736 (1.46); 8.4656 (1.49); 8.4618 (1.41); 8.368 (0.51); 8.3641 (0.56); 8.3562 (0.55); 8.3524 (0.56); 8.1595 (1.66); 8.0891 (4.46); 8.0183 (1.34); 8.0146 (1.34); 8.0103 (0.77); 8.0065 (0.71); 7.9981 (1.5); 7.9944 (1.51); 7.9902 (0.8); 7.9863 (0.67); 7.8248 (0.67); 7.6452 (1.91); 7.6075 (2.04); 7.529 (1.49); 7.5171 (1.53); 7.5088 (1.45); 7.497 (1.38); 7.4736 (0.65); 7.4619 (0.64); 7.4534 (0.62); 7.4416 (0.6); 7.3677 (2.05); 7.1627 (2.08); 5.2074 (1.97); 4.9053 (0.49); 4.8894 (0.65); 4.8739 (0.5); 4.0856 (0.34); 4.0678 (0.99); 4.05 (1.02); 4.0321 (0.33); 3.9795 (0.55); 3.9509 (0.53); 3.9371 (7.81); 3.9327 (16); 3.9236 (1.06); 3.9101 (0.44); 2.47 (0.39); 2.4652 (0.54); 2.4605 (0.39); 2.4424 (0.42); 2.3281 (1.21); 2.2959 (0.47); 2.2873 (0.42); 2.2113 (13.51); 2.176 (102.32); 2.1208 (1.39); 2.1146 (1.39); 2.1084 (1.44); 2.1021 (1.11); 2.0961 (0.8); 1.9724 (4.94); 1.9651 (2.19); 1.9533 (44.55); 1.9471 (84.59); 1.941 (119.43); 1.9348 (82.08); 1.9286 (42.09); 1.9196 (4.9); 1.7819 (0.35); 1.7756 (0.52); 1.7694 (0.76); 1.7632 (0.53); 1.285 (0.71); 1.2414 (2.77); 1.2216 (2.54); 1.2038 (2.97); 1.186 (1.49); 0.1461 (0.64); 0.008 (6.2); −0.0002 (143.99); −0.0085 (4.98); −0.1494 (0.61)
Compound No. A-07, solvent: [CD3CN],
9.056 (0.58); 8.4847 (1.48); 8.4816 (1.57); 8.4731 (1.59); 8.47 (1.61); 8.0275 (4.97); 8.0134 (2.08); 7.5387 (1.37); 7.5269 (1.44); 7.5186 (1.47); 7.5062 (2.94); 7.3095 (1.6); 7.2727 (0.68); 7.2601 (0.6); 7.2359 (0.33); 7.1983 (0.32); 7.1818 (0.52); 7.1758 (0.57); 7.1467 (2.54); 7.1038 (0.33); 7.022 (0.37); 5.7469 (0.33); 5.7311 (0.34); 5.0778 (0.77); 5.0518 (0.7); 5.0159 (0.69); 4.971 (0.62); 4.4805 (1.21); 4.0857 (0.33); 4.0682 (0.95); 4.0504 (0.98); 4.0325 (0.33); 3.934 (16); 3.5508 (0.45); 3.1575 (6.1); 3.1127 (0.36); 2.4693 (0.4); 2.4646 (0.55); 2.4614 (0.39); 2.2465 (0.53); 2.2047 (6.45); 2.1617 (321.98); 2.1216 (1.45); 2.1142 (1.54); 2.1079 (1.74); 2.1018 (1.31); 2.0968 (0.88); 1.9724 (4.73); 1.9529 (75.91); 1.9477 (130.14); 1.9468 (144.27); 1.9415 (185.06); 1.9406 (203.78); 1.9354 (130.16); 1.9344 (141.77); 1.9294 (69.46); 1.9282 (73.1); 1.7813 (0.79); 1.7752 (1.17); 1.769 (1.52); 1.7628 (1.15); 1.7569 (0.76); 1.7472 (0.53); 1.7301 (0.55); 1.6632 (0.44); 1.6056 (0.61); 1.5982 (0.89); 1.5812 (1.31); 1.5717 (0.9); 1.5649 (1.15); 1.5535 (0.84); 1.544 (0.67); 1.5262 (0.62); 1.5153 (0.53); 1.4954 (0.49); 1.4775 (0.51); 1.4449 (0.46); 1.3863 (0.65); 1.3721 (0.77); 1.3407 (1.35); 1.2852 (2.47); 1.2696 (5.43); 1.2514 (1.58); 1.2389 (1); 1.2227 (1.93); 1.2216 (1.92); 1.2037 (2.77); 1.186 (1.91); 1.1793 (1.02); 1.1736 (0.88); 1.1245 (0.6); 1.1125 (0.67); 1.1014 (0.57); 1.0679 (0.48); 1.0511 (0.51); 1.0304 (0.46); 1.0162 (0.49); 0.9981 (0.55); 0.9771 (0.53); 0.9588 (0.58); 0.9287 (0.63); 0.8822 (1.63); 0.8594 (1.5); 0.8201 (0.84); 0.811 (0.79); 0.803 (0.8); 0.7924 (0.77); 0.7841 (0.61); 0.7761 (0.65); 0.7581 (0.47); 0.7488 (0.37); 0.741 (0.4); 0.6988 (0.33); 0.1463 (1.19); 0.008 (12.07); 0.0009 (247.04); −0.0002 (250.68); −0.0072 (13.61); −0.1491 (1.29)
Compound No. A-08, solvent: [CD3CN],
9.3605 (1.48); 8.6853 (1.12); 8.4783 (1.76); 8.4748 (1.74); 8.4665 (1.84); 8.4631 (1.69); 8.1361 (0.35); 8.1054 (0.44); 8.0917 (4.53); 8.0181 (1.69); 8.0148 (1.58); 7.9979 (1.85); 7.9946 (1.74); 7.6514 (2.91); 7.6224 (3.07); 7.5285 (1.63); 7.5168 (1.67); 7.5084 (1.6); 7.4965 (1.5); 7.3435 (0.43); 7.1551 (3.29); 4.7628 (0.92); 4.7565 (1.17); 4.7489 (2.82); 4.7428 (3.15); 3.9831 (0.86); 3.9357 (16); 2.8635 (0.5); 2.8574 (0.84); 2.8515 (0.58); 2.8459 (0.37); 2.8149 (0.95); 2.2751 (0.54); 2.2162 (12.77); 2.1614 (191.08); 2.1081 (1.59); 2.1022 (1.25); 1.9529 (37.09); 1.9468 (66.16); 1.9406 (88.32); 1.9345 (61.59); 1.9284 (31.84); 1.7848 (0.92); 1.7752 (0.57); 1.7691 (0.67); 1.7629 (0.49); 1.27 (0.98); 0.8821 (0.4); 0.8595 (0.39); 0.1462 (0.52); −0.0002 (102.48); −0.1494 (0.49)
Compound No. A-09, solvent: [CD3CN],
9.7656 (0.48); 9.2679 (0.47); 9.1263 (1.03); 8.9906 (0.85); 8.5824 (2.66); 8.5764 (2.66); 8.5725 (2.95); 8.474 (1.47); 8.47 (1.97); 8.4623 (1.63); 8.4583 (1.98); 8.454 (0.84); 8.1348 (1.24); 8.1298 (0.45); 8.1129 (0.53); 8.1093 (0.53); 8.0992 (2.46); 8.0929 (3.97); 8.0791 (0.55); 8.0714 (0.63); 8.0127 (1.24);

| 1H NMR data[b] |
|---|
| 8.009 (1.25); 8.0016 (0.82); 7.9978 (0.86); 7.9925 (1.41); 7.9888 (1.35); 7.9815 (0.82); 7.9776 (0.77); 7.8725 (0.48); 7.8159 (0.53); 7.8116 (0.92); 7.8071 (0.54); 7.7967 (1.08); 7.7924 (1.91); 7.7881 (1.03); 7.7775 (0.64); 7.7732 (1.07); 7.7688 (0.6); 7.6682 (3.34); 7.6543 (2.47); 7.643 (2.24); 7.6283 (0.52); 7.62 (0.52); 7.6081 (0.57); 7.5894 (0.87); 7.5236 (1.34); 7.5197 (0.79); 7.5153 (1.08); 7.5118 (1.39); 7.5035 (1.91); 7.4951 (0.95); 7.4916 (1.26); 7.4835 (0.71); 7.3939 (2.33); 7.3794 (2.62); 7.3749 (2.47); 7.3603 (2.06); 7.3429 (1.27); 7.2287 (1.35); 7.1535 (3.15); 3.9851 (0.37); 3.9811 (0.51); 3.9587 (0.4); 3.9404 (11.05); 3.937 (16); 3.5227 (0.33); 3.4005 (14.59); 3.0712 (1.44); 2.9574 (14.27); 2.2433 (11.15); 2.2329 (8.57); 2.1978 (6.95); 2.1197 (0.69); 2.1136 (0.87); 2.1074 (1.01); 2.1013 (0.76); 2.095 (0.51); 1.9643 (5.32); 1.9579 (7.43); 1.9523 (46.73); 1.9462 (85.82); 1.9401 (117.58); 1.9339 (80.36); 1.9277 (41); 1.7844 (2.76); 1.7747 (0.58); 1.7685 (0.72); 1.7623 (0.47); 1.6761 (0.96); 1.3717 (0.7); 1.2764 (0.95); 1.2693 (0.52); 0.1458 (0.59); 0.0078 (6.16); −0.0002 (127.27); −0.0085 (4.77); −0.1496 (0.56) |
| Compound No. A-10, solvent: [CD3CN], |
| 9.0708 (0.8); 8.5835 (0.67); 8.5733 (0.7); 8.4857 (1.68); 8.4824 (1.82); 8.474 (1.86); 8.4707 (1.85); 8.0269 (4.85); 8.0133 (1.82); 7.8339 (0.38); 7.8148 (1.23); 7.7961 (0.53); 7.5398 (1.59); 7.5281 (1.63); 7.5197 (1.6); 7.5079 (1.56); 7.4822 (1.87); 7.4119 (0.65); 7.3973 (0.77); 7.3928 (0.79); 7.3783 (0.75); 7.3158 (1.43); 7.1547 (2.51); 4.049 (0.71); 4.0327 (1.45); 4.0156 (1.38); 3.9994 (0.56); 3.9558 (0.69); 3.943 (0.41); 3.9324 (0.89); 3.9262 (1.31); 3.9229 (1.18); 3.9071 (16); 3.2572 (0.39); 3.1494 (5.45); 3.0146 (0.34); 2.9607 (0.35); 2.2025 (7.29); 2.1609 (25.14); 2.12 (0.93); 2.1137 (0.88); 2.1075 (0.87); 2.1013 (0.66); 2.0952 (0.45); 1.9643 (3.36); 1.9524 (28.72); 1.9463 (52.43); 1.9401 (71.83); 1.9339 (49.68); 1.9277 (25.64); 1.7747 (0.33); 1.7685 (0.45); 1.3719 (0.46); 1.2765 (0.89); 1.265 (0.58); 1.2472 (0.63); 1.2414 (0.52); 1.2296 (0.39); 1.2234 (0.56); 1.0638 (1.67); 1.0466 (2.88); 1.0294 (1.53); 0.1457 (0.32); 0.0079 (3.66); −0.0002 (72.72); −0.0084 (3.67); −0.1497 (0.32) |
| Compound No. A-11, solvent: [CD3CN], |
| 9.4181 (0.43); 9.3462 (0.6); 8.6533 (0.89); 8.6418 (0.89); 8.4459 (0.73); 8.442 (0.77); 8.434 (0.77); 8.4303 (0.74); 8.26 (0.43); 8.1361 (0.81); 8.1303 (0.33); 8.1087 (2.29); 8.0753 (0.34); 8.0024 (0.71); 7.9985 (0.73); 7.9822 (0.78); 7.9783 (0.79); 7.7878 (0.57); 7.7687 (1.55); 7.7643 (1.41); 7.6657 (0.93); 7.5129 (0.81); 7.5011 (0.79); 7.4927 (0.75); 7.4809 (0.74); 7.3439 (0.85); 7.2476 (1.29); 4.0009 (0.42); 3.9826 (0.33); 3.9534 (0.35); 3.9431 (3.43); 3.9378 (8.61); 2.4185 (0.42); 2.3156 (16); 2.2425 (8.29); 2.1761 (9.95); 2.1203 (4.18); 2.114 (3.95); 2.1078 (3.8); 2.1017 (3.23); 2.0955 (2.69); 1.9647 (5.9); 1.9585 (7.16); 1.9528 (54); 1.9466 (101.88); 1.9404 (141.43); 1.9342 (96.99); 1.928 (49.84); 1.8911 (0.58); 1.7852 (2.24); 1.775 (0.79); 1.7688 (0.99); 1.7627 (0.71); 1.7565 (0.44); 1.3717 (0.9); 1.2765 (1.1); 0.1458 (0.68); 0.008 (6.19); −0.0002 (164.83); −0.0086 (5.98); −0.1497 (0.69) |
| Compound No. A-12, solvent: [CD3CN], |
| 8.6473 (0.75); 8.4523 (0.94); 8.4486 (0.98); 8.4406 (0.9); 8.437 (0.91); 8.0952 (2.82); 8.0075 (0.91); 8.004 (0.94); 7.9873 (0.98); 7.9838 (0.95); 7.6425 (1.4); 7.5128 (1.02); 7.5011 (1.01); 7.4928 (0.91); 7.4809 (0.83); 7.4195 (1.52); 7.1275 (3.08); 4.0853 (0.36); 4.0674 (1.08); 4.0496 (1.09); 4.0318 (0.36); 3.9699 (0.37); 3.9322 (9.87); 3.916 (0.5); 3.4736 (0.41); 3.4205 (16); 3.2075 (0.61); 3.1637 (9.32); 2.9954 (1.22); 2.2336 (6.91); 2.1965 (0.39); 2.1416 (21.61); 2.1136 (0.46); 2.1074 (0.44); 1.9719 (5.31); 1.9642 (2.72); 1.9524 (18.58); 1.9463 (32.78); 1.9401 (44.08); 1.934 (29.93); 1.9278 (15.29); 1.3713 (0.32); 1.3457 (0.53); 1.2761 (0.45); 1.2214 (1.25); 1.2036 (2.43); 1.1858 (1.21); 1.1414 (0.53); 0.0076 (2.99); −0.0002 (46.71); −0.0085 (1.86) |
| Compound No. A-13, solvent: [CD3CN], |
| 9.0188 (0.57); 8.5728 (2.11); 8.5624 (2.07); 8.4873 (1.54); 8.484 (1.71); 8.4756 (1.76); 8.4722 (1.83); 8.0855 (0.34); 8.0331 (5.44); 8.0148 (1.62); 7.8974 (0.53); 7.7601 (0.92); 7.7554 (0.73); 7.7515 (0.45); 7.7406 (0.81); 7.7365 (1.49); 7.732 (0.88); 7.7219 (0.55); 7.7174 (0.88); 7.7131 (0.54); 7.5402 (1.63); 7.5283 (1.78); 7.52 (1.86); 7.508 (2.94); 7.3468 (2.11); 7.3436 (1.54); 7.3324 (2.31); 7.3277 (2.28); 7.3243 (1.63); 7.3134 (3.07); 7.1571 (3.35); 4.099 (1.34); 3.9571 (0.56); 3.9335 (0.7); 3.9272 (1.11); 3.9107 (16); 3.3609 (1.49); 3.3289 (0.68); 3.3068 (0.39); 3.1634 (5.33); 3.1464 (5.87); 2.2152 (6.71); 2.1896 (0.61); 2.1437 (230.82); 2.1201 (1.49); 2.1138 (1.58); 2.1076 (1.79); 2.1014 (1.21); 2.0955 (0.7); 1.9643 (8.81); 1.9577 (12.34); 1.9524 (83.95); 1.9463 (155.67); 1.9402 (215.27); 1.9341 (149.86); 1.9279 (77.58); 1.7809 (0.57); 1.7749 (0.93); 1.7686 (1.29); 1.7625 (0.92); 1.7565 (0.49); 1.3715 (2.37); 1.2763 (2.9); 0.1457 (1.04); 0.0074 (9.63); −0.0002 (218.59); −0.0083 (11.55); −0.1498 (1.07) |
| Compound No. A-14, solvent: [CD3CN], |
| 9.2572 (0.82); 8.6947 (0.66); 8.5779 (0.53); 8.5657 (0.47); 8.486 (1.5); 8.4829 (1.51); 8.4744 (1.58); 8.1368 (0.34); 8.1034 (0.34); 8.0349 (3.5); 8.0259 (1.82); 8.0023 (1.62); 8.0057 (1.83); 8.0021 (1.65); 7.5368 (1.53); 7.5249 (1.62); 7.5166 (1.58); 7.5049 (1.6); 7.4854 (2.28); 7.3583 (0.36); 7.3443 (0.46); 7.2926 (1.95); 7.2075 (2.8); 7.1445 (0.36); 3.9597 (0.6); 3.9434 (1.21); 3.9338 (1.38); 3.9277 (1.18); 3.9226 (1.07); 3.9114 (16); 3.1678 (10.06); 2.9875 (1.08); 2.314 (1.52); 2.2879 (0.44); 2.2295 (1.48); 2.1773 (11.52); 2.144 (173.48); 2.1139 (2.13); 2.1078 (2.21); 2.1015 (1.5); 2.0954 (0.89); 1.9644 (10.24); 1.9525 (89.77); 1.9464 (163.62); 1.9403 (222.08); 1.9341 (153.23); 1.9279 (79.09); 1.786 (0.97); 1.7749 (1.03); 1.7687 (1.36); 1.7625 (0.96); 1.7564 (0.56); 1.6542 (9.93); 1.372 (2.7); 1.3405 (0.33); 1.2981 (0.34); 1.2767 (3.47); 0.146 (1.17); 0.0077 (12.98); −0.0002 (254.83); −0.1495 (1.22) |
| Compound No. A-15, solvent: [DMSO], |
| 12.6642 (0.39); 10.4604 (0.38); 10.4154 (1.23); 10.3608 (2.63); 10.2876 (2.91); 9.9322 (3.05); 9.3195 (1.42); 8.506 (2.08); 8.4974 (2.91); 8.4898 (1.8); 8.4859 (1.42); 8.3172 (0.69); 8.2929 (2.15); 8.2469 (9.93); 8.192 (1.06); 8.1875 (1.86); 8.1719 (1.4); 8.1674 (2.18); 7.8602 (0.91); 7.8556 (0.98); 7.7155 (0.88); 7.6685 (3.17); 7.6356 (4.79); 7.6328 (4.83); 7.621 (1.77); 7.6127 (2.44); 7.6055 (1.94); 7.6006 (1.62); 7.594 (1.76); 7.4478 (1.76); 7.4284 (3.56); 7.4089 (2.37); 7.3685 (4.83); 7.3659 (5.3); 7.3359 (0.61); 7.2711 (1.28); 7.2524 (1.96); 7.2338 (1.07); 7.2125 (0.45); 7.1811 (0.48); 7.1738 (1.15); 7.1604 (3.63); 7.14 (3.24); 7.0074 (0.52); 6.9917 (0.43); 6.7751 (0.37); 6.7564 (1.67); 6.754 (1.66); 6.7348 (1.49); 3.9167 (6.78); 3.9023 (16); 3.3284 (142.98); 3.3049 (0.8); 2.6752 (0.85); 2.6707 (1.17); 2.6662 (0.86); 2.5408 (0.81); 2.5105 (59.25); 2.5061 (120.1); 2.5016 (160.71); 2.4971 (118.24); 2.4927 (57.57); 2.4122 (0.57); 2.3329 (0.87); 2.3283 (1.15); 2.3238 (0.85); 2.2188 (4.14); 2.1749 (13.16); 1.3355 (2.41); 1.2582 (0.46); 1.2492 (2.97); 1.2345 (0.59); 0.1458 (0.35); 0.0079 (3.01); −0.0002 (82.35); −0.0084 (3); −0.1499 (0.34) |

| 1H NMR data[b] |
|---|

Compound No. A-16, solvent: [CD3CN],
9.1373 (0.68); 8.4874 (1.74); 8.4839 (1.93); 8.4757 (2.11); 8.4721 (2.12); 8.0862 (0.41); 8.0534 (0.38); 8.044 (0.57); 8.035 (1.7); 8.0315 (1.93); 8.0236 (4.07); 8.015 (2.28); 8.0118 (1.9); 7.9985 (0.52); 7.9946 (0.46); 7.8111 (0.76); 7.5413 (1.88); 7.5295 (2.06); 7.5211 (1.9); 7.5093 (1.83); 7.4817 (1.87); 7.4562 (0.35); 7.3878 (0.47); 7.3444 (0.38); 7.3247 (1.43); 7.1616 (1.86); 7.1067 (0.42); 4.8304 (0.34); 4.8155 (0.71); 4.8001 (0.9); 4.7848 (0.68); 3.9526 (1.01); 3.9433 (0.35); 3.9305 (0.98); 3.9277 (1.28); 3.9228 (1.19); 3.9032 (16); 3.1415 (6.15); 3.0898 (0.38); 2.8737 (0.68); 2.2296 (1.42); 2.2051 (7.05); 2.1583 (233.11); 2.1203 (1.5); 2.1142 (1.57); 2.1079 (1.69); 2.1018 (1.25); 2.0956 (0.79); 2.0868 (0.99); 1.9647 (4.79); 1.9583 (7.76); 1.9529 (65.41); 1.9467 (123.06); 1.9405 (173.06); 1.9344 (119.71); 1.9282 (61.98); 1.818 (0.35); 1.7813 (0.5); 1.7751 (0.81); 1.769 (1.12); 1.7628 (0.79); 1.7567 (0.45); 1.2967 (0.54); 1.2789 (1.12); 1.2693 (1.16); 1.2613 (1.11); 1.0415 (2.59); 0.146 (0.82); 0.008 (8.5); −0.0002 (190.56); −0.0085 (7.95); −0.1496 (0.83)

Compound No. A-17, solvent: [DMSO],
10.3931 (1.72); 10.1361 (2.91); 9.2339 (1.05); 8.5444 (2.21); 8.5408 (2.42); 8.5327 (2.39); 8.5291 (2.4); 8.3492 (0.44); 8.3187 (0.6); 8.249 (6.08); 8.2403 (2.38); 8.2367 (2.26); 8.22 (2.33); 8.2164 (2.2); 7.8965 (0.37); 7.7249 (4.95); 7.6829 (2.32); 7.6711 (2.41); 7.6627 (2.39); 7.6508 (3.44); 7.6273 (3.3); 4.1144 (0.4); 4.0965 (0.78); 4.081 (1.23); 4.0644 (1.28); 4.0415 (0.89); 4.0235 (0.61); 3.9422 (0.97); 3.924 (2.2); 3.9128 (16); 3.8868 (0.48); 3.3332 (241.22); 2.6758 (1.13); 2.6713 (1.55); 2.6669 (1.17); 2.5414 (0.79); 2.5246 (4.65); 2.5196 (7.1); 2.5111 (80.68); 2.5067 (162.76); 2.5022 (215.58); 2.4977 (161.06); 2.4933 (82.68); 2.3334 (1.12); 2.329 (1.56); 2.3245 (1.19); 2.2034 (0.49); 2.168 (10.61); 1.7524 (0.89); 1.2321 (0.79); 1.2172 (1.47); 1.2016 (2.37); 1.191 (1.79); 1.1734 (1.28); 1.1557 (0.62); 1.1366 (0.51); 1.1188 (0.77); 1.1012 (0.43); 0.008 (1.62); −0.0002 (49.87); −0.0084 (2.32)

Compound No. A-18, solvent: [CD3CN],
8.5118 (1.36); 8.5081 (1.44); 8.5001 (1.42); 8.4964 (1.42); 8.0934 (4.46); 8.0526 (1.33); 8.0489 (1.36); 8.0323 (1.46); 8.0286 (1.42); 7.9249 (0.35); 7.6441 (1.72); 7.6172 (2.16); 7.5769 (1.49); 7.5651 (1.49); 7.5567 (1.39); 7.5449 (1.35); 7.4575 (2.1); 4.8874 (0.61); 4.8718 (0.82); 4.8565 (0.63); 3.9351 (16); 3.9135 (0.38); 2.8894 (4.44); 2.7721 (3.64); 2.2187 (10.93); 2.1736 (86.23); 2.1148 (0.36); 2.1087 (0.45); 1.9726 (1.55); 1.9655 (3.2); 1.9594 (3.66); 1.9536 (27.27); 1.9475 (50.74); 1.9413 (70.38); 1.9351 (48.71); 1.9289 (25.3); 1.7697 (0.4); 1.2848 (0.33); 1.2691 (0.88); 1.2218 (2.86); 1.2039 (1.61); 1.1861 (0.74); −0.0002 (7.26)

Compound No. A-19, solvent: [CD3CN],
8.5028 (0.86); 8.4944 (0.89); 8.0991 (5.06); 8.0365 (0.89); 8.0163 (0.96); 7.6797 (2.83); 7.6392 (2.45); 7.5686 (1.07); 7.557 (1.11); 7.5485 (1.06); 7.5368 (0.95); 7.4255 (1.28); 7.2653 (0.59); 7.1645 (0.77); 7.1455 (0.78); 4.0674 (0.87); 4.0495 (0.9); 3.9485 (0.42); 3.9333 (16); 2.2281 (10.57); 2.147 (42.55); 2.1202 (0.48); 2.1141 (0.63); 2.108 (0.75); 2.1018 (0.5); 1.9722 (4.39); 1.9648 (5.05); 1.9585 (5.82); 1.9529 (41.09); 1.9467 (76.26); 1.9405 (105.9); 1.9344 (73.21); 1.9282 (38.03); 1.7752 (0.42); 1.7691 (0.6); 1.7629 (0.41); 1.3719 (1.33); 1.285 (0.32); 1.2765 (1.59); 1.2703 (0.68); 1.2215 (1.07); 1.2037 (2.09); 1.1859 (1.04); 0.0079 (0.59); −0.0002 (16.05); −0.0083 (0.62)

Compound No. A-20, solvent: [DMSO],
10.3979 (2.01); 10.156 (1.38); 9.354 (1.3); 8.545 (2.01); 8.5413 (2.17); 8.5332 (2.15); 8.5295 (2.13); 8.3185 (0.45); 8.2468 (3.1); 8.2399 (2.45); 8.2362 (2.12); 8.2195 (2.07); 8.2159 (1.93); 7.7215 (2.75); 7.6829 (2.09); 7.6712 (1.98); 7.6627 (2.06); 7.6508 (3.86); 7.6265 (2.78); 4.1996 (0.33); 4.1886 (0.35); 4.1767 (0.42); 4.1461 (1.61); 3.9437 (0.63); 3.9297 (0.55); 3.9139 (16); 3.8915 (0.41); 3.7237 (0.59); 3.5346 (1.53); 3.5232 (1.9); 3.5124 (1.46); 3.3328 (157.63); 3.2678 (5.3); 3.2558 (2.91); 3.202 (0.63); 2.6757 (0.78); 2.6712 (1.07); 2.6667 (0.79); 2.5245 (3.15); 2.5111 (57.24); 2.5067 (114.34); 2.5022 (151.08); 2.4976 (112.35); 2.4933 (56.68); 2.3333 (0.75); 2.329 (1.05); 2.3244 (0.8); 2.1658 (9.48); 0.0079 (1.14); −0.0002 (33.76); −0.0084 (1.44)

Compound No. A-21, solvent: [CD3CN],
8.5115 (1.46); 8.5079 (1.58); 8.4998 (1.56); 8.4961 (1.6); 8.0935 (4.72); 8.051 (1.41); 8.0474 (1.5); 8.0308 (1.54); 8.0272 (1.56); 7.6491 (2.6); 7.622 (2.37); 7.5755 (1.78); 7.5637 (1.81); 7.5552 (1.74); 7.5434 (1.65); 7.4482 (2.06); 5.2299 (0.33); 5.2136 (0.33); 4.5897 (1.16); 4.0855 (0.49); 4.0676 (1.49); 4.0498 (1.52); 4.032 (0.52); 3.9364 (16); 2.2206 (11.24); 2.1764 (94.84); 2.1722 (185.87); 2.1086 (0.33); 1.9726 (6.88); 1.9654 (1.75); 1.9592 (2.32); 1.9536 (18.97); 1.9474 (35.65); 1.9412 (50.22); 1.935 (35.21); 1.9289 (18.44); 1.2216 (1.7); 1.2038 (3.39); 1.1859 (1.69); 0.008 (2.2); −0.0002 (51.46); −0.0081 (2.59)

Compound No. A-22, solvent: [CD3CN],
9.407 (1.09); 8.7026 (0.92); 8.5116 (1.83); 8.5082 (1.91); 8.4998 (1.78); 8.4966 (1.74); 8.0932 (4.98); 8.0501 (1.83); 8.0468 (1.9); 8.0299 (1.89); 8.0266 (1.86); 7.7641 (0.38); 7.7455 (0.36); 7.7244 (0.49); 7.6526 (3.57); 7.6254 (3.26); 7.5741 (2.11); 7.5623 (2.11); 7.554 (1.95); 7.5421 (1.7); 7.4471 (3.11); 5.4485 (0.39); 4.721 (1.91); 4.6551 (0.5); 4.6403 (0.46); 4.6285 (0.36); 3.9375 (16); 3.879 (0.57); 2.7985 (0.89); 2.2218 (13.31); 2.1671 (38.86); 2.119 (3.02); 2.0769 (1.45); 1.9636 (4.59); 1.9531 (13.4); 1.947 (21.19); 1.9409 (27.29); 1.9347 (19.54); 1.9286 (10.85); 1.8836 (1.93); 1.8403 (0.94); 1.7697 (0.33); 1.2695 (0.42); −0.0002 (31.84); −0.0593 (1); −0.0966 (0.47)

Compound No. A-23, solvent: [CD3CN],
8.5071 (1.46); 8.5034 (1.62); 8.4953 (1.56); 8.4916 (1.63); 8.0955 (4.22); 8.0455 (1.3); 8.0418 (1.38); 8.0253 (1.45); 8.0216 (1.47); 7.6568 (2.86); 7.6471 (2.64); 7.5705 (1.49); 7.5587 (1.46); 7.5503 (1.39); 7.5384 (1.33); 7.4419 (2.93); 3.9397 (16); 2.9434 (15.42); 2.2517 (9.91); 2.1767 (56.27); 2.1743 (73.44); 1.9724 (0.55); 1.9653 (0.85); 1.9591 (1.13); 1.9534 (10.42); 1.9472 (19.78); 1.941 (28.01); 1.9348 (19.67); 1.9287 (10.31); 0.008 (1.29); −0.0002 (34.37); −0.0084 (1.44)

Compound No. A-24, solvent: [CD3CN],
9.132 (0.51); 8.5187 (1.5); 8.5154 (1.72); 8.507 (1.72); 8.5036 (1.8); 8.0661 (1.39); 8.0461 (1.6); 8.0336 (4.5); 7.7882 (0.68); 7.7525 (1.19); 7.747 (0.57); 7.7386 (1.26); 7.7301 (1.39); 7.7218 (0.54); 7.7163 (1.28); 7.5886 (1.53); 7.5768 (1.52); 7.5684 (1.47); 7.5566 (1.36); 7.4986 (1.98); 7.4371 (2.12); 7.4195 (0.48); 7.329 (1.35); 7.1346 (1.22); 7.1292 (0.45); 7.1176 (0.48); 7.1122 (2.35); 7.1067 (0.55); 7.0952 (0.4); 7.0897 (1.16); 5.8038 (3.22); 4.2983 (1.66); 4.2851 (1.77); 4.2719 (1.75); 4.1311 (1.63); 4.1155 (3.24); 4.0999 (1.79); 4.0862 (0.33); 4.0354 (1.31); 4.018 (1.32); 3.9095 (16); 3.1432 (5.16); 2.9684 (0.42); 2.2657 (0.76); 2.2502 (1.62); 2.2346 (2.05); 2.2179 (6.8); 2.1601 (530.28); 2.1209

| 1H NMR data[b] |
|---|
| (1.13); 2.1146 (1.17); 2.1084 (1.35); 2.1023 (0.97); 2.096 (0.6); 1.9653 (4.62); 1.9591 (6.33); 1.9534 (58.3); 1.9472 (110.66); 1.9411 (158.28); 1.9349 (111.98); 1.9287 (59.11); 1.7818 (0.39); 1.7756 (0.71); 1.7695 (0.97); 1.7633 (0.71); 1.7571 (0.39); 1.3717 (6.1); 1.3402 (0.55); 1.2849 (1.04); 1.2764 (7.02); 1.2163 (0.39); 1.0676 (1.52); 1.0499 (2.67); 1.0323 (1.44); 0.1458 (0.76); 0.0215 (0.32); 0.0081 (6.51); −0.0002 (176.87); −0.0085 (8.51); −0.1497 (0.73) |
| Compound No. A-25, solvent: [CD3CN], |
| 8.5202 (1.54); 8.5167 (1.72); 8.5084 (1.67); 8.505 (1.72); 8.0702 (1.4); 8.0671 (1.45); 8.05 (1.66); 8.0469 (1.66); 8.0286 (3.78); 7.8505 (0.46); 7.8287 (0.68); 7.8238 (0.7); 7.7711 (0.34); 7.7675 (0.34); 7.5896 (1.63); 7.5777 (1.63); 7.5692 (1.57); 7.5574 (1.47); 7.4922 (1.89); 7.4507 (1.76); 7.4254 (0.76); 7.4192 (0.82); 7.3352 (1.42); 7.2614 (0.36); 7.2562 (0.39); 7.2403 (0.66); 7.2353 (0.65); 7.172 (0.55); 7.1659 (0.52); 7.151 (0.36); 7.1446 (0.32); 4.8137 (0.6); 4.7988 (0.76); 4.7831 (0.56); 4.6151 (0.4); 3.9324 (0.37); 3.9054 (14.65); 3.2581 (0.38); 3.1344 (5.51); 3.0875 (0.36); 2.962 (0.32); 2.6301 (1.11); 2.6181 (1.09); 2.4709 (0.51); 2.4663 (0.71); 2.4617 (0.52); 2.2179 (7.3); 2.1846 (172.77); 2.1794 (231.52); 2.1213 (0.71); 2.1151 (0.88); 2.1088 (1.06); 2.1027 (0.79); 2.0965 (0.5); 1.9726 (1.01); 1.9657 (4.05); 1.9594 (5.82); 1.9538 (47.96); 1.9476 (90.33); 1.9415 (127.75); 1.9353 (90.09); 1.9291 (47.98); 1.8426 (0.36); 1.8205 (2.21); 1.7822 (0.34); 1.7761 (0.59); 1.7699 (0.81); 1.7637 (0.59); 1.7576 (0.33); 1.3858 (0.92); 1.3718 (13.86); 1.3523 (0.37); 1.3402 (1.16); 1.3077 (0.55); 1.2849 (2.24); 1.2764 (16); 1.2217 (0.58); 1.2164 (0.58); 1.204 (0.52); 1.1859 (0.37); 1.1182 (0.36); 1.0425 (2.35); 0.8813 (0.55); 0.8533 (0.4); 0.8349 (0.43); 0.1461 (0.83); 0.008 (7.31); −0.0002 (179.85); −0.0084 (9.3); −0.1495 (0.84) |
| Compound No. A-26, solvent: [CD3CN], |
| 9.164 (0.49); 8.5276 (1.04); 8.519 (1.09); 8.5162 (1.08); 8.3221 (0.6); 8.0778 (5.18); 8.0589 (1.26); 8.0553 (1.27); 7.5966 (1.17); 7.5849 (1.17); 7.5763 (1.2); 7.5643 (2.16); 7.4282 (1.97); 7.4199 (2.07); 7.3582 (0.75); 7.3393 (1.49); 7.3194 (1.01); 7.2524 (0.66); 7.2348 (0.9); 7.2163 (0.33); 7.172 (0.63); 7.1658 (0.33); 6.8665 (1.42); 6.8467 (1.31); 3.924 (16); 3.9044 (0.45); 3.2382 (0.41); 3.1872 (5.46); 2.2712 (5.45); 2.2281 (0.59); 2.2208 (0.54); 2.1756 (95.89); 2.1718 (150.04); 2.1085 (0.43); 1.9654 (1.81); 1.9593 (2.43); 1.9535 (22.04); 1.9473 (41.43); 1.9411 (58.28); 1.9349 (40.65); 1.9288 (21.39); 1.7696 (0.34); 1.3717 (3.94); 1.2847 (0.52); 1.2763 (4.02); 1.2702 (0.82); 0.1459 (0.32); 0.0081 (3.07); −0.0002 (79.61); −0.0085 (3.3); −0.1495 (0.33) |
| Compound No. A-27, solvent: [CD3CN], |
| 9.1104 (0.73); 8.5206 (1.46); 8.517 (1.53); 8.5088 (1.57); 8.5052 (1.55); 8.0703 (1.24); 8.0672 (1.24); 8.05 (1.38); 8.0468 (1.37); 8.0341 (4.17); 7.7996 (0.84); 7.5887 (1.41); 7.5769 (1.5); 7.5684 (1.42); 7.5566 (1.3); 7.4973 (1.65); 7.4374 (3.33); 7.3223 (1.18); 4.0994 (1.18); 4.0674 (0.43); 4.0495 (0.35); 3.9147 (16); 3.3612 (1.34); 3.3179 (0.57); 3.1619 (4.52); 3.1417 (5.4); 2.9669 (0.35); 2.2165 (6.56); 2.1444 (18.8); 1.9722 (1.55); 1.9647 (1.15); 1.9585 (1.49); 1.9528 (13.38); 1.9466 (25.27); 1.9404 (35.65); 1.9342 (24.64); 1.9281 (12.69); 1.2214 (0.4); 1.2035 (0.79); 1.1857 (0.39); 0.008 (2.07); −0.0002 (59.44); −0.0086 (2.26) |
| Compound No. A-28, solvent: [CD3CN], |
| 9.1533 (0.47); 8.5173 (1.31); 8.5138 (1.51); 8.5055 (1.47); 8.502 (1.57); 8.0642 (1.22); 8.0439 (1.39); 8.0304 (3.91); 7.99956 (0.49); 7.5859 (1.39); 7.5739 (1.26); 7.5655 (1.23); 7.5537 (1.16); 7.5096 (1.92); 7.4447 (1.49); 7.4255 (0.34); 7.4191 (0.32); 7.3187 (1.36); 5.0804 (0.68); 5.0549 (0.63); 5.0208 (0.64); 4.9764 (0.56); 4.4815 (1.06); 4.0675 (0.72); 4.0496 (0.72); 3.9143 (16); 3.1511 (5.53); 2.9742 (0.36); 2.4689 (0.4); 2.4642 (0.57); 2.4595 (0.4); 2.2149 (5.83); 2.1597 (193.23); 2.1208 (0.95); 2.1146 (1.19); 2.1084 (1.46); 2.1022 (1.05); 2.096 (0.63); 1.9724 (3.75); 1.9653 (9.12); 1.9592 (9.79); 1.9533 (80.43); 1.9472 (150.55); 1.941 (210.35); 1.9348 (146.44); 1.9286 (76.18); 1.9158 (1.57); 1.7818 (0.51); 1.7756 (0.92); 1.7694 (1.29); 1.7633 (0.9); 1.7571 (0.49); 1.3857 (0.47); 1.3717 (5.19); 1.3629 (0.45); 1.3402 (0.63); 1.2851 (0.94); 1.2765 (5.97); 1.2217 (0.99); 1.2038 (1.86); 1.186 (0.95); 0.0081 (0.62); −0.0002 (20.18); −0.0085 (0.71) |
| Compound No. A-29, solvent: [CD3CN], |
| 9.0184 (0.59); 8.521 (1.63); 8.5176 (1.75); 8.5092 (1.8); 8.5058 (1.82); 8.0687 (1.39); 8.0511 (1.53); 8.0286 (3.96); 7.9632 (0.72); 7.5903 (1.54); 7.5785 (1.53); 7.5701 (1.48); 7.5583 (1.39); 7.5255 (2.49); 7.434 (2.23); 7.308 (1.63); 4.7487 (0.34); 4.7426 (0.36); 4.5828 (2.52); 4.0674 (0.83); 4.0496 (0.85); 3.9147 (16); 3.1424 (6.94); 3.0918 (0.37); 2.9711 (0.42); 2.6942 (1.16); 2.2231 (9.02); 2.1631 (0.37); 2.1429 (72.02); 2.1202 (0.34); 2.1142 (0.53); 2.108 (0.7); 2.1019 (0.44); 1.9723 (4.2); 1.9649 (4.38); 1.9588 (4.98); 1.953 (37.52); 1.9468 (69); 1.9406 (95.59); 1.9345 (65.8); 1.9283 (33.81); 1.7753 (0.4); 1.7691 (0.54); 1.7629 (0.38); 1.2697 (1.45); 1.2215 (1.01); 1.2037 (2); 1.1859 (1); 0.0079 (0.47); −0.0002 (12.73); −0.0085 (0.37) |
| Compound No. A-30, solvent: [CD3CN], |
| 9.3107 (0.57); 8.6231 (0.66); 8.5192 (1.34); 8.5162 (1.42); 8.5075 (1.4); 8.5045 (1.4); 8.0609 (1.59); 8.0574 (1.59); 8.0409 (5.04); 7.8959 (0.35); 7.5847 (1.83); 7.5731 (1.56); 7.5647 (1.49); 7.5529 (1.43); 7.4945 (2.14); 7.4735 (2.39); 7.306 (1.92); 3.9139 (16); 3.8543 (1.46); 3.1652 (10.27); 2.1866 (10.97); 2.1416 (178.03); 2.1195 (1.87); 2.1143 (1.48); 2.1081 (1.83); 2.1019 (1.09); 2.0958 (0.62); 1.9649 (10.23); 1.9585 (12.65); 1.953 (86); 1.9468 (159.46); 1.9406 (219.95); 1.9345 (152.94); 1.9283 (79.62); 1.7812 (0.53); 1.7753 (0.95); 1.7691 (1.33); 1.7629 (0.93); 1.7567 (0.52); 1.6671 (9.92); 1.2853 (0.33); 1.2698 (0.84); 0.008 (1.01); −0.0002 (29.56); −0.0085 (1.28) |
| Compound No. A-31, solvent: [CD3CN], |
| 8.823 (1.9); 8.5139 (2.8); 8.5104 (2.84); 8.5021 (2.96); 8.4986 (2.87); 8.087 (2.29); 8.0549 (2.59); 8.0345 (2.45); 7.9329 (1.36); 7.6464 (1.56); 7.6126 (0.49); 7.5785 (3.07); 7.5667 (3.05); 7.5582 (2.93); 7.5464 (2.9); 7.4615 (4.92); 7.4578 (4.82); 7.4399 (1.9); 3.9295 (16); 3.7565 (0.33); 3.2932 (1.11); 3.0846 (5.49); 2.9781 (0.8); 2.9486 (5.32); 2.7805 (1.14); 2.2782 (5.62); 2.2311 (1.33); 2.1474 (44.64); 2.1142 (0.33); 2.1079 (0.32); 1.9723 (1.38); 1.9648 (2.32); 1.9587 (2.62); 1.9529 (18.8); 1.9468 (35.05); 1.9406 (48.74); 1.9344 (33.74); 1.9282 (17.38); 1.2688 (0.51); 1.2214 (0.33); 1.2036 (0.64); −0.0002 (6.45) |
| Compound No. A-32, solvent: [CD3CN], |
| 9.4987 (0.82); 8.5978 (0.7); 8.5106 (1.4); 8.5071 (1.51); 8.4988 (1.59); 8.4953 (1.63); 8.2755 (1.37); 8.2073 (0.41); 8.1957 (0.4); 8.0917 (4.2); 8.0452 (1.55); 8.0417 (1.56); 8.025 (1.74); 8.0216 (1.76); 7.6616 (2.62); 7.6132 (2.22); 7.5852 (0.44); 7.5718 (1.77); 7.56 (1.77); 7.5515 (1.7); 7.5398 (1.62); |

| 1H NMR data[b] |
|---|

7.4867 (2.79); 4.0673 (0.64); 4.0496 (0.68); 3.9866 (1.6); 3.9483 (2.03); 3.9344 (16); 3.6352 (0.33); 3.5715 (0.57); 2.6047 (1.04); 2.3116 (0.38); 2.2935 (0.64); 2.2549 (0.71); 2.2141 (10.21); 2.2007 (1.91); 2.1474 (302.85); 2.1203 (1.95); 2.1146 (2.65); 2.1081 (2.01); 2.102 (1.39); 2.0957 (0.78); 2.0128 (0.45); 1.9724 (16.39); 1.9649 (8.66); 1.9586 (11.41); 1.953 (90.8); 1.9469 (171.48); 1.9407 (242.35); 1.9345 (170.68); 1.9283 (90.73); 1.8906 (0.88); 1.8556 (0.88); 1.8309 (1.42); 1.7982 (0.52); 1.7815 (0.66); 1.7753 (1.11); 1.7691 (1.52); 1.7629 (1.09); 1.7568 (0.64); 1.3858 (0.32); 1.3403 (0.9); 1.2852 (1.37); 1.2695 (2.06); 1.2216 (0.88); 1.2038 (1.64); 1.1859 (0.85); 1.1267 (0.46); 1.0937 (0.35); 0.8813 (0.43); 0.8628 (0.33); 0.146 (1.53); 0.008 (13.84); −0.0002 (327.59); −0.0084 (17.37); −0.1495 (1.53)

Compound No. A-33, solvent: [CD3CN],
9.3661 (0.79); 8.7072 (1.09); 8.4615 (1.57); 8.4578 (1.59); 8.4497 (1.65); 8.446 (1.54); 8.1284 (0.33); 8.0926 (4.51); 7.9926 (1.54); 7.9889 (1.45); 7.9724 (1.68); 7.9688 (1.54); 7.6499 (1.87); 7.6174 (2.38); 7.5006 (0.38); 7.4899 (1.66); 7.4782 (1.61); 7.4697 (1.52); 7.4579 (1.44); 6.6425 (2.88); 4.7976 (1.06); 4.7904 (0.39); 4.7762 (3.19); 4.7547 (3.23); 4.7331 (1.13); 4.0673 (0.52); 4.0496 (0.53); 3.9816 (0.57); 3.9529 (1.2); 3.935 (16); 3.872 (1.14); 3.7141 (0.89); 3.6903 (1.62); 2.4691 (0.82); 2.4644 (1.09); 2.4598 (0.8); 2.4549 (0.44); 2.2969 (0.85); 2.2214 (11.34); 2.1731 (333.59); 2.121 (0.59); 2.1148 (0.89); 2.1087 (1.19); 2.1025 (0.86); 2.0964 (0.48); 1.9725 (3.32); 1.9655 (6.26); 1.9536 (70.47); 1.9475 (131.55); 1.9413 (182.87); 1.9351 (127.84); 1.929 (67.07); 1.7822 (0.44); 1.7759 (0.74); 1.7697 (1.04); 1.7636 (0.73); 1.7573 (0.37); 1.2848 (0.44); 1.2705 (0.72); 1.2569 (0.52); 1.2216 (0.64); 1.2038 (1.25); 1.186 (0.62); 0.1459 (1.39); 0.0079 (13.61); −0.0002 (301.06); −0.0085 (15.89); −0.1496 (1.36)

Compound No. A-34, solvent: [CD3CN], Spektrometer: 601.6 MHz
9.3175 (0.5); 8.6954 (0.9); 8.5736 (0.44); 8.44 (1.57); 8.4375 (1.51); 8.4322 (1.52); 8.4296 (1.48); 8.0899 (4.26); 7.9687 (1.42); 7.9662 (1.33); 7.9553 (1.46); 7.9528 (1.45); 7.6474 (1.21); 7.6115 (2.1); 7.4548 (1.35); 7.4469 (1.34); 7.4414 (1.43); 7.4335 (1.14); 7.354 (0.36); 7.3433 (0.46); 7.3322 (0.38); 6.5172 (2.25); 4.2758 (0.88); 4.264 (2.66); 4.2524 (2.67); 4.2405 (0.88); 3.981 (0.59); 3.9532 (0.37); 3.9342 (16); 3.8719 (0.38); 3.7145 (0.89); 3.6994 (0.98); 3.6609 (0.42); 2.4674 (0.34); 2.4643 (0.42); 2.2207 (8.97); 2.1784 (83.86); 2.0561 (0.36); 2.0521 (0.61); 2.0478 (0.34); 1.9658 (2.54); 1.9576 (2.51); 1.9534 (3.65); 1.9497 (32.8); 1.9456 (59.01); 1.9415 (83.47); 1.9374 (57.03); 1.9333 (29.29); 1.8311 (0.34); 1.8267 (0.45); 1.3984 (3.29); 1.3867 (6.59); 1.375 (3.28); 0.0053 (0.61); −0.0002 (20.44)

Compound No. A-35, solvent: [CD3CN],
9.2761 (0.78); 8.6296 (0.85); 8.4363 (1.47); 8.433 (1.57); 8.4246 (1.5); 8.4212 (1.52); 8.0867 (4.51); 7.9718 (1.5); 7.9683 (1.49); 7.9514 (1.51); 7.9482 (1.53); 7.641 (2.01); 7.626 (2.38); 7.4631 (1.58); 7.4546 (1.79); 7.4429 (1.83); 7.4346 (1.7); 7.4228 (1.44); 6.4918 (2.42); 4.8595 (0.43); 4.8442 (0.97); 4.829 (1.26); 4.8138 (0.96); 4.7984 (0.39); 3.9803 (0.86); 3.9523 (0.55); 3.9337 (15.35); 3.8714 (0.47); 3.7322 (0.34); 3.7134 (1.97); 3.6865 (1.75); 3.6616 (1.21); 2.2948 (0.42); 2.2401 (0.89); 2.2212 (12.14); 2.159 (3.42); 2.113 (0.86); 2.1067 (0.83); 2.1005 (0.64); 1.9712 (0.88); 1.9516 (16.67); 1.9454 (31.32); 1.9392 (44.6); 1.933 (31.15); 1.9269 (16.21); 1.7853 (0.75); 1.3956 (0.67); 1.3721 (16); 1.3568 (15.86); 1.3407 (0.39); 1.269 (0.47); 1.2036 (0.37); 0.1458 (0.32); 0.008 (2.66); −0.0002 (66.2); −0.0083 (3.24); −0.1496 (0.33)

Compound No. A-36, solvent: [CD3CN],
9.3061 (0.38); 8.8371 (1.78); 8.596 (0.7); 8.4462 (1.47); 8.4424 (1.5); 8.4344 (1.53); 8.4307 (1.46); 8.1309 (0.57); 8.1122 (1.03); 8.087 (4.76); 8.0701 (0.41); 8.064 (0.36); 7.9811 (1.51); 7.9774 (1.49); 7.961 (1.59); 7.9572 (1.51); 7.8243 (2.28); 7.8042 (2.01); 7.7368 (0.53); 7.7179 (0.35); 7.6467 (1.59); 7.6114 (2.02); 7.4718 (1.67); 7.46 (1.68); 7.4516 (1.63); 7.4399 (1.6); 7.3337 (0.76); 6.786 (0.64); 6.6002 (2.15); 5.4367 (0.75); 5.4175 (5.71); 3.9801 (0.56); 3.9402 (2.69); 3.9334 (16); 3.7128 (0.38); 3.6978 (1.24); 3.6813 (1.2); 3.662 (0.88); 2.2176 (10.5); 2.1347 (36.19); 2.1192 (0.45); 2.1128 (0.49); 2.1067 (0.59); 2.1006 (0.42); 1.9636 (2.08); 1.9575 (2.88); 1.9517 (30.49); 1.9455 (57.61); 1.9393 (80.92); 1.9331 (55.28); 1.927 (28.39); 1.9142 (0.44); 1.7854 (1.25); 1.774 (0.36); 1.7678 (0.51); 1.7616 (0.34); 1.471 (0.63); 1.3931 (0.38); 1.2851 (0.32); 1.2705 (0.34); −0.0002 (4.24)

Compound No. A-37, solvent: [CD3CN],
10.0116 (0.35); 9.3089 (0.66); 8.629 (0.78); 8.4534 (1.43); 8.4499 (1.46); 8.4418 (1.49); 8.4382 (1.44); 8.0889 (4.56); 7.9942 (0.37); 7.9864 (1.39); 7.9829 (1.41); 7.9663 (1.51); 7.9628 (1.44); 7.7422 (0.43); 7.7237 (0.36); 7.6455 (1.97); 7.6129 (2.36); 7.4785 (1.62); 7.4668 (1.63); 7.4583 (1.54); 7.4465 (1.46); 7.3572 (0.47); 7.3363 (0.43); 6.5923 (2.37); 6.3619 (0.63); 6.2342 (0.63); 6.2251 (1.26); 6.216 (0.65); 6.0974 (0.32); 6.0882 (0.62); 4.5157 (1.13); 4.5068 (1.14); 4.4798 (2.24); 4.4708 (2.21); 4.4439 (1.14); 4.4349 (1.09); 3.981 (0.57); 3.9526 (1.11); 3.9347 (16); 3.8717 (1.1); 3.762 (1.32); 3.7235 (0.59); 3.7182 (0.63); 3.6887 (1.71); 3.662 (0.62); 2.2955 (0.73); 2.2204 (11.31); 2.1678 (1.49); 2.1511 (28.84); 2.149 (29.55); 2.1201 (0.36); 2.113 (0.38); 2.1071 (0.44); 1.9639 (1.59); 1.952 (21.38); 1.9459 (40.28); 1.9397 (56.36); 1.9335 (38.54); 1.9274 (19.77); 1.9151 (0.34); 1.7682 (0.33); 1.2704 (0.34); −0.0002 (2.58)

Compound No. A-38, solvent: [CD3CN],
9.3359 (0.41); 8.7292 (0.42); 8.448 (1.37); 8.4442 (1.44); 8.4362 (1.41); 8.4324 (1.41); 8.0897 (4.19); 7.9749 (1.39); 7.9711 (1.36); 7.9547 (1.43); 7.951 (1.45); 7.6465 (1.63); 7.612 (1.95); 7.4638 (1.55); 7.452 (1.5); 7.4436 (1.42); 7.4319 (1.35); 6.7564 (0.34); 6.5394 (2.08); 5.2359 (0.37); 3.9798 (0.79); 3.9585 (1.3); 3.9524 (0.86); 3.9337 (16); 3.9265 (14.28); 3.8719 (0.67); 3.732 (0.33); 3.7153 (0.47); 3.6858 (1.41); 3.6614 (0.56); 2.4738 (0.38); 2.4692 (0.75); 2.4644 (1.05); 2.4597 (0.75); 2.4552 (0.38); 2.2969 (0.51); 2.2202 (10.34); 2.1745 (215.49); 2.12 (0.51); 2.1138 (0.71); 2.1076 (0.92); 2.1014 (0.66); 2.0953 (0.38); 1.9645 (4.77); 1.9583 (6); 1.9525 (52.42); 1.9464 (98.83); 1.9402 (138.27); 1.934 (94.99); 1.9278 (48.66); 1.9151 (0.88); 1.7747 (0.58); 1.7687 (0.82); 1.7624 (0.58); 1.2849 (0.39); 1.27 (0.6); −0.0002 (1.84)

Compound No. A-39, solvent: [CD3CN],
9.3918 (0.5); 8.6125 (0.5); 8.4977 (1.51); 8.4941 (1.48); 8.486 (1.53); 8.4823 (1.46); 8.0938 (4.41); 8.0307 (1.38); 8.0271 (1.31); 8.0105 (1.5); 8.0068 (1.38); 7.6502 (1.86); 7.622 (2.2); 7.5493 (1.56); 7.5375 (1.61); 7.5291 (1.45); 7.5173 (1.4); 7.3292 (1.98); 7.0783 (0.92); 6.9421 (1.91); 6.8058 (0.95); 3.9996 (0.42); 3.9527 (0.42); 3.9365 (16); 3.6858 (1.07); 3.6629 (0.75); 2.2251 (11.02); 2.1386 (41.57); 2.1191 (0.45); 2.1129 (0.58); 2.1068 (0.73); 2.1006 (0.48); 1.9636 (5.64); 1.9576 (8.65); 1.9517 (44.81); 1.9455 (80.08); 1.9394 (106.83); 1.9332 (72.89); 1.927 (37.23); 1.774 (0.45); 1.7678

| 1H NMR data[b)] |
| --- |

(0.6); 1.7616 (0.39); 1.3717 (3.99); 1.3403 (1.03); 1.2851 (1.45); 1.2766 (4.53); 0.1842 (0.33); 0.1461 (0.75); 0.008 (6); −0.0002 (152.7); −0.0086 (5.4); −0.1496 (0.72)
Compound No. A-40, solvent: [CD3CN], Spektrometer: 601.6 MHz
8.0714 (3.9); 7.6228 (1.22); 7.5813 (1.62); 7.5793 (1.49); 7.5013 (0.93); 7.4954 (1.15); 7.4919 (0.82); 7.491 (0.85); 7.4856 (1.31); 7.4791 (0.34); 7.4736 (0.79); 7.4676 (1.02); 7.4634 (0.88); 7.4577 (1.43); 7.4513 (0.35); 7.4257 (0.74); 7.4194 (3.05); 7.4134 (2.46); 7.4094 (2.2); 7.4035 (1.97); 7.3971 (0.34); 6.5 (1.77); 4.064 (0.56); 4.0521 (0.58); 3.9526 (0.72); 3.9321 (14.65); 3.91 (16); 3.8696 (0.78); 3.6859 (0.76); 3.6597 (0.43); 2.2733 (0.39); 2.1949 (9.07); 2.1623 (0.42); 2.1487 (17.4); 1.9705 (2.63); 1.95 (0.33); 1.9461 (3.8); 1.942 (7.3); 1.9379 (10.58); 1.9338 (7); 1.9297 (3.6); 1.3717 (2.4); 1.3398 (0.36); 1.2839 (0.52); 1.2758 (2.99); 1.2144 (0.76); 1.2026 (1.42); 1.1907 (0.73); −0.0002 (1.07)
Compound No. A-41, solvent: [CD3CN],
9.3113 (0.32); 8.8727 (0.49); 8.4751 (1.17); 8.4714 (1.18); 8.4633 (1.2); 8.4596 (1.15); 8.0844 (4.07); 8.0223 (1.47); 8.0185 (1.42); 8.0021 (1.63); 7.9982 (1.53); 7.6234 (1.75); 7.6111 (1.58); 7.5413 (1.68); 7.5296 (1.64); 7.5211 (1.53); 7.5093 (1.48); 7.3386 (0.71); 7.0743 (0.91); 6.938 (1.95); 6.8017 (0.97); 3.937 (16); 3.5168 (0.51); 3.0694 (2.21); 2.2369 (8.03); 2.2207 (0.45); 2.172 (17); 1.9642 (1.55); 1.9582 (2.27); 1.9523 (11.05); 1.9461 (19.52); 1.94 (26.08); 1.9338 (18.05); 1.9276 (9.26); 1.0991 (2.72); 1.0838 (2.72); −0.0002 (8.55)
Compound No. A-42, solvent: [CD3CN],
9.3508 (0.48); 8.6443 (0.49); 8.4768 (1.46); 8.473 (1.49); 8.465 (1.52); 8.4612 (1.47); 8.0902 (4.15); 8.0168 (1.31); 8.0131 (1.26); 7.9966 (1.44); 7.9928 (1.37); 7.6432 (2.12); 7.6148 (2.12); 7.5274 (1.59); 7.5156 (1.58); 7.5072 (1.52); 7.4954 (1.47); 7.1484 (2.1); 3.935 (16); 3.6911 (1.49); 2.2143 (10.42); 2.1538 (59.07); 2.1492 (53.74); 2.1194 (0.44); 2.1132 (0.54); 2.1071 (0.57); 2.1009 (0.4); 1.9714 (0.7); 1.9639 (4.1); 1.9578 (5.5); 1.952 (33.77); 1.9458 (61.54); 1.9397 (82.38); 1.9335 (56.15); 1.9273 (28.5); 1.7742 (0.37); 1.7681 (0.5); 1.7619 (0.33); 1.3718 (1.94); 1.2851 (0.41); 1.2767 (2.37); 0.008 (0.47); −0.0002 (10.57); −0.0086 (0.33)
Compound No. A-43, solvent: [CD3CN],
9.1464 (0.35); 8.8084 (1.22); 8.5468 (0.35); 8.5388 (0.33); 8.5349 (0.35); 8.426 (1.27); 8.4225 (1.34); 8.4143 (1.26); 8.4108 (1.27); 8.1299 (1.1); 8.0821 (4.7); 8.0646 (1.44); 7.9669 (1.44); 7.963 (1.48); 7.9467 (1.54); 7.9429 (1.53); 7.8612 (0.51); 7.6218 (1.52); 7.6094 (2.41); 7.5814 (0.38); 7.5696 (0.39); 7.5612 (0.34); 7.4574 (1.51); 7.4456 (1.48); 7.4373 (1.42); 7.4255 (1.35); 6.9732 (0.44); 6.7159 (1.18); 6.5262 (1.58); 3.9826 (0.33); 3.9694 (0.41); 3.9454 (4.42); 3.9399 (5.15); 3.9341 (16); 3.922 (15.22); 3.6573 (0.57); 3.6482 (0.5); 3.6419 (0.82); 3.6319 (0.53); 3.6253 (0.48); 3.6166 (0.74); 3.0785 (3.94); 2.2472 (0.5); 2.2326 (10.74); 2.2219 (1.13); 2.1425 (40.45); 2.1132 (0.34); 2.107 (0.39); 1.9637 (2.11); 1.9518 (20.26); 1.9457 (37.27); 1.9395 (51.2); 1.9333 (34.84); 1.9272 (17.87); 1.8016 (0.73); 1.7859 (2.85); 1.768 (0.33); 1.3871 (5.94); 1.2692 (2.25); 0.1457 (0.37); 0.0078 (3.9); −0.0002 (78.64); −0.0085 (2.88); −0.1499 (0.37)
Compound No. A-44, solvent: [CD3CN],
8.4815 (1.44); 8.4777 (1.5); 8.4697 (1.55); 8.4659 (1.47); 8.1593 (0.5); 8.0907 (4.03); 8.0118 (1.41); 8.0079 (1.4); 7.9968 (0.38); 7.9916 (1.59); 7.9877 (1.54); 7.9807 (0.36); 7.6505 (1.33); 7.6161 (1.78); 7.522 (1.68); 7.5101 (1.7); 7.5017 (1.66); 7.4899 (1.54); 7.451 (0.39); 7.4475 (0.51); 7.2168 (1.46); 5.5827 (0.54); 5.5663 (0.35); 5.5542 (3.29); 5.4624 (0.56); 5.4464 (0.34); 5.4342 (3.31); 5.2485 (0.59); 4.0858 (1.1); 4.0679 (3.34); 4.0501 (3.38); 4.0323 (1.14); 3.9821 (0.84); 3.9523 (0.69); 3.9421 (1.61); 3.9355 (16); 3.9243 (0.45); 3.8714 (0.56); 3.6919 (1.83); 3.6861 (0.93); 3.6614 (1.78); 2.2946 (0.35); 2.2425 (0.63); 2.2227 (9.6); 2.1751 (87.33); 2.1076 (0.38); 1.972 (15.73); 1.9645 (3.27); 1.9585 (4.02); 1.9526 (23.97); 1.9464 (43.85); 1.9402 (59.55); 1.9341 (40.78); 1.9279 (20.81); 1.914 (1.33); 1.7922 (0.49); 1.7687 (0.35); 1.2689 (0.55); 1.2214 (4.26); 1.2036 (8.5); 1.1858 (4.11); 0.008 (3.12); −0.0002 (80.51); −0.0086 (3.12)
Compound No. A-45, solvent: [CD3CN],
8.8251 (0.48); 8.4538 (1.12); 8.4501 (1.15); 8.442 (1.16); 8.4383 (1.14); 8.0765 (4.11); 8.0069 (1.39); 8.003 (1.36); 7.9866 (1.51); 7.9828 (1.46); 7.6129 (1.7); 7.5976 (1.69); 7.519 (1.57); 7.5072 (1.53); 7.4988 (1.44); 7.487 (1.41); 7.1444 (0.89); 4.0855 (0.47); 4.0676 (1.4); 4.0498 (1.41); 4.032 (0.48); 3.9357 (16); 3.9111 (0.46); 3.7532 (1.11); 3.7228 (0.35); 3.6422 (0.43); 3.6318 (4.29); 3.5535 (0.53); 3.1716 (0.63); 3.0742 (2.51); 3.0417 (0.37); 2.9943 (4.01); 2.2203 (8.98); 2.2072 (0.62); 2.1567 (16.45); 1.9716 (6.12); 1.964 (1.56); 1.958 (2.39); 1.952 (11.49); 1.9459 (20.29); 1.9397 (26.97); 1.9335 (18.58); 1.9274 (9.54); 1.3717 (0.68); 1.2763 (0.83); 1.27 (0.37); 1.2212 (1.67); 1.2034 (3.28); 1.1856 (1.63); 0.008 (0.44); −0.0002 (12.85); −0.0086 (0.34)
Compound No. A-46, solvent: [CD3CN],
9.2834 (0.33); 8.7842 (0.54); 8.4903 (1.07); 8.4866 (1.11); 8.4785 (1.09); 8.4747 (1.07); 8.0874 (4.03); 8.0432 (1.42); 8.0394 (1.41); 8.0229 (1.57); 8.0191 (1.48); 7.6289 (1.91); 7.6168 (1.46); 7.5682 (1.62); 7.5564 (1.58); 7.5479 (1.5); 7.5362 (1.47); 7.4451 (0.58); 4.0677 (0.43); 4.0498 (0.43); 3.9379 (16); 3.7534 (1.55); 3.7359 (0.35); 3.5278 (0.45); 3.1721 (0.89); 3.0746 (1.58); 2.2355 (7.2); 2.22 (0.81); 2.138 (14.9); 2.1067 (0.33); 1.9714 (2.08); 1.9637 (2.82); 1.9576 (4.33); 1.9517 (20.8); 1.9455 (36.81); 1.9393 (48.64); 1.9332 (33.54); 1.927 (17.21); 1.9203 (0.47); 1.3718 (1.6); 1.2766 (1.88); 1.2707 (0.39); 1.2213 (0.56); 1.2035 (1.08); 1.1857 (0.53); 0.0081 (0.94); −0.0002 (28.07); −0.0086 (0.76)
Compound No. A-47, solvent: [CD3CN],
8.7905 (1); 8.4618 (1.13); 8.4581 (1.14); 8.45 (1.16); 8.4463 (1.11); 8.0853 (4.17); 8.0049 (1.35); 8.0011 (1.29); 7.9847 (1.46); 7.9809 (1.35); 7.6271 (1.28); 7.6142 (1.83); 7.5157 (1.51); 7.5039 (1.49); 7.4955 (1.42); 7.4837 (1.34); 7.2136 (1.16); 5.55 (3.95); 5.4301 (3.95); 4.0676 (0.75); 4.0497 (0.76); 3.9364 (16); 3.9122 (0.49); 3.6241 (0.38); 3.5216 (0.53); 3.0727 (2.97); 2.2386 (8.74); 2.2217 (0.53); 2.1345 (14.38); 1.9868 (0.35); 1.9714 (3.46); 1.9635 (2.38); 1.9574 (3.51); 1.9515 (17.05); 1.9454 (30.2); 1.9392 (40.03); 1.933 (27.53); 1.9268 (14.1); 1.3718 (0.55); 1.2766 (0.63); 1.2212 (0.91); 1.2034 (1.79); 1.1856 (0.88); 0.0081 (0.54); −0.0002 (16.29); −0.0087 (0.45)
Compound No. A-49, solvent: [CD3CN],
9.2518 (0.69); 8.8872 (1.33); 8.7778 (1.14); 8.775 (1.11); 8.7593 (1.09); 8.4667 (0.51); 8.4635 (0.54); 8.4518 (1.9); 8.4402 (1.62); 8.2727 (1.53); 8.2471 (2.84); 8.0971 (1.74); 8.0853 (4.9); 8.06 (0.89); 7.9997 (1.71); 7.9964 (1.68); 7.9796 (1.9); 7.9763 (1.81); 7.8577 (1); 7.8398 (1.02); 7.625 (2.52); 7.6161 (3.13); 7.5467 (0.53); 7.5084 (1.74); 7.4965 (1.83); 7.4881 (1.73); 7.4763 (1.66); 7.2476 (0.36);

| 1H NMR data[b] |
| --- |
| 7.2377 (1.16); 7.0656 (0.79); 7.0557 (2.36); 6.9733 (0.54); 6.9464 (0.87); 6.9283 (1.58); 6.9101 (0.8); 6.8834 (0.36); 6.8737 (1.17); 6.8068 (1.88); 6.7736 (0.62); 4.0398 (0.58); 3.9824 (0.66); 3.9695 (10.03); 3.9523 (0.86); 3.9353 (16); 3.925 (4.01); 3.8702 (0.35); 3.818 (0.7); 3.7028 (0.45); 3.6656 (0.59); 3.6169 (0.32); 3.5535 (1.11); 3.3305 (0.44); 3.3148 (0.45); 3.2974 (0.41); 3.2906 (0.32); 3.0777 (4.26); 2.7029 (7.46); 2.4632 (0.41); 2.235 (11.66); 2.222 (1.9); 2.1931 (3.87); 2.1629 (139.24); 2.1139 (1.08); 2.1077 (1.07); 2.1016 (0.84); 2.0953 (0.58); 2.0726 (0.35); 2.0658 (0.35); 1.9641 (8.58); 1.9522 (45.33); 1.9462 (75.41); 1.9401 (94.33); 1.934 (67.35); 1.9279 (36.24); 1.7802 (0.38); 1.7746 (0.56); 1.7686 (0.68); 1.7624 (0.5); 1.7575 (0.32); 1.387 (6.83); 1.3399 (0.66); 1.2847 (1.13); 1.2692 (2.59); 1.2165 (0.49); 1.1474 (0.8); 1.1294 (1.5); 1.1112 (0.76); 0.881 (0.38); −0.0003 (4.09) |
| Compound No. B-01, solvent: [CD3CN], 9.4993 (0.82); 8.4735 (1.33); 8.4697 (1.38); 8.4617 (1.39); 8.4579 (1.38); 8.0564 (4.17); 8.0039 (1.35); 8 (1.33); 7.9837 (1.49); 7.9798 (1.4); 7.5976 (1.74); 7.5935 (1.98); 7.5378 (1.84); 7.521 (1.54); 7.5092 (1.48); 7.5008 (1.42); 7.489 (1.33); 7.1501 (3.07); 7.1249 (0.97); 3.9289 (16); 3.8104 (2.53); 3.7871 (2.63); 2.9338 (3.67); 2.9096 (3.47); 2.193 (10.26); 2.1382 (46.02); 2.1137 (0.47); 2.1074 (0.59); 2.1012 (0.41); 1.9643 (3.21); 1.9581 (4.2); 1.9524 (30.73); 1.9462 (56.92); 1.94 (78.83); 1.9338 (54.2); 1.9277 (27.99); 1.7745 (0.35); 1.7685 (0.49); 1.7623 (0.34); 1.712 (9.23); 0.1459 (0.43); 0.008 (3.82); −0.0002 (97.79); −0.0086 (3.93); −0.1496 (0.42) |
| Compound No. B-02, solvent: [CD3CN], 9.7107 (0.9); 8.5061 (1.38); 8.5023 (1.47); 8.4943 (1.47); 8.4906 (1.5); 8.0836 (4.26); 8.0407 (1.4); 8.037 (1.43); 8.0204 (1.56); 8.0167 (1.54); 7.6919 (2.43); 7.6879 (2.57); 7.589 (1.99); 7.5721 (1.61); 7.5603 (1.57); 7.5519 (1.47); 7.5401 (1.39); 7.4193 (2.59); 5.1095 (0.5); 5.0196 (0.39); 5.002 (0.89); 4.9849 (0.99); 4.9673 (0.58); 4.815 (2.18); 4.7977 (3.56); 4.7798 (2.03); 4.5486 (2.24); 4.5319 (3.97); 4.516 (1.99); 3.9862 (0.38); 3.9476 (0.4); 3.9355 (16); 3.6018 (2.7); 2.2069 (929.72); 2.1224 (0.85); 2.1162 (1.07); 2.11 (1.28); 2.1039 (0.94); 2.0977 (0.63); 1.9669 (4.67); 1.9607 (6.63); 1.955 (56.11); 1.9488 (105.53); 1.9426 (147.11); 1.9364 (102); 1.9303 (53.14); 1.7834 (0.41); 1.7772 (0.69); 1.7711 (0.92); 1.7649 (0.68); 1.7587 (0.39); 1.3867 (0.51); 1.2695 (0.38); 0.008 (2.51); −0.0002 (65.98); −0.0085 (2.58) |
| Compound No. B-03, solvent: [CD3CN], 8.472 (1.41); 8.4682 (1.46); 8.4602 (1.46); 8.4564 (1.46); 8.0763 (4.44); 8.0035 (1.41); 7.9998 (1.4); 7.9833 (1.58); 7.9796 (1.51); 7.6848 (2.49); 7.6807 (2.62); 7.5751 (2.01); 7.5228 (1.58); 7.511 (1.56); 7.5026 (1.47); 7.4908 (1.44); 7.1239 (3.04); 5.0255 (0.42); 5.0083 (0.92); 4.9911 (1); 4.9732 (0.6); 4.8183 (2.27); 4.8011 (3.66); 4.7831 (2.13); 4.5536 (2.27); 4.537 (4.23); 4.521 (2.07); 3.9832 (0.4); 3.9326 (16); 2.2027 (11.56); 2.1592 (129.82); 2.1208 (0.68); 2.1145 (0.76); 2.1084 (0.85); 2.1022 (0.62); 2.0961 (0.37); 1.9653 (3.5); 1.959 (4.8); 1.9533 (40.95); 1.9472 (78.14); 1.941 (109.79); 1.9348 (76.59); 1.9286 (39.99); 1.7756 (0.45); 1.7694 (0.64); 1.7633 (0.43); 1.3869 (0.44); 0.008 (1.86); −0.0002 (51.82); −0.0084 (2.47) |
| Compound No. B-04, solvent: [CD3CN], 9.4685 (1); 8.5074 (1.46); 8.5037 (1.45); 8.4956 (1.54); 8.492 (1.46); 8.4706 (0.51); 8.4676 (0.52); 8.0774 (4.45); 8.0455 (1.5); 8.0417 (1.5); 8.0252 (1.78); 8.0215 (1.76); 8.0091 (0.34); 8.0015 (0.5); 7.9854 (0.38); 7.6707 (2.14); 7.6669 (2.25); 7.5904 (3.18); 7.5733 (1.75); 7.5615 (1.7); 7.553 (1.82); 7.5412 (1.87); 7.5336 (0.57); 7.5268 (0.6); 7.5223 (0.57); 7.5138 (0.42); 7.5067 (0.35); 7.5021 (0.36); 7.4519 (0.32); 7.4362 (3.02); 7.2411 (0.32); 4.5463 (0.33); 4.5336 (0.45); 4.5248 (0.68); 4.512 (0.66); 4.5032 (0.73); 4.4909 (0.84); 4.4768 (2.11); 4.4708 (0.89); 4.4628 (0.53); 4.4503 (0.98); 4.4432 (1.95); 4.4305 (0.5); 4.4225 (1.13); 4.4187 (0.71); 4.1392 (0.33); 4.1297 (1.66); 4.1202 (2.15); 4.103 (0.57); 4.0944 (1.38); 4.0836 (1.49); 4.0672 (0.69); 4.0494 (0.69); 3.9636 (0.61); 3.9556 (0.47); 3.9496 (0.47); 3.9322 (16); 3.9139 (2.2); 3.9082 (1.98); 3.9032 (1.07); 3.7212 (0.48); 3.7087 (0.43); 2.2312 (11.05); 2.1934 (1.32); 2.1685 (1.18); 2.1434 (76.16); 2.1205 (1.28); 2.1147 (1.42); 2.1082 (1.37); 2.102 (1.01); 2.0959 (0.44); 1.9723 (3.94); 1.9649 (4.96); 1.9531 (48.45); 1.9469 (89.21); 1.9408 (123.09); 1.9346 (85.45); 1.9284 (44.47); 1.7753 (0.52); 1.7692 (0.71); 1.763 (0.49); 1.3722 (4.12); 1.3403 (0.61); 1.2849 (1.01); 1.2764 (4.66); 1.2215 (0.85); 1.2037 (1.6); 1.1859 (0.79); 0.1459 (0.89); 0.0079 (9.56); −0.0002 (190.83); −0.0084 (8.82); −0.1496 (0.89) |
| Compound No. B-05, solvent: [CD3CN], 9.4685 (1); 8.5074 (1.46); 8.5037 (1.45); 8.4956 (1.54); 8.492 (1.46); 8.4706 (0.51); 8.4676 (0.52); 8.0774 (4.45); 8.0455 (1.5); 8.0417 (1.5); 8.0252 (1.78); 8.0215 (1.76); 8.0091 (0.34); 8.0015 (0.5); 7.9854 (0.38); 7.6707 (2.14); 7.6669 (2.25); 7.5904 (3.18); 7.5733 (1.75); 7.5615 (1.7); 7.553 (1.82); 7.5412 (1.87); 7.5336 (0.57); 7.5268 (0.6); 7.5223 (0.57); 7.5138 (0.42); 7.5067 (0.35); 7.5021 (0.36); 7.4519 (0.32); 7.4362 (3.02); 7.2411 (0.32); 4.5463 (0.33); 4.5336 (0.45); 4.5248 (0.68); 4.512 (0.66); 4.5032 (0.73); 4.4909 (0.84); 4.4768 (2.11); 4.4708 (0.89); 4.4628 (0.53); 4.4503 (0.98); 4.4432 (1.95); 4.4305 (0.5); 4.4225 (1.13); 4.4187 (0.71); 4.1392 (0.33); 4.1297 (1.66); 4.1202 (2.15); 4.103 (0.57); 4.0944 (1.38); 4.0836 (1.49); 4.0672 (0.69); 4.0494 (0.69); 3.9636 (0.61); 3.9556 (0.47); 3.9496 (0.47); 3.9322 (16); 3.9139 (2.2); 3.9082 (1.98); 3.9032 (1.07); 3.7212 (0.48); 3.7087 (0.43); 2.2312 (11.05); 2.1934 (1.32); 2.1685 (1.18); 2.1434 (76.16); 2.1205 (1.28); 2.1147 (1.42); 2.1082 (1.37); 2.102 (1.01); 2.0959 (0.44); 1.9723 (3.94); 1.9649 (4.96); 1.9531 (48.45); 1.9469 (89.21); 1.9408 (123.09); 1.9346 (85.45); 1.9284 (44.47); 1.7753 (0.52); 1.7692 (0.71); 1.763 (0.49); 1.3722 (4.12); 1.3403 (0.61); 1.2849 (1.01); 1.2764 (4.66); 1.2215 (0.85); 1.2037 (1.6); 1.1859 (0.79); 0.1459 (0.89); 0.0079 (9.56); −0.0002 (190.83); −0.0084 (8.82); −0.1496 (0.89) |
| Compound No. B-06, solvent: [CD3CN], 9.7099 (1); 8.5076 (1.43); 8.5039 (1.41); 8.4958 (1.48); 8.4921 (1.42); 8.0672 (4.52); 8.0366 (1.42); 8.0329 (1.33); 8.0163 (1.54); 8.0126 (1.43); 7.6273 (2.11); 7.6235 (2.35); 7.5817 (0.59); 7.5691 (2.55); 7.5642 (2.81); 7.5586 (2.93); 7.5491 (1.57); 7.5373 (1.39); 7.4424 (2.7); 5.2299 (0.58); 5.209 (1.08); 5.1884 (1.11); 5.1676 (0.6); 3.9334 (16); 3.4696 (1.55); 3.4461 (3); 3.4238 (1.97); 3.2762 (1.98); 3.2727 (1.19); 3.2556 (2.95); 3.2523 (2.69); 3.2318 (1.55); 2.2025 (11.38); 2.1659 (47.31); 2.1618 (34.62); 1.9725 (0.75); 1.9653 (1.45); 1.9534 (16.75); 1.9473 (31.37); 1.9411 (44.06); 1.935 (30.72); 1.9288 (16); 1.3719 (1.34); 1.2764 (1.41); 0.1461 (0.34); 0.0079 (3.21); −0.0002 (73.75); −0.008 (3.21); −0.0085 (3.22); −0.1493 (0.34) |

-continued

| 1H NMR data[b] |
| --- |

Compound No. B-07, solvent: [CD3CN],
9.5594 (0.91); 8.4336 (1.46); 8.4297 (1.41); 8.4218 (1.51); 8.418 (1.38); 8.0754 (4.3); 7.9573 (1.48);
7.9534 (1.37); 7.9371 (1.62); 7.9333 (1.43); 7.6778 (2.14); 7.6735 (2.24); 7.6588 (0.58); 7.6462 (0.54);
7.5737 (2.06); 7.45 (1.54); 7.4383 (1.55); 7.4299 (1.44); 7.4181 (1.39); 6.4555 (2.55); 5.0322 (0.43);
5.0144 (0.93); 4.9972 (1.04); 4.98 (0.6); 4.8582 (0.39); 4.8429 (1); 4.8275 (1.4); 4.8178 (2.36); 4.8124
(1.22); 4.8006 (3.65); 4.7826 (2.04); 4.5576 (2.33); 4.5411 (4.11); 4.5251 (2.1); 3.9498 (0.7); 3.9312
(16); 3.8735 (0.62); 2.4622 (0.34); 2.2912 (0.43); 2.2118 (10.77); 2.1454 (90.29); 2.1192 (0.55); 2.113
(0.7); 2.1069 (0.72); 2.1006 (0.48); 1.9637 (4.09); 1.9575 (5.82); 1.9518 (40.01); 1.9456 (73.89);
1.9394 (101.51); 1.9333 (69.98); 1.9271 (36.04); 1.7741 (0.43); 1.7679 (0.6); 1.7617 (0.4); 1.3879
(0.32); 1.3709 (15.38); 1.3555 (15.26); 0.0079 (0.71); −0.0002 (20.31); −0.0085 (0.77)
Compound No. B-08, solvent: [CD3CN],
9.6028 (1.11); 8.8368 (1.94); 8.4387 (1.5); 8.4355 (1.56); 8.4269 (1.56); 8.4238 (1.54); 8.1125 (1.07);
8.0939 (1.22); 8.0702 (4.88); 7.9661 (1.47); 7.9629 (1.48); 7.9459 (1.62); 7.9428 (1.57); 7.8271 (2.26);
7.8068 (1.98); 7.7074 (0.84); 7.6902 (0.85); 7.6684 (2.48); 7.6649 (2.57); 7.5641 (2.44); 7.4662 (1.52);
7.4544 (1.49); 7.4461 (1.43); 7.4343 (1.35); 6.5724 (3.22); 5.4135 (6.78); 5.0168 (0.49); 4.9998 (1.06);
4.9824 (1.17); 4.9649 (0.69); 4.8117 (2.47); 4.7946 (4.1); 4.4768 (2.29); 4.5495 (2.54); 4.5332 (4.67);
4.5172 (2.23); 3.9304 (16); 3.6011 (2.54); 2.2873 (0.36); 2.2056 (377.82); 2.1384 (0.36); 2.1321
(0.35); 2.1199 (0.32); 2.1145 (0.35); 2.1079 (0.38); 2.1017 (0.36); 1.9644 (1.15); 1.9531 (16.05); 1.947
(29.92); 1.941 (41.67); 1.9349 (29.26); 1.9287 (15.4); 1.3869 (0.37); −0.0002 (27.26); −0.0006 (26.96);
−0.0082 (1.42)
Compound No. B-09, solvent: [CD3CN],
9.5879 (0.85); 8.4487 (1.55); 8.4449 (1.6); 8.437 (1.58); 8.4332 (1.52); 8.11 (0.33); 8.0724 (4.31);
7.9821 (0.38); 7.9702 (1.53); 7.9664 (1.51); 7.95 (1.62); 7.9462 (1.53); 7.6788 (1.9); 7.6746 (2.03);
7.6201 (0.63); 7.6052 (0.62); 7.5699 (1.94); 7.4719 (1.62); 7.4601 (1.57); 7.4518 (1.48); 7.4399 (1.42);
6.5517 (2.6); 6.3689 (0.33); 6.3598 (0.62); 6.2321 (0.65); 6.223 (1.28); 6.2139 (0.62); 6.0953 (0.33);
6.0862 (0.65); 5.028 (0.44); 5.01 (0.93); 4.9928 (1); 4.9754 (0.57); 4.8183 (2.17); 4.8011 (3.47);
4.7831 (1.99); 4.5554 (2.25); 4.5386 (4.02); 4.5227 (2.14); 4.5122 (1.21); 4.5031 (1.22); 4.4763 (2.4);
4.4672 (2.4); 4.4404 (1.24); 4.4312 (1.18); 3.9828 (0.38); 3.9696 (0.4); 3.9498 (1.3); 3.9321 (16);
3.9173 (0.44); 3.914 (0.51); 3.8731 (0.94); 3.5997 (3.34); 2.2885 (0.58); 2.2344 (0.51); 2.2058 (10.51);
2.1656 (0.67); 2.1305 (7.73); 2.1128 (0.33); 2.1065 (0.39); 1.9633 (1.49); 1.957 (2.46); 1.9514 (21.14);
1.9453 (39.87); 1.9391 (55.77); 1.9329 (38.51); 1.9267 (19.8); 1.7676 (0.32); 1.3873 (0.41); 1.2696
(0.59); −0.0002 (5.03)
Compound No. B-10, solvent: [CD3CN],
9.5923 (0.39); 8.4416 (1.41); 8.4377 (1.4); 8.4298 (1.44); 8.4259 (1.37); 8.0678 (3.96); 7.9557 (1.43);
7.9518 (1.38); 7.9355 (1.56); 7.9316 (1.44); 7.6696 (1.8); 7.6651 (1.86); 7.647 (0.53); 7.6306 (0.59);
7.5624 (1.69); 7.5592 (1.55); 7.454 (1.54); 7.4423 (1.49); 7.4339 (1.42); 7.4221 (1.36); 6.4982 (2.28);
5.025 (0.38); 5.0069 (0.84); 4.9898 (0.92); 4.9721 (0.52); 4.8138 (2); 4.7965 (3.13); 4.7785 (1.82);
4.6879 (0.89); 4.6708 (1.38); 4.6534 (0.99); 4.5526 (2.16); 4.5358 (3.52); 4.5199 (1.76); 4.2725 (0.89);
4.2563 (1.76); 4.24 (0.89); 4.044 (0.46); 4.0273 (0.7); 4.0107 (0.39); 3.9527 (0.52); 3.9491 (1.26);
3.9441 (0.66); 3.9305 (16); 3.9227 (15.43); 3.8899 (0.61); 3.8856 (0.37); 3.8723 (0.86); 3.5995 (2.1);
2.2867 (0.56); 2.2021 (9.82); 2.165 (1.01); 2.1364 (1.07); 2.1128 (0.7); 2.1065 (0.67);
2.1003 (0.52); 2.0942 (0.38); 1.9634 (1.34); 1.9573 (1.72); 1.9515 (14.23); 1.9453 (26.7); 1.9391
(37.22); 1.9329 (25.61); 1.9267 (13.16); 1.3872 (0.4); 1.2849 (0.32); −0.0002 (1.26)
Compound No. B-11, solvent: [CD3CN],
9.7096 (0.69); 8.4907 (1.58); 8.487 (1.52); 8.4789 (1.62); 8.4752 (1.48); 8.112 (0.44); 8.0842 (1);
8.0791 (4.11); 8.0161 (1.61); 8.0124 (1.43); 7.9959 (1.64); 7.9921 (1.52); 7.9834 (0.36); 7.7054 (0.35);
7.6882 (2.11); 7.6838 (2.21); 7.6052 (0.35); 7.6012 (0.34); 7.5818 (1.74); 7.5598 (0.33); 7.548 (0.38);
7.5422 (1.66); 7.5304 (1.64); 7.5219 (1.5); 7.5101 (1.43); 7.4308 (0.46); 7.305 (1.78); 7.0744 (0.92);
6.9538 (0.41); 6.9381 (2); 6.8018 (0.98); 5.0224 (0.38); 5.0044 (0.83); 4.9874 (0.9); 4.9697 (0.51);
4.8098 (1.98); 4.7925 (3.14); 4.7744 (1.97); 4.5481 (2.12); 4.5312 (3.59); 4.5153 (1.77); 4.4575 (0.43);
4.448 (0.34); 3.9843 (0.48); 3.9695 (0.68); 3.961 (0.35); 3.9566 (0.35); 3.9493 (1.7); 3.9427 (0.73);
3.9339 (16); 3.9192 (2.81); 3.873 (1.25); 2.4628 (0.36); 2.2903 (0.86); 2.2379 (0.41); 2.2156 (9.8);
2.2059 (2.35); 2.1933 (0.87); 2.1557 (67.19); 2.1195 (0.71); 2.1133 (0.81); 2.107 (0.89); 2.1009 (0.64);
2.0947 (0.38); 1.9639 (6.61); 1.9579 (10.81); 1.952 (49.86); 1.9458 (87.99); 1.9397 (115.26); 1.9335
(78.49); 1.9273 (39.93); 1.9144 (0.54); 1.7742 (0.51); 1.7681 (0.67); 1.762 (0.46); 1.3872 (0.6); 1.285
(0.37); 1.2697 (0.63); 0.1459 (0.79); 0.008 (7.41); −0.0002 (193.97); −0.0086 (6.65); −0.1496 (0.81)
Compound No. B-12, solvent: [CD3CN],
9.6754 (0.96); 8.7832 (1.15); 8.7809 (1.06); 8.7648 (0.95); 8.7623 (0.89); 8.6174 (0.44); 8.477 (1.4);
8.4739 (1.48); 8.4655 (1.47); 8.462 (1.47); 8.2872 (1.15); 8.2828 (1.24); 8.253 (2.78); 8.1069 (1.21);
8.0799 (4.61); 7.9993 (1.41); 7.9955 (1.43); 7.9848 (0.5); 7.9792 (1.55); 7.9754 (1.49); 7.8623 (0.89);
7.859 (0.92); 7.8443 (0.85); 7.8411 (0.84); 7.6886 (2.14); 7.6846 (2.31); 7.6673 (0.68); 7.6529 (0.66);
7.5842 (2.13); 7.517 (1.47); 7.5053 (1.48); 7.4969 (1.45); 7.4851 (1.58); 7.4793 (0.62); 7.1874 (1.97);
6.9502 (0.86); 6.9318 (1.64); 6.9139 (0.83); 5.5516 (4.46); 5.4316 (4.47); 5.0237 (0.45); 5.007 (0.96);
4.9891 (1.09); 4.9714 (0.64); 4.8104 (2.35); 4.7932 (3.8); 4.7755 (2.34); 4.7579 (0.43); 4.5512 (2.41);
4.535 (4.44); 4.519 (2.18); 4.0402 (1.44); 3.984 (0.43); 3.9697 (10.07); 3.9494 (1.67); 3.9331 (16);
3.8733 (1.21); 2.7376 (0.48); 2.7082 (6.65); 2.4701 (0.34); 2.4657 (0.39); 2.3084 (0.35); 2.2916 (1.12);
2.2455 (0.62); 2.2167 (12.78); 2.1629 (857.5); 2.1199 (1.29); 2.1137 (1.54); 2.1075 (1.84); 2.1014
(1.39); 2.0953 (0.79); 1.9997 (0.78); 1.9642 (13.79); 1.9577 (20.27); 1.9524 (106.87); 1.9463 (192.37);
1.9402 (260.8); 1.934 (183.2); 1.9278 (96.85); 1.7805 (0.64); 1.7746 (1.17); 1.7686 (1.56); 1.7624
(1.08); 1.7563 (0.6); 1.3869 (1.65); 1.34 (0.43); 1.2851 (0.69); 1.2695 (1.91); 1.1001 (0.75); 1.0847
(0.69); 0.8806 (0.35); 0.1456 (1.64); 0.0071 (15.72); −0.0003 (332.91); −0.0084 (18.1); −0.15 (1.68)
Compound No. C-01, solvent: [DMSO],
10.1799 (1.03); 8.4767 (0.75); 8.473 (0.81); 8.465 (0.82); 8.4612 (0.8); 8.2048 (2); 8.159 (0.71);
8.1553 (0.73); 8.1389 (0.8); 8.1351 (0.73); 7.6075 (0.76); 7.5957 (0.76); 7.5873 (0.72); 7.5756 (0.72);
7.5423 (0.93); 7.4511 (1.87); 7.3185 (1.76); 6.3204 (2.69); 3.921 (0.36); 3.8904 (6.41); 3.3114
(820.93); 2.674 (0.67); 2.6694 (0.88); 2.6648 (0.69); 2.6606 (0.38); 2.5395 (2.04); 2.5225 (4.54);
2.5092 (49.18); 2.5048 (90.97); 2.5003 (118.63); 2.4959 (83.99); 2.4915 (41.25); 2.3317 (0.58); 2.3271

| 1H NMR data[b] |
|---|

(0.78); 2.3224 (0.57); 2.1605 (3.85); 2.069 (1.3); 1.2363 (0.43); 1.199 (16); 1.1749 (0.54); 1.1629 (0.83); −0.0002 (5.89)
Compound No. C-02, solvent: [DMSO],
10.2951 (2.31); 8.4812 (1.83); 8.4775 (2); 8.4696 (1.95); 8.4657 (1.86); 8.1931 (5.5); 8.1756 (1.19); 8.1567 (1.83); 8.1529 (1.93); 8.1364 (2.04); 8.1326 (1.97); 7.6036 (1.93); 7.5917 (1.81); 7.5833 (1.79); 7.5716 (1.94); 7.5595 (2.45); 7.5294 (2.5); 7.3568 (3.54); 6.3112 (6.38); 4.0676 (0.34); 4.021 (0.33); 3.944 (0.36); 3.8926 (16); 3.8596 (0.39); 3.7884 (0.4); 3.7639 (0.37); 3.7433 (0.35); 3.7316 (0.38); 3.7105 (0.43); 3.6894 (0.45); 3.6762 (0.39); 3.6545 (0.47); 3.629 (0.49); 3.5956 (0.57); 3.5841 (0.55); 3.582 (0.59); 3.5365 (0.67); 3.5218 (0.7); 3.4765 (0.99); 3.4315 (1.37); 3.3053 (2168.99); 3.211 (0.37); 3.1758 (0.39); 3.1626 (0.34); 2.7601 (0.39); 2.7266 (0.42); 2.7204 (0.46); 2.6953 (1.24); 2.6737 (3.11); 2.6688 (4.54); 2.6639 (8.37); 2.6522 (6.57); 2.5391 (8.24); 2.5087 (187.93); 2.5044 (340.66); 2.4999 (438.09); 2.4955 (304.97); 2.4912 (147.28); 2.3313 (1.99); 2.3266 (2.67); 2.3221 (2.04); 2.1623 (9.64); 2.0847 (0.77); 2.0692 (3.52); 1.9869 (0.48); 1.3985 (2.92); 1.237 (0.58); 0.8907 (0.41); −0.0002 (14.46); −0.0083 (0.68)
Compound No. C-03, solvent: [DMSO],
10.1744 (1.06); 8.4766 (0.81); 8.4728 (0.85); 8.4648 (0.81); 8.461 (0.77); 8.1626 (2.12); 8.1561 (0.82); 8.1396 (0.8); 8.1358 (0.73); 7.6075 (0.72); 7.5957 (0.74); 7.5872 (0.76); 7.5754 (0.67); 7.5381 (0.98); 7.4433 (1.02); 7.4058 (1.11); 7.3198 (1.69); 6.3216 (2.86); 5.7471 (3.04); 4.4003 (0.5); 4.385 (0.73); 4.3696 (0.49); 3.4212 (0.37); 3.3658 (0.89); 3.2998 (594.91); 3.276 (13.01); 2.6731 (0.99); 2.6687 (1.3); 2.6642 (0.99); 2.6045 (0.37); 2.5387 (2.38); 2.5083 (76.39); 2.5041 (137.47); 2.4996 (175.7); 2.4953 (123.06); 2.331 (0.9); 2.3263 (1.16); 2.3217 (0.88); 2.16 (3.98); 2.0693 (0.57); 1.27 (0.87); 1.2437 (7.34); 1.2281 (7.09); 1.1959 (16); 1.1747 (0.8); 1.1629 (1.47); −0.0002 (7.12)
Compound No. C-04, solvent: [DMSO],
10.1754 (1.04); 8.4764 (0.8); 8.4726 (0.83); 8.4648 (0.81); 8.4612 (0.84); 8.197 (1.92); 8.1593 (0.69); 8.1558 (0.72); 8.1392 (0.82); 8.1357 (0.62); 7.6073 (0.7); 7.5957 (0.7); 7.5871 (0.64); 7.5753 (0.69); 7.5422 (1.01); 7.4483 (1.14); 7.4302 (1.08); 7.3188 (1.72); 6.3213 (2.77); 4.1812 (0.66); 4.1634 (1.73); 4.1458 (1.76); 4.1281 (0.54); 3.5805 (0.32); 3.5361 (0.33); 3.5195 (0.35); 3.5156 (0.33); 3.5037 (0.36); 3.4386 (0.62); 3.3007 (1159.13); 3.277 (23.4); 3.2469 (0.88); 2.6952 (0.38); 2.6733 (1.7); 2.6686 (2.22); 2.6642 (1.69); 2.6392 (0.41); 2.6117 (0.5); 2.5387 (4.14); 2.5084 (134.75); 2.5041 (242.86); 2.4997 (311); 2.4953 (217.6); 2.4912 (106.98); 2.3355 (0.88); 2.3308 (1.58); 2.3264 (2.16); 2.3218 (1.56); 2.1601 (3.95); 2.0691 (1.1); 1.2582 (1.97); 1.2405 (4.05); 1.2228 (1.92); 1.1974 (16); 1.1625 (1.55); −0.0002 (10.45)
Compound No. C-05, solvent: [CD3CN],
9.9122 (0.49); 8.5044 (1.45); 8.5008 (1.52); 8.4926 (1.56); 8.489 (1.55); 8.0695 (4.63); 8.0383 (1.48); 8.0346 (1.46); 8.018 (1.65); 8.0144 (1.57); 7.6215 (2.1); 7.6177 (2.34); 7.5696 (1.67); 7.5576 (2); 7.5493 (3.55); 7.5375 (1.61); 7.4439 (3); 7.0064 (0.6); 6.987 (0.59); 4.2297 (0.35); 4.213 (0.75); 4.196 (0.82); 4.1923 (0.8); 4.1754 (0.75); 4.1585 (0.38); 3.9742 (0.46); 3.9278 (16); 2.6107 (4.57); 2.5939 (4.52); 2.2222 (0.43); 2.1977 (12.18); 2.1623 (88.77); 2.121 (0.43); 2.1145 (0.47); 2.1081 (0.58); 2.1022 (0.42); 2.0513 (16); 1.9651 (2.49); 1.9532 (28.04); 1.9471 (52.92); 1.9409 (73.97); 1.9347 (51.55); 1.9285 (27.04); 1.7693 (0.43); 1.3867 (0.73); 1.2687 (0.34); 1.2445 (0.36); 1.231 (6.83); 1.2143 (6.79); 0.0071 (1.26); −0.0002 (31.34); −0.0085 (1.68)
Compound No. C-06, solvent: [CD3CN],
9.7348 (0.79); 8.4391 (1.34); 8.4353 (1.45); 8.4274 (1.41); 8.4235 (1.43); 8.0448 (4); 7.9588 (1.4); 7.9549 (1.41); 7.9387 (1.52); 7.9348 (1.5); 7.557 (2.16); 7.5397 (1.96); 7.4512 (1.52); 7.4394 (1.48); 7.4311 (1.41); 7.4193 (1.38); 7.0988 (0.66); 6.48 (2.48); 4.8684 (1.37); 4.8531 (1.43); 4.8378 (1.27); 4.8225 (0.95); 4.8072 (0.38); 3.9372 (0.7); 3.9188 (16); 3.8757 (0.58); 2.7975 (0.4); 2.7882 (0.6); 2.7794 (0.9); 2.7699 (0.93); 2.7612 (0.62); 2.7519 (0.44); 2.2751 (0.47); 2.1934 (12.3); 2.1754 (225.08); 2.114 (0.36); 2.1078 (0.37); 1.9646 (2); 1.9586 (2.38); 1.9527 (18.75); 1.9466 (35.04); 1.9404 (48.68); 1.9342 (33.56); 1.928 (17.22); 1.9154 (0.32); 1.3779 (14.85); 1.3625 (14.75); 0.753 (0.5); 0.7406 (1.48); 0.7356 (2); 0.7229 (2.05); 0.7176 (1.51); 0.7053 (0.67); 0.5558 (0.67); 0.5439 (1.72); 0.5385 (1.75); 0.5342 (1.59); 0.5289 (1.58); 0.5165 (0.48); 0.0081 (0.4); −0.0002 (11.77); −0.0086 (0.36)
Compound No. C-07, solvent: [CD3CN],
9.7865 (0.92); 8.4334 (1.46); 8.4296 (1.36); 8.4217 (1.51); 8.4178 (1.34); 8.0615 (4.26); 7.952 (1.48); 7.9481 (1.31); 7.9319 (1.6); 7.928 (1.38); 7.5882 (2); 7.5845 (2.18); 7.5421 (2.15); 7.4477 (1.5); 7.436 (1.47); 7.4276 (1.38); 7.4158 (1.35); 6.8987 (0.51); 6.8817 (0.5); 6.4658 (2.68); 4.8589 (0.38); 4.8435 (0.97); 4.8282 (1.32); 4.8129 (1); 4.7976 (0.4); 4.1164 (0.55); 4.0999 (0.83); 4.0807 (0.75); 4.064 (0.54); 3.943 (0.75); 3.9247 (16); 3.8721 (0.64); 2.2792 (0.46); 2.1947 (10.81); 2.1685 (0.65); 2.1383 (32.49); 2.1189 (0.36); 2.1128 (0.44); 2.1066 (0.55); 2.1005 (0.34); 1.9635 (2.8); 1.9516 (27.28); 1.9454 (50.01); 1.9392 (67.99); 1.933 (46.41); 1.9269 (23.46); 1.7677 (0.4); 1.3708 (15.3); 1.3555 (15.17); 1.2702 (0.94); 1.1709 (14.77); 1.1544 (14.61); 1.1314 (0.69); 1.1148 (0.64); 0.008 (0.57); −0.0002 (15.64); −0.0086 (0.51)
Compound No. C-08, solvent: [CD3CN],
9.7491 (0.55); 8.4324 (1.4); 8.4286 (1.4); 8.4206 (1.44); 8.4168 (1.39); 8.0713 (4.39); 7.954 (1.41); 7.9502 (1.34); 7.9339 (1.55); 7.93 (1.43); 7.5926 (1.88); 7.5884 (2.17); 7.9495 (1.52); 7.4378 (1.48); 7.4294 (1.41); 7.4176 (1.37); 7.0449 (0.5); 7.0267 (0.51); 6.4645 (2.75); 4.852 (0.4); 4.8367 (0.99); 4.8214 (1.35); 4.806 (1.02); 4.7908 (0.4); 3.9461 (0.66); 3.9282 (16); 3.8692 (0.55); 3.601 (1.13); 3.4665 (0.42); 3.4458 (0.78); 3.4291 (0.79); 3.4084 (0.42); 2.2801 (0.51); 2.1832 (221.87); 2.1205 (0.36); 2.1141 (0.4); 2.1079 (0.43); 1.9648 (2.12); 1.9585 (2.91); 1.9529 (20.52); 1.9467 (37.91); 1.9405 (52.25); 1.9343 (35.89); 1.9282 (18.37); 1.769 (0.32); 1.3872 (0.34); 1.3668 (15.41); 1.3515 (15.27); 1.2203 (6.87); 1.2036 (6.79); 0.9316 (0.41); 0.9192 (0.77); 0.9106 (0.48); 0.9072 (0.49); 0.8987 (0.81); 0.8865 (0.47); 0.8781 (0.36); 0.4828 (0.81); 0.4733 (0.65); 0.4697 (0.63); 0.4616 (0.77); 0.4526 (0.42); 0.4486 (0.43); 0.439 (0.43); 0.4036 (0.38); 0.3935 (0.48); 0.3904 (0.49); 0.3802 (0.68); 0.3707 (0.69); 0.3598 (0.74); 0.3045 (0.5); 0.2945 (0.73); 0.2817 (1.01); 0.2715 (0.94); 0.2589 (0.96); 0.2465 (0.95); 0.2367 (0.87); 0.224 (0.68); 0.2142 (0.42); 0.0079 (0.45); −0.0002 (12.4); −0.0085 (0.4)

| 1H NMR data[b] |
|---|
| Compound No. C-09, solvent: [CD3CN],<br>8.4364 (0.42); 8.4325 (0.42); 8.4245 (0.43); 8.4207 (0.4); 8.13 (0.75); 8.0652 (0.69); 8.0589 (1.58); 7.9573 (0.42); 7.9534 (0.39); 7.9371 (0.46); 7.9333 (0.41); 7.8603 (0.32); 7.5437 (0.91); 7.53 (0.64); 7.452 (0.44); 7.4402 (0.46); 7.4319 (0.41); 7.4201 (0.4); 6.6754 (0.91); 6.4567 (0.86); 4.8528 (0.36); 4.8375 (0.47); 4.8222 (0.46); 3.9398 (2.88); 3.9231 (4.78); 2.1933 (3.11); 2.1371 (18.66); 1.9635 (1.47); 1.9572 (2); 1.9516 (14.04); 1.9455 (26); 1.9393 (35.94); 1.9331 (24.73); 1.9269 (12.64); 1.7862 (1.83); 1.3745 (3.38); 1.37 (4.92); 1.3596 (16); 1.3547 (5.64); −0.0002 (8.44)<br>Compound No. C-10, solvent: [CD3CN],<br>9.8975 (0.9); 8.4375 (1.38); 8.4337 (1.43); 8.4257 (1.44); 8.4219 (1.42); 8.0504 (4.44); 7.953 (1.39); 7.9491 (1.37); 7.9328 (1.54); 7.929 (1.45); 7.5963 (1.98); 7.5922 (2.18); 7.5311 (2.03); 7.4488 (1.51); 7.437 (1.48); 7.4286 (1.41); 7.4168 (1.36); 7.0008 (0.5); 6.4911 (2.67); 4.2854 (1.16); 4.2678 (3.65); 4.2502 (3.69); 4.2326 (1.19); 3.9389 (0.54); 3.9312 (0.62); 3.9208 (16); 3.8728 (0.44); 3.6912 (0.36); 2.8197 (7.35); 2.8077 (7.32); 2.1871 (11.05); 2.1687 (0.36); 2.1354 (8.88); 1.9634 (0.84); 1.9571 (1.14); 1.9515 (7.6); 1.9453 (14.05); 1.9391 (19.47); 1.9329 (13.5); 1.9268 (6.97); 1.405 (3.86); 1.3963 (0.39); 1.3874 (8.05); 1.3698 (3.73); −0.0002 (6.12)<br>Compound No. C-11, solvent: [CD3CN],<br>8.4377 (0.6); 8.4338 (0.64); 8.426 (0.63); 8.4221 (0.63); 8.0523 (1.77); 7.9524 (0.6); 7.9485 (0.6); 7.9322 (0.66); 7.9283 (0.64); 7.5372 (0.71); 7.5331 (0.92); 7.5111 (0.84); 7.4511 (0.64); 7.4393 (0.63); 7.431 (0.6); 7.4192 (0.58); 6.6626 (0.38); 6.5049 (1.26); 4.2774 (0.45); 4.2598 (1.43); 4.2422 (1.45); 4.2247 (0.47); 4.0675 (0.43); 4.0497 (0.43); 3.9232 (6.59); 2.1822 (4.75); 2.1578 (1.05); 2.1463 (1.1); 2.1131 (0.35); 1.9714 (1.99); 1.9636 (0.53); 1.9573 (0.7); 1.9516 (4.72); 1.9454 (8.76); 1.9393 (12.09); 1.9331 (8.49); 1.927 (4.42); 1.4021 (1.53); 1.3845 (3.15); 1.3762 (0.34); 1.3669 (1.71); 1.3548 (16); 1.3168 (1.04); 1.3138 (0.73); 1.2693 (0.39); 1.2212 (0.54); 1.2034 (1.05); 1.1856 (0.53); −0.0002 (3.26)<br>Compound No. C-12, solvent: [CD3CN],<br>9.9421 (1.08); 8.8419 (1.93); 8.4439 (1.53); 8.441 (1.54); 8.4322 (1.53); 8.4293 (1.48); 8.1513 (0.42); 8.1188 (1.2); 8.0964 (1.41); 8.0567 (4.85); 7.9669 (1.48); 7.9641 (1.42); 7.9467 (1.69); 7.9441 (1.55); 7.8271 (2.22); 7.8068 (1.94); 7.608 (2.53); 7.6046 (2.64); 7.5437 (2.58); 7.4665 (1.44); 7.4548 (1.45); 7.4464 (1.34); 7.4347 (1.25); 7.0204 (0.68); 6.5805 (3.11); 6.5106 (0.37); 5.4775 (0.57); 5.4199 (6.97); 3.9387 (0.72); 3.9309 (1.81); 3.9208 (16); 3.8733 (0.4); 3.6871 (1.17); 3.5998 (14.12); 2.8181 (7.78); 2.8062 (7.71); 2.2822 (0.35); 2.1926 (12.7); 2.1692 (0.57); 2.1397 (28.93); 2.112 (0.44); 2.1067 (0.57); 2.1008 (0.38); 2.0016 (1.08); 1.9626 (2.81); 1.951 (30.75); 1.9449 (54.95); 1.9389 (74.31); 1.9328 (51.23); 1.9269 (26.4); 1.7672 (0.42); 1.3869 (0.42); 1.2691 (0.68); −0.0003 (48.29); −0.008 (2.73)<br>Compound No. C-13, solvent: [CD3CN],<br>9.5815 (0.33); 8.835 (0.62); 8.4431 (0.56); 8.4393 (0.55); 8.4313 (0.57); 8.4276 (0.53); 8.1106 (0.35); 8.0909 (0.39); 8.055 (1.75); 7.9649 (0.55); 7.9611 (0.52); 7.9447 (0.6); 7.9409 (0.54); 7.8236 (0.76); 7.8033 (0.65); 7.5422 (0.95); 7.5227 (0.9); 7.4674 (0.57); 7.4556 (0.56); 7.4473 (0.53); 7.4355 (0.51); 6.6323 (0.43); 6.5723 (1.29); 5.416 (2.3); 3.9228 (6.03); 3.5997 (0.61); 2.1844 (4.34); 2.1297 (7.03); 1.9633 (0.66); 1.9515 (8.82); 1.9453 (16.3); 1.9391 (22.62); 1.9329 (15.45); 1.9268 (7.78); 1.3493 (16); 0.0079 (0.71); −0.0002 (14.99); −0.0085 (0.53)<br>Compound No. C-14, solvent: [CD3CN],<br>9.8131 (1.04); 8.8321 (1.98); 8.439 (1.5); 8.4359 (1.57); 8.4274 (1.57); 8.4243 (1.55); 8.107 (1.19); 8.087 (1.28); 8.0672 (4.92); 7.9606 (1.47); 7.9574 (1.49); 7.9405 (1.61); 7.9372 (1.58); 7.8217 (2.26); 7.8014 (1.95); 7.5903 (2.67); 7.5409 (2.58); 7.464 (1.52); 7.4521 (1.49); 7.4439 (1.44); 7.4321 (1.36); 7.0169 (0.79); 6.9973 (0.79); 6.5736 (3.48); 5.4121 (6.99); 3.9456 (0.46); 3.9275 (16); 3.5998 (0.88); 3.4584 (0.48); 3.438 (0.94); 3.421 (0.95); 3.4006 (0.5); 2.1887 (12.65); 2.1618 (0.39); 2.131 (20.98); 2.1137 (0.52); 2.1066 (0.45); 2.1004 (0.32); 1.9627 (1.43); 1.9513 (19.37); 1.9452 (36.03); 1.9391 (50.14); 1.933 (35.17); 1.9269 (18.41); 1.2132 (7.14); 1.1965 (7.11); 0.9263 (0.46); 0.914 (0.88); 0.9024 (0.64); 0.8934 (0.92); 0.8813 (0.57); 0.8726 (0.37); 0.4842 (0.38); 0.4752 (0.88); 0.4628 (0.82); 0.4536 (0.92); 0.445 (0.51); 0.4415 (0.53); 0.4315 (0.45); 0.3914 (0.4); 0.3788 (0.62); 0.3685 (0.8); 0.359 (0.87); 0.3479 (0.89); 0.3396 (0.37); 0.3267 (0.34); 0.2942 (0.61); 0.2838 (0.81); 0.2714 (1.22); 0.2607 (1.12); 0.25 (0.99); 0.239 (1.16); 0.2291 (1.07); 0.2168 (0.79); 0.2061 (0.48); −0.0002 (34.29)<br>Compound No. C-15, solvent: [CD3CN],<br>8.8359 (1.82); 8.4399 (1.47); 8.4363 (1.44); 8.4282 (1.55); 8.4245 (1.45); 8.1117 (1.01); 8.0952 (1.18); 8.0579 (4.85); 7.961 (1.48); 7.9574 (1.41); 7.9409 (1.61); 7.9372 (1.47); 7.8253 (2.14); 7.805 (1.86); 7.5808 (2.54); 7.5355 (2.44); 7.4642 (1.5); 7.4524 (1.48); 7.444 (1.41); 7.4323 (1.36); 6.9082 (0.68); 6.8887 (0.7); 6.5848 (3.24); 5.4158 (6.65); 4.1064 (0.59); 4.0897 (0.9); 4.0719 (0.86); 4.0548 (0.58); 3.9426 (0.61); 3.9243 (16); 3.8718 (0.5); 3.6004 (3.98); 2.2729 (0.61); 2.1877 (13.46); 2.1612 (177.36); 2.115 (0.49); 2.1076 (0.53); 2.1012 (0.38); 1.9642 (0.94); 1.9524 (15.09); 1.9462 (28.34); 1.9401 (39.6); 1.9339 (27.32); 1.9277 (14.17); 1.1623 (14.79); 1.1458 (14.65); 1.1307 (0.73); 1.1141 (0.6); 0.0077 (1.27); −0.0002 (27.69); −0.0084 (1.12)<br>Compound No. C-16, solvent: [CD3CN],<br>9.8042 (0.76); 8.8417 (1.87); 8.4444 (1.57); 8.4407 (1.57); 8.4326 (1.63); 8.429 (1.55); 8.1217 (1.04); 8.1018 (1.16); 8.0374 (4.63); 7.9663 (1.54); 7.9626 (1.49); 7.9461 (1.68); 7.9424 (1.57); 7.8278 (2.17); 7.8077 (1.85); 7.5473 (2.67); 7.5274 (2.57); 7.4662 (1.56); 7.4544 (1.55); 7.4461 (1.47); 7.4343 (1.4); 7.1347 (0.98); 6.6065 (3.2); 5.4219 (6.56); 3.9431 (0.34); 3.9361 (0.7); 3.9177 (16); 3.8748 (0.46); 3.6013 (6.73); 2.7869 (0.47); 2.7777 (0.74); 2.7689 (1.06); 2.7595 (1.06); 2.7507 (0.76); 2.7414 (0.52); 2.3038 (0.4); 2.2821 (0.41); 2.2716 (0.79); 2.2052 (258.22); 2.1832 (14.65); 1.9654 (0.79); 1.9536 (10.48); 1.9475 (19.41); 1.9413 (26.99); 1.9351 (18.84); 1.929 (9.83); 0.7443 (0.61); 0.7311 (1.92); 0.7264 (2.41); 0.7137 (2.49); 0.7086 (1.9); 0.6964 (0.83); 0.5474 (0.81); 0.5361 (2.25); 0.5299 (2.36); 0.5207 (2.04); 0.5082 (0.69); −0.0002 (18.9)<br>Compound No. C-17, solvent: [CD3CN],<br>9.8082 (0.95); 8.4558 (1.61); 8.4526 (1.68); 8.4443 (1.6); 8.441 (1.56); 8.2539 (0.35); 8.0458 (4.68); 7.9716 (1.54); 7.9687 (1.54); 7.9516 (1.62); 7.9485 (1.58); 7.5646 (2.86); 7.5433 (2.68); 7.4737 (1.55); 7.4619 (1.54); 7.4536 (1.43); 7.4418 (1.31); 7.1015 (0.93); 6.5822 (3.18); 6.3749 (0.34); 6.3661 (0.63); 6.2383 (0.71); 6.2292 (1.31); 6.2203 (0.66); 6.1014 (0.34); 6.0922 (0.65); 6.0833 (0.32); 4.5215 (1.32); 4.5125 (1.34); 4.4857 (2.63); 4.4767 (2.56); 4.4498 (1.31); 4.4408 (1.24); 3.9694 (1.4); 3.9368 (0.88); 3.9193 (16); 3.8756 (0.58); 2.797 (0.52); 2.7877 (0.82); 2.7788 (1.13); 2.7693 (1.14); 2.7604 (0.83); |

| 1H NMR data[b] |
| --- |
| 2.7516 (0.54); 2.7091 (0.87); 2.4614 (0.33); 2.2759 (0.47); 2.1937 (12.68); 2.1754 (0.92); 2.1429 (49.23); 2.1184 (0.43); 2.1128 (0.54); 2.1068 (0.61); 2.1008 (0.42); 1.9628 (3.24); 1.9516 (31.54); 1.9455 (57.29); 1.9394 (77.91); 1.9333 (54.24); 1.9271 (28.11); 1.7739 (0.35); 1.7681 (0.46); 1.4373 (0.96); 1.3872 (0.36); 1.2695 (0.42); 0.7528 (0.65); 0.7398 (2.09); 0.7354 (2.64); 0.7225 (2.71); 0.7176 (2.13); 0.7054 (0.9); 0.558 (0.9); 0.5466 (2.53); 0.5406 (2.61); 0.5371 (2.42); 0.5315 (2.24); 0.5189 (0.7); −0.0002 (6.44) |
| Compound No. C-19, solvent: [CD3CN], |
| 8.4491 (1.44); 8.4456 (1.5); 8.4374 (1.5); 8.4338 (1.5); 8.0645 (4.61); 7.9697 (1.43); 7.966 (1.43); 7.9495 (1.56); 7.9458 (1.54); 7.587 (2.06); 7.5829 (2.45); 7.5462 (2.32); 7.4739 (1.51); 7.4621 (1.5); 7.4537 (1.43); 7.442 (1.37); 6.9618 (0.56); 6.9443 (0.58); 6.5823 (2.95); 6.364 (0.6); 6.355 (0.33); 6.2362 (0.63); 6.2272 (1.26); 6.2181 (0.65); 6.0903 (0.64); 6.0813 (0.32); 4.5148 (1.17); 4.5057 (1.19); 4.4788 (2.43); 4.4698 (2.4); 4.4429 (1.25); 4.4338 (1.19); 4.1095 (0.56); 4.0929 (0.84); 4.0742 (0.86); 4.0576 (0.6); 4.0409 (0.33); 3.9709 (0.65); 3.9433 (0.76); 3.9256 (16); 3.8726 (0.63); 3.6026 (3.12); 2.2483 (399.27); 2.1948 (13); 2.1687 (1.18); 2.1222 (0.49); 2.1162 (0.55); 2.11 (0.61); 2.1037 (0.52); 2.0975 (0.38); 1.9667 (1.52); 1.9549 (19.53); 1.9488 (36.28); 1.9426 (50.38); 1.9364 (35.03); 1.9303 (18.23); 1.771 (0.36); 1.2097 (0.46); 1.1943 (0.51); 1.1665 (14.99); 1.15 (14.84); 1.1277 (0.74); 1.1112 (0.7); −0.0002 (4.37) |
| Compound No. C-20, solvent: [CD3CN], |
| 9.9347 (0.66); 8.4511 (1.1); 8.4473 (1.09); 8.4393 (1.12); 8.4356 (1.08); 8.0549 (3.53); 7.9703 (1.09); 7.9666 (1.04); 7.9502 (1.21); 7.9464 (1.11); 7.6041 (1.65); 7.5999 (1.79); 7.5391 (1.24); 7.4715 (1.15); 7.4597 (1.13); 7.4513 (1.06); 7.4395 (1.02); 7.0201 (0.39); 6.5732 (1.97); 6.363 (0.46); 6.2351 (0.47); 6.2261 (0.94); 6.217 (0.46); 6.0892 (0.47); 4.5165 (0.91); 4.5074 (0.92); 4.4806 (1.88); 4.4715 (1.85); 4.4447 (0.96); 4.4356 (0.91); 3.9393 (0.65); 3.9324 (0.34); 3.9219 (12.83); 3.8731 (0.56); 3.5997 (16); 2.8203 (6.16); 2.8083 (6.11); 2.2804 (0.39); 2.1908 (9.04); 2.1694 (0.52); 2.1474 (12.32); 1.9636 (0.56); 1.9518 (8.04); 1.9456 (15.1); 1.9394 (21.2); 1.9333 (14.55); 1.9271 (7.47); −0.0002 (1.9) |
| Compound No. C-21, solvent: [CD3CN], |
| 8.451 (0.61); 8.4471 (0.6); 8.4392 (0.62); 8.4354 (0.57); 8.056 (1.74); 7.9687 (0.57); 7.9649 (0.55); 7.9486 (0.61); 7.9447 (0.56); 7.5468 (0.72); 7.5431 (0.9); 7.5238 (0.83); 7.4728 (0.63); 7.461 (0.59); 7.4527 (0.55); 7.4409 (0.53); 6.6671 (0.38); 6.5854 (1.22); 6.2227 (0.48); 4.511 (0.44); 4.5019 (0.46); 4.4751 (0.91); 4.466 (0.91); 4.4392 (0.46); 4.4301 (0.45); 3.9701 (0.35); 3.9417 (0.49); 3.9236 (6.13); 3.5996 (8.28); 2.1868 (4.2); 2.1476 (0.53); 2.1323 (0.44); 1.9712 (0.43); 1.9634 (0.5); 1.9514 (6.92); 1.9453 (12.92); 1.9391 (18.19); 1.933 (12.59); 1.9268 (6.48); 1.3575 (16); 1.3352 (1.9); 1.3145 (0.38); 1.3052 (0.58); 1.2821 (0.33); 1.2694 (0.51); 1.212 (0.7); 1.2036 (0.32); −0.0002 (1.59) |
| Compound No. C-22, solvent: [CD3CN], |
| 9.9104 (0.58); 8.4456 (1.06); 8.4417 (1.12); 8.4338 (1.11); 8.4299 (1.12); 8.1517 (0.35); 8.0552 (3.42); 7.954 (1.12); 7.9377 (1.24); 7.9338 (1.23); 7.605 (1.1); 7.6006 (1.57); 7.5412 (1.42); 7.4558 (1.23); 7.444 (1.2); 7.4356 (1.13); 7.4239 (1.1); 6.9963 (0.35); 6.5078 (2.02); 6.4481 (0.45); 5.4462 (0.71); 4.0676 (0.68); 4.0497 (0.68); 3.9758 (1.59); 3.9391 (0.94); 3.9282 (13.47); 3.921 (13.78); 3.876 (0.39); 3.8732 (0.66); 3.6947 (1.36); 3.5997 (16); 2.8205 (6.2); 2.8085 (6.17); 2.7912 (0.33); 2.2813 (0.4); 2.1918 (8.38); 2.1701 (0.4); 2.1315 (7.69); 1.998 (0.87); 1.9714 (3.12); 1.9634 (1.36); 1.9573 (1.78); 1.9515 (14.29); 1.9454 (26.49); 1.9392 (36.68); 1.933 (24.94); 1.9268 (12.67); 1.3872 (0.44); 1.2693 (0.36); 1.2213 (0.81); 1.2035 (1.62); 1.1856 (0.81); −0.0002 (1.24) |
| Compound No. C-23, solvent: [CD3CN], |
| 9.7819 (0.66); 8.4497 (1.31); 8.4458 (1.33); 8.4379 (1.32); 8.434 (1.3); 8.043 (3.93); 7.9583 (1.36); 7.9544 (1.32); 7.9381 (1.44); 7.9342 (1.36); 7.5638 (1.5); 7.5595 (1.98); 7.5392 (1.82); 7.4568 (1.48); 7.445 (1.43); 7.4367 (1.33); 7.4249 (1.29); 7.0829 (0.58); 6.5206 (2.42); 3.9655 (0.4); 3.9592 (0.34); 3.9329 (15.47); 3.9259 (1.02); 3.9185 (16); 3.8753 (0.69); 3.8696 (0.35); 3.5997 (3.73); 2.7948 (0.4); 2.7856 (0.6); 2.7767 (0.91); 2.7673 (0.91); 2.7585 (0.62); 2.7492 (0.44); 2.2751 (0.5); 2.1908 (9.68); 2.1754 (0.48); 2.1308 (8.44); 2.1066 (0.33); 1.9634 (1.99); 1.9573 (2.43); 1.9515 (19.73); 1.9454 (36.66); 1.9392 (50.86); 1.933 (34.61); 1.9268 (17.58); 1.3873 (0.33); 1.2694 (0.46); 0.7515 (0.5); 0.7388 (1.44); 0.7337 (1.92); 0.721 (2); 0.71158 (1.43); 0.7035 (0.72); 0.5559 (0.67); 0.5442 (1.62); 0.5385 (1.67); 0.5341 (1.52); 0.529 (1.53); 0.5167 (0.52); −0.0002 (1.76) |
| Compound No. C-24, solvent: [CD3CN], |
| 9.8246 (0.38); 8.4444 (0.82); 8.4406 (0.78); 8.4327 (0.83); 8.4288 (0.75); 8.0618 (2.41); 7.9532 (0.82); 7.9495 (0.76); 7.9331 (0.88); 7.9293 (0.77); 7.5916 (1.07); 7.5873 (1.15); 7.5449 (1.11); 7.4548 (0.87); 7.4431 (0.85); 7.4347 (0.8); 7.4229 (0.76); 6.5097 (1.57); 4.0965 (0.44); 4.0797 (0.41); 4.0771 (0.41); 3.9427 (0.57); 3.9385 (0.33); 3.9252 (16); 3.8721 (0.36); 3.5998 (2.19); 2.1936 (6.03); 2.1297 (8.35); 2.1065 (0.36); 1.9712 (0.42); 1.9634 (1.89); 1.9571 (2.6); 1.9515 (20.48); 1.9454 (37.94); 1.9392 (52.49); 1.933 (35.69); 1.9268 (18.11); 1.2704 (0.46); 1.1707 (8.27); 1.1542 (8.25); 1.1319 (0.51); 1.1266 (0.35); 1.1154 (0.44); −0.0002 (1.69) |
| Compound No. C-25, solvent: [CD3CN], |
| 8.4429 (1.4); 8.4392 (1.35); 8.4311 (1.42); 8.4275 (1.32); 8.0702 (4.24); 7.953 (1.38); 7.9493 (1.28); 7.9329 (1.49); 7.9291 (1.33); 7.5963 (2); 7.5925 (2.16); 7.5471 (2.08); 7.4545 (1.43); 7.4427 (1.41); 7.4344 (1.32); 7.4226 (1.24); 7.0702 (0.57); 7.0504 (0.54); 6.5266 (2.81); 3.9459 (1.18); 3.9409 (0.84); 3.9277 (16); 3.9205 (15.37); 3.8811 (0.61); 3.8686 (0.66); 3.5998 (3.29); 3.4632 (0.43); 3.4424 (0.79); 3.4257 (0.83); 3.405 (0.44); 2.2807 (0.56); 2.194 (11.11); 2.1643 (0.97); 2.1561 (0.66); 2.1358 (0.9); 2.1193 (0.76); 2.113 (0.77); 2.1067 (0.81); 2.1006 (0.64); 2.0943 (0.46); 1.9634 (2.58); 1.9515 (23.5); 1.9454 (42.63); 1.9393 (58.25); 1.9331 (39.69); 1.9269 (20.19); 1.7677 (0.32); 1.2981 (1.04); 1.2817 (1.08); 1.2701 (0.45); 1.2213 (6.62); 1.2046 (6.55); 1.1806 (0.52); 1.1644 (0.39); 0.946 (0.37); 0.9374 (0.5); 0.9254 (0.87); 0.9166 (0.58); 0.9136 (0.57); 0.9049 (0.87); 0.8927 (0.53); 0.8839 (0.4); 0.4964 (0.34); 0.4931 (0.35); 0.4841 (0.8); 0.4745 (0.7); 0.4712 (0.68); 0.4628 (0.82); 0.4539 (0.45); 0.4498 (0.48); 0.4404 (0.47); 0.4042 (0.42); 0.3937 (0.56); 0.3909 (0.56); 0.3808 (0.75); 0.3717 (0.83); 0.3603 (0.88); 0.3489 (0.41); 0.3392 (0.37); 0.3048 (0.53); 0.2948 (0.78); 0.2822 (1.09); 0.2717 (1.09); 0.2587 (1); 0.2458 (1.06); 0.2358 (1.01); 0.2232 (0.75); 0.213 (0.48); −0.0002 (1.88) |
| Compound No. C-26, solvent: [CD3CN], |
| 8.4453 (0.59); 8.4416 (0.55); 8.4335 (0.61); 8.4299 (0.53); 8.0562 (1.68); 7.9561 (0.55); 7.9524 (0.54); 7.936 (0.59); 7.9323 (0.56); 7.541 (0.98); 7.5245 (0.93); 7.4569 (0.6); 7.4451 (0.57); 7.4368 (0.55); |

| 1H NMR data[b] |
|---|

7.425 (0.51); 6.6816 (0.41); 6.5373 (1.21); 3.923 (11.21); 3.9001 (0.58); 3.5997 (3.38); 2.1903 (4.38); 2.1487 (0.66); 2.1193 (0.33); 1.9713 (0.68); 1.9633 (1.11); 1.9515 (9.93); 1.9453 (17.93); 1.9392 (24.26); 1.933 (16.62); 1.9269 (8.49); 1.3554 (16); 1.347 (6.04); 1.305 (0.43); 1.2965 (0.35); 1.2704 (0.33); −0.0002 (0.74)

Compound No. C-27, solvent: [CD3CN],
9.7896 (0.87); 8.4347 (1.38); 8.4312 (1.46); 8.423 (1.43); 8.4195 (1.43); 8.0665 (4.83); 7.9491 (1.41); 7.9455 (1.4); 7.929 (1.54); 7.9253 (1.49); 7.5885 (2.12); 7.5849 (2.41); 7.5352 (2.29); 7.4486 (1.53); 7.4368 (1.5); 7.4285 (1.42); 7.4167 (1.37); 7.04 (0.59); 7.0207 (0.6); 6.4899 (3.27); 4.2756 (1.21); 4.2581 (3.75); 4.2405 (3.78); 4.2229 (1.24); 3.9455 (0.67); 3.9278 (16); 3.8684 (0.48); 3.4628 (0.43); 3.4422 (0.84); 3.4254 (0.85); 3.4049 (0.46); 2.2761 (0.37); 2.1878 (12.02); 2.1524 (22.5); 1.9635 (1.1); 1.9569 (1.51); 1.9517 (10); 1.9456 (18.45); 1.9394 (25.57); 1.9332 (17.75); 1.9271 (9.22); 1.3997 (3.92); 1.3821 (7.86); 1.3645 (3.81); 1.2181 (6.89); 1.2014 (6.8); 0.9308 (0.42); 0.9185 (0.81); 0.9098 (0.52); 0.9066 (0.56); 0.8979 (0.87); 0.8858 (0.49); 0.8775 (0.35); 0.4924 (0.34); 0.4834 (0.84); 0.4737 (0.71); 0.4707 (0.73); 0.4617 (0.84); 0.453 (0.43); 0.4494 (0.47); 0.4397 (0.44); 0.4038 (0.37); 0.3933 (0.51); 0.3911 (0.52); 0.3807 (0.73); 0.3711 (0.77); 0.3599 (0.81); 0.3035 (0.55); 0.2931 (0.76); 0.2806 (1.11); 0.2701 (1.01); 0.2582 (1.02); 0.2461 (1.05); 0.2363 (0.96); 0.2236 (0.73); 0.2132 (0.44); −0.0002 (7.08)

Compound No. C-28, solvent: [CD3CN],
10.0432 (0.72); 8.4952 (1.33); 8.4914 (1.39); 8.4834 (1.37); 8.4797 (1.39); 8.1556 (0.4); 8.0937 (0.54); 8.062 (3.93); 8.0174 (1.36); 8.0136 (1.4); 7.9971 (1.56); 7.9934 (1.5); 7.6199 (1.6); 7.6155 (1.86); 7.5547 (1.71); 7.5439 (1.65); 7.5321 (1.49); 7.5236 (1.46); 7.5118 (1.33); 7.3076 (1.77); 7.0781 (0.96); 7.0162 (0.5); 6.9419 (1.98); 6.8056 (0.98); 4.0677 (0.58); 4.0499 (0.61); 3.9775 (0.46); 3.9696 (0.36); 3.9393 (2.14); 3.9346 (1.98); 3.9242 (16); 3.9144 (0.45); 3.8733 (1.3); 3.7063 (1.43); 2.8294 (0.34); 2.8186 (7.34); 2.8066 (7.22); 2.7986 (0.58); 2.7921 (0.67); 2.7863 (0.59); 2.7801 (0.62); 2.7543 (0.46); 2.7422 (0.45); 2.2824 (0.98); 2.2246 (0.4); 2.1998 (9.79); 2.1701 (0.99); 2.1383 (50.25); 2.1193 (0.44); 2.113 (0.55); 2.1068 (0.65); 2.1006 (0.44); 1.992 (0.99); 1.9715 (3.15); 1.9637 (5.3); 1.9576 (8.54); 1.9517 (39.79); 1.9456 (70.13); 1.9394 (92.57); 1.9332 (63.41); 1.927 (32.47); 1.9142 (0.37); 1.7739 (0.38); 1.7678 (0.54); 1.7616 (0.34); 1.3872 (0.53); 1.285 (0.48); 1.2694 (0.96); 1.2214 (0.73); 1.2036 (1.45); 1.1857 (0.71); 0.1459 (0.58); 0.0782 (0.54); 0.008 (5.44); −0.0002 (140.62); −0.0086 (4.67); −0.1498 (0.58)

Compound No. C-29, solvent: [CD3CN],
9.9538 (0.82); 8.4894 (1.33); 8.4857 (1.36); 8.4776 (1.34); 8.4739 (1.33); 8.098 (0.33); 8.063 (4.25); 8.0115 (1.31); 8.0078 (1.29); 7.9913 (1.43); 7.9875 (1.42); 7.593 (1.71); 7.5886 (2); 7.5399 (3.03); 7.5281 (1.43); 7.5197 (1.34); 7.5079 (1.28); 7.3227 (1.84); 7.0753 (0.97); 6.939 (2.35); 6.9305 (0.55); 6.913 (0.46); 6.8028 (1.01); 4.1051 (0.6); 4.0886 (0.75); 4.0861 (0.65); 4.0693 (0.78); 4.0528 (0.55); 3.9738 (0.49); 3.9695 (0.69); 3.9428 (1.35); 3.9275 (16); 3.8716 (0.49); 2.7081 (0.37); 2.2757 (0.73); 2.2199 (0.52); 2.194 (14.7); 2.1793 (62.7); 1.9645 (2.27); 1.9585 (3.72); 1.9526 (17.72); 1.9465 (31.13); 1.9403 (40.93); 1.9341 (27.95); 1.9279 (14.34); 1.2691 (1.07); 1.158 (14.86); 1.1415 (14.76); 1.1297 (1.15); 1.1132 (1.06); 0.0079 (1.9); −0.0002 (54.74); −0.0085 (1.87)

Compound No. C-30, solvent: [CD3CN],
9.9135 (0.66); 8.0822 (3.82); 7.5947 (1.51); 7.5903 (1.71); 7.533 (1.57); 7.496 (0.79); 7.4907 (1.01); 7.4851 (0.95); 7.4836 (0.94); 7.478 (1.5); 7.4722 (1.65); 7.4676 (1.65); 7.4389 (0.55); 7.4271 (1.96); 7.4237 (1.89); 7.4203 (1.29); 7.4135 (2.12); 7.4066 (1.03); 7.4026 (1); 7.4005 (1.04); 7.0522 (0.35); 6.5002 (2.86); 3.9735 (0.63); 3.9292 (0.43); 3.9198 (16); 3.9134 (15.61); 3.5996 (3.4); 2.807 (6.74); 2.795 (6.63); 2.2558 (0.33); 2.1886 (15.64); 1.9636 (1.55); 1.9625 (2.5); 1.9516 (11.67); 1.9455 (20.49); 1.9393 (26.93); 1.9331 (18.36); 1.9269 (9.37); 1.387 (0.51); 0.549 (0.73); 0.5385 (1.76); 0.5316 (1.78); 0.5273 (1.56); 0.5222 (1.62); 0.5098 (0.63); 0.1461 (0.59); 0.0081 (5.24); −0.0002 (140.38); −0.0086 (4.3); −0.1495 (0.6)

Compound No. C-32, solvent: [CD3CN],
9.853 (0.81); 8.0587 (4.03); 7.5855 (1.59); 7.5811 (1.88); 7.5361 (1.72); 7.4885 (1.25); 7.4819 (1.06); 7.4763 (1.31); 7.4742 (0.98); 7.471 (1.56); 7.4642 (2.56); 7.4383 (0.57); 7.4264 (1.94); 7.4224 (2.11); 7.4195 (1.23); 7.4126 (1.95); 7.4052 (1.06); 7.402 (1); 7.3992 (0.97); 6.9447 (0.43); 6.9249 (0.43); 6.5065 (3.07); 4.103 (0.51); 4.0865 (0.71); 4.084 (0.61); 4.0699 (0.6); 4.0673 (0.72); 4.0508 (0.5); 3.9709 (0.33); 3.9429 (0.37); 3.9237 (15.95); 3.9109 (16); 3.5997 (1.29); 2.1872 (9.81); 2.1374 (18.76); 1.9634 (2.28); 1.9573 (3.74); 1.9514 (17.28); 1.9453 (30.44); 1.9391 (39.92); 1.9329 (27.27); 1.9268 (14); 1.2827 (0.57); 1.2667 (0.8); 1.1677 (13.89); 1.1512 (13.71); 0.008 (2.34); −0.0002 (61.71); −0.0086 (2.09)

Compound No. C-33, solvent: [CD3CN],
9.9035 (0.66); 8.0522 (3.82); 7.5947 (1.51); 7.5903 (1.71); 7.533 (1.57); 7.496 (0.79); 7.4907 (1.01); 7.4851 (0.95); 7.4836 (0.94); 7.478 (1.5); 7.4722 (1.65); 7.4676 (1.65); 7.4389 (0.55); 7.4271 (1.96); 7.4237 (1.89); 7.4203 (1.29); 7.4135 (2.12); 7.4066 (1.03); 7.4026 (1); 7.4005 (1.04); 7.0522 (0.35); 6.5002 (2.86); 3.9735 (0.63); 3.9292 (0.43); 3.9198 (16); 3.9134 (15.61); 3.5996 (3.4); 2.807 (6.74); 2.795 (6.63); 2.2558 (0.33); 2.1886 (15.64); 1.9636 (1.55); 1.9575 (2.5); 1.9516 (11.67); 1.9455 (20.49); 1.9393 (26.93); 1.9331 (18.36); 1.9269 (9.37); 1.387 (0.51); 0.008 (1.42); −0.0002 (37.41); −0.0087 (1.14)

Compound No. C-34, solvent: [CD3CN],
9.9159 (0.82); 8.4979 (1.43); 8.4941 (1.41); 8.4861 (1.58); 8.4823 (1.36); 8.0831 (0.38); 8.0758 (0.52); 8.0492 (3.87); 8.0181 (1.45); 8.0143 (1.4); 7.9979 (1.81); 7.9941 (1.51); 7.6031 (0.47); 7.576 (1.62); 7.5718 (2.09); 7.5508 (2.05); 7.5444 (2.38); 7.5325 (1.52); 7.524 (1.42); 7.5122 (1.36); 7.3235 (1.86); 7.1055 (0.6); 7.0845 (1.09); 6.9482 (1.99); 6.8119 (0.97); 3.9699 (0.99); 3.9458 (0.35); 3.937 (1.58); 3.931 (2.34); 3.9216 (16); 3.8754 (1.01); 2.7911 (0.44); 2.782 (0.64); 2.7729 (0.99); 2.7636 (1); 2.7547 (0.72); 2.7454 (0.49); 2.276 (0.7); 2.2217 (0.37); 2.1992 (10.52); 2.1751 (1.32); 2.1487 (62.77); 2.1195 (0.43); 2.1132 (0.54); 2.107 (0.64); 2.1009 (0.44); 1.9639 (5.4); 1.9579 (8.86); 1.952 (40.41); 1.9458 (71.26); 1.9397 (93.3); 1.9335 (63.37); 1.9273 (32.1); 1.9145 (0.4); 1.7743 (0.4); 1.7681 (0.54); 1.7619 (0.36); 1.3873 (0.45); 1.27 (0.61); 1.2126 (0.78); 1.1958 (0.77); 0.7483 (0.57); 0.7355 (1.62); 0.7304 (2.06); 0.7177 (2.15); 0.7124 (1.52); 0.7004 (0.71); 0.549 (0.73); 0.5385 (1.76); 0.5316 (1.78); 0.5273

| 1H NMR data[b] |
|---|

(1.56); 0.5222 (1.62); 0.5098 (0.63); 0.1461 (0.59); 0.0081 (5.24); −0.0002 (140.38); −0.0086 (4.3); −0.1495 (0.6)

Compound No. C-35, solvent: [CD3CN],
8.4902 (0.52); 8.4863 (0.52); 8.4784 (0.53); 8.4746 (0.5); 8.0584 (1.53); 8.014 (0.51); 8.0102 (0.5); 7.9938 (0.56); 7.99 (0.52); 7.5502 (0.6); 7.5457 (0.78); 7.5413 (0.68); 7.5294 (0.63); 7.5211 (1.1); 7.5092 (0.51); 7.3379 (0.71); 7.0735 (0.35); 6.9373 (0.73); 6.801 (0.36); 3.9705 (0.45); 3.9418 (0.46); 3.9265 (6.11); 3.8891 (0.34); 2.2496 (0.32); 2.1876 (4.02); 2.1511 (1.17); 2.1192 (0.53); 2.1129 (0.49); 2.1067 (0.47); 2.1005 (0.36); 1.9636 (1.68); 1.9575 (2.69); 1.9516 (12.41); 1.9455 (21.79); 1.9393 (28.57); 1.9331 (19.45); 1.9269 (9.9); 1.3544 (1.45); 1.3453 (16); 1.3146 (0.35); 1.2955 (0.38); 0.008 (1.82); −0.0002 (49.02); −0.0086 (1.54)

Compound No. C-36, solvent: [CD3CN],
9.9379 (0.83); 8.4891 (1.41); 8.4854 (1.5); 8.4773 (1.44); 8.4736 (1.44); 8.1103 (0.53); 8.0756 (4.32); 8.0124 (1.45); 8.0087 (1.45); 7.9922 (1.74); 7.9885 (1.58); 7.6228 (0.37); 7.6073 (2.15); 7.603 (2.28); 7.5581 (2.14); 7.5407 (1.57); 7.5289 (1.51); 7.5204 (1.43); 7.5086 (1.42); 7.3258 (2.03); 7.0708 (1.43); 7.0482 (0.52); 6.9346 (2.16); 6.7983 (1.07); 3.9777 (0.67); 3.9699 (0.43); 3.9465 (1.97); 3.9308 (16); 3.9187 (0.41); 3.8765 (1.07); 3.4547 (0.46); 3.4337 (0.85); 3.417 (0.88); 3.3963 (0.47); 2.3599 (0.5); 2.3194 (0.96); 2.286 (2.83); 2.2219 (12.7); 2.2018 (18.42); 2.1322 (0.74); 2.1192 (0.81); 2.1131 (0.97); 2.1069 (1.09); 2.1008 (0.84); 2.0945 (0.59); 2.083 (0.38); 1.9637 (7.44); 1.9575 (12.59); 1.9518 (51.76); 1.9457 (90.76); 1.9395 (118.24); 1.9334 (81.72); 1.9272 (42.42); 1.78 (0.34); 1.774 (0.52); 1.768 (0.69); 1.7618 (0.47); 1.3872 (0.48); 1.3623 (0.44); 1.3457 (0.41); 1.27 (0.6); 1.2126 (7.21); 1.1959 (7.1); 1.1837 (0.78); 1.1723 (0.36); 1.1668 (0.67); 0.9362 (0.33); 0.9281 (0.45); 0.9153 (0.82); 0.9072 (0.57); 0.9033 (0.61); 0.8948 (0.9); 0.8822 (0.58); 0.8743 (0.43); 0.4856 (0.33); 0.4821 (0.41); 0.4732 (0.91); 0.4638 (0.72); 0.4601 (0.76); 0.4522 (0.84); 0.4431 (0.53); 0.439 (0.58); 0.4295 (0.53); 0.381 (0.47); 0.371 (0.53); 0.3676 (0.54); 0.3575 (0.78); 0.3479 (0.78); 0.3372 (0.91); 0.3288 (0.37); 0.3253 (0.4); 0.3163 (0.4); 0.3014 (0.36); 0.2884 (0.59); 0.2783 (0.79); 0.2656 (1.17); 0.2557 (1.11); 0.2482 (0.86); 0.2432 (0.81); 0.2399 (0.86); 0.2359 (1.19); 0.2269 (0.99); 0.2138 (0.73); 0.2041 (0.47); 0.1457 (0.81); 0.0075 (7.48); −0.0002 (163.49); −0.0084 (8.04); −0.1499 (0.79)

Compound No. C-37, solvent: [CD3CN],
8.0572 (1.52); 7.5501 (0.6); 7.5458 (0.78); 7.5259 (0.7); 7.4962 (0.33); 7.4836 (0.64); 7.4723 (0.85); 7.4652 (0.4); 7.4594 (0.68); 7.4296 (0.99); 7.4279 (0.9); 7.4225 (0.62); 7.4169 (0.7); 7.4114 (0.45); 7.4048 (0.62); 6.5022 (1.1); 4.0678 (0.51); 4.05 (0.51); 3.9419 (0.6); 3.9225 (6.27); 3.9097 (6.09); 3.8755 (0.59); 3.8722 (0.57); 3.8568 (0.35); 2.2699 (0.35); 2.2069 (0.5); 2.1835 (5.03); 2.1566 (9.65); 2.1133 (0.45); 2.1071 (0.42); 1.9717 (2.39); 1.9639 (1.41); 1.9579 (2.19); 1.952 (11.92); 1.9459 (21.38); 1.9397 (28.48); 1.9335 (19.4); 1.9273 (9.89); 1.3528 (16); 1.3133 (1.33); 1.2906 (1.08); 1.2697 (0.49); 1.2322 (0.39); 1.2214 (0.64); 1.2036 (1.26); 1.1858 (0.63); 0.9653 (0.7); 0.0081 (1.44); −0.0002 (38.3); −0.0086 (1.18)

Compound No. C-38, solvent: [CD3CN],
8.4521 (1.36); 8.4482 (1.39); 8.4402 (1.41); 8.4364 (1.38); 8.0415 (3.96); 7.9804 (1.34); 7.9765 (1.31); 7.9603 (1.47); 7.9564 (1.41); 7.4744 (1.51); 7.4626 (1.57); 7.4541 (2.78); 7.4424 (1.45); 7.3046 (1.74); 7.3001 (1.61); 6.5653 (3.6); 6.3551 (0.49); 6.2274 (0.51); 6.2183 (1.03); 6.2092 (0.51); 6.0815 (0.51); 4.4997 (0.95); 4.4906 (0.97); 4.4638 (2); 4.4547 (1.95); 4.4279 (1.01); 4.4188 (0.96); 3.9157 (16); 2.9656 (11.85); 2.713 (12.83); 2.2218 (0.35); 2.1662 (9.44); 2.1414 (54.94); 2.1195 (0.34); 2.1131 (0.38); 2.1069 (0.47); 1.9638 (2.05); 1.9576 (2.58); 1.9519 (21.59); 1.9457 (40.11); 1.9395 (55.62); 1.9333 (37.77); 1.9272 (19.18); 1.7679 (0.34); 1.3872 (3.11); 0.1459 (0.43); 0.008 (3.82); −0.0002 (102.16); −0.0086 (3.22); −0.1496 (0.44)

Compound No. C-39, solvent: [CD3CN],
8.7839 (0.35); 8.7805 (0.34); 8.7655 (0.34); 8.4511 (1.41); 8.4472 (1.38); 8.4393 (1.43); 8.4354 (1.35); 8.2876 (0.37); 8.2828 (0.37); 8.2537 (0.87); 8.1057 (0.42); 8.068 (3.82); 7.9717 (1.44); 7.9678 (1.34); 7.9515 (1.56); 7.9477 (1.43); 7.8447 (0.33); 7.5898 (1.51); 7.5855 (1.8); 7.5574 (1.72); 7.4738 (1.52); 7.462 (1.49); 7.4536 (1.41); 7.4418 (1.36); 7.3704 (0.45); 6.9743 (0.72); 6.9503 (0.44); 6.9322 (0.84); 6.914 (0.58); 6.5795 (2.29); 6.3612 (0.55); 6.2335 (0.58); 6.2244 (1.17); 6.2153 (0.57); 6.0876 (0.6); 4.515 (1.06); 4.5059 (1.08); 4.4791 (2.23); 4.4699 (2.16); 4.4431 (1.12); 4.434 (1.07); 4.1982 (0.41); 4.1801 (0.5); 4.1648 (0.42); 3.9699 (3.82); 3.9437 (0.48); 3.9322 (15.47); 3.8721 (0.35); 3.3878 (0.77); 3.3729 (0.71); 3.3635 (1.69); 3.3487 (1.6); 3.3384 (0.74); 3.3325 (1.58); 3.3194 (1.6); 3.3084 (0.94); 3.2988 (0.9); 3.2954 (0.77); 3.291 (0.61); 3.2856 (1.46); 3.2772 (16); 3.2678 (1.59); 3.2152 (0.47); 3.1927 (0.37); 2.7083 (2.06); 2.2218 (1.99); 2.2002 (12.4); 2.1767 (251.76); 2.1203 (0.5); 2.1142 (0.63); 2.108 (0.75); 2.1018 (0.53); 2.0647 (0.49); 2.046 (0.34); 1.9649 (3.33); 1.9588 (4.14); 1.953 (34.41); 1.9468 (64.4); 1.9407 (89.73); 1.9345 (61.17); 1.9283 (31.07); 1.9154 (0.49); 1.7752 (0.4); 1.7691 (0.55); 1.7628 (0.39); 1.3872 (12.01); 1.2698 (0.51); 1.2001 (0.56); 1.1921 (0.45); 1.1487 (6.42); 1.1317 (6.34); 1.1083 (0.66); 1.0927 (0.61); 0.146 (0.64); 0.008 (5.92); −0.0002 (160.8); −0.0086 (5.31); −0.1495 (0.67)

Compound No. C-40, solvent: [CD3CN],
8.8703 (0.43); 8.445 (0.81); 8.4411 (0.8); 8.4332 (0.82); 8.4293 (0.79); 8.0409 (2.28); 7.9665 (0.88); 7.9627 (0.79); 7.9464 (0.88); 7.9425 (0.81); 7.457 (1.15); 7.452 (0.97); 7.4455 (1.28); 7.437 (0.8); 7.4252 (0.76); 7.3025 (1.01); 7.2984 (0.92); 6.9739 (0.94); 6.5074 (1.92); 5.4463 (9.3); 5.1989 (0.59); 3.9339 (0.56); 3.9151 (11.68); 3.9132 (8.85); 3.8677 (0.4); 2.963 (6.83); 2.9517 (0.34); 2.7139 (7.24); 2.2218 (1.73); 2.1669 (5.26); 2.1335 (9.74); 1.9635 (1.26); 1.9574 (1.62); 1.9516 (12.85); 1.9454 (23.81); 1.9393 (32.94); 1.9331 (22.31); 1.9269 (11.25); 1.3873 (16); 1.2703 (0.78); 0.008 (2.49); −0.0002 (63.73); −0.0086 (1.96)

Compound No. C-41, solvent: [CD3CN],
8.444 (0.74); 8.4403 (0.81); 8.4323 (0.76); 8.4286 (0.78); 8.0623 (2.25); 7.9559 (0.78); 7.9521 (0.79); 7.9357 (0.85); 7.9319 (0.85); 7.582 (0.97); 7.5785 (1.14); 7.5461 (1.09); 7.455 (0.83); 7.4432 (0.83); 7.4348 (0.79); 7.423 (0.75); 6.973 (0.46); 6.5174 (1.43); 4.1773 (0.36); 3.9695 (0.48); 3.9433 (0.55); 3.9246 (16); 3.8709 (0.37); 3.3864 (0.61); 3.3715 (0.59); 3.3622 (1); 3.3474 (1); 3.3379 (0.42); 3.3286 (0.96); 3.3152 (1.12); 3.3047 (0.67); 3.2979 (0.51); 3.2936 (0.81); 3.2916 (0.81); 3.2854 (1.24); 3.2765 (8.36); 3.2666 (1.46); 3.1931 (0.38); 2.2217 (0.92); 2.1941 (6.07); 2.1659 (0.98); 2.1485 (1.64); 2.1131 (0.43); 2.1066 (0.39); 1.9712 (0.4); 1.9635 (0.91); 1.9516 (8.79); 1.9454 (16.31); 1.9393 (22.5); 1.9331

| 1H NMR data[b)] |
| --- |

(15.33); 1.9269 (7.85); 1.3871 (6.51); 1.2692 (0.56); 1.2001 (0.42); 1.147 (3.56); 1.1381 (0.5); 1.13 (3.51); 1.1065 (0.63); 1.0912 (0.55); 0.008 (1.59); −0.0002 (39.16); −0.0085 (1.6)
Compound No. C-42, solvent: [CD3CN],
8.783 (0.47); 8.7796 (0.44); 8.7645 (0.44); 8.7611 (0.42); 8.4842 (0.66); 8.4804 (0.68); 8.4724 (0.68); 8.4686 (0.67); 8.2857 (0.43); 8.2808 (0.47); 8.2524 (1.1); 8.1056 (0.41); 8.1037 (0.41); 8.0503 (1.76); 8.0013 (0.72); 7.9975 (0.69); 7.9811 (0.73); 7.9772 (0.69); 7.8622 (0.39); 7.8587 (0.41); 7.8443 (0.41); 7.8408 (0.41); 7.5751 (0.65); 7.5707 (0.92); 7.5533 (0.83); 7.5191 (0.71); 7.5073 (0.71); 7.4989 (0.71); 7.4871 (0.65); 7.2118 (0.72); 6.9501 (0.38); 6.9319 (0.69); 6.9137 (0.37); 5.5629 (1.85); 5.4429 (1.85); 4.0404 (0.41); 3.9699 (5); 3.9372 (0.53); 3.9274 (0.72); 3.9206 (7.58); 3.8853 (0.47); 3.8751 (0.65); 3.8701 (0.61); 3.8592 (0.59); 3.8548 (0.48); 3.8439 (0.45); 2.7714 (0.47); 2.762 (0.46); 2.7532 (0.34); 2.7073 (2.55); 2.5476 (0.8); 2.5374 (0.69); 2.2771 (0.43); 2.2011 (8.2); 2.1795 (223.58); 2.1206 (0.34); 2.1143 (0.46); 2.1082 (0.56); 2.102 (0.42); 1.9651 (4.2); 1.959 (5.45); 1.9531 (34.07); 1.9469 (62.09); 1.9408 (84.55); 1.9346 (58.11); 1.9284 (29.89); 1.7753 (0.35); 1.7692 (0.48); 1.763 (0.33); 1.3872 (0.43); 1.2697 (0.67); 1.1003 (16); 1.085 (15.69); 0.7333 (0.71); 0.7282 (0.95); 0.7155 (0.97); 0.7103 (0.72); 0.6979 (0.34); 0.5498 (0.34); 0.5382 (0.78); 0.5327 (0.81); 0.5282 (0.73); 0.5231 (0.73); 0.146 (0.44); 0.02 (0.33); 0.008 (3.93); −0.0002 (113.53); −0.0086 (4.44); −0.1496 (0.44)
Compound No. C-43, solvent: [CD3CN],
9.8852 (0.52); 8.4751 (1.37); 8.4713 (1.4); 8.4633 (1.4); 8.4595 (1.41); 8.2543 (0.44); 8.1105 (0.34); 8.0754 (4.06); 7.9957 (1.4); 7.9918 (1.4); 7.9755 (1.54); 7.9716 (1.48); 7.6044 (1.56); 7.5998 (1.83); 7.5563 (1.66); 7.5153 (1.58); 7.5035 (1.55); 7.4951 (1.47); 7.4833 (1.51); 7.1942 (1.57); 7.0592 (0.41); 7.0422 (0.42); 5.547 (3.96); 5.427 (3.97); 4.0403 (0.45); 3.9699 (1.91); 3.946 (0.91); 3.9301 (16); 3.8691 (0.8); 3.4565 (0.36); 3.4359 (0.69); 3.4192 (0.71); 3.3984 (0.38); 2.7088 (1.01); 2.2805 (0.55); 2.2008 (15.57); 2.183 (201.82); 2.1205 (0.37); 2.1143 (0.5); 2.108 (0.58); 2.1019 (0.42); 1.965 (3.78); 1.9589 (4.91); 1.9531 (30.51); 1.9469 (56.1); 1.9407 (76.54); 1.9345 (52.45); 1.9283 (26.95); 1.7691 (0.45); 1.3871 (0.36); 1.2694 (0.52); 1.2112 (6.3); 1.1945 (6.21); 1.1796 (0.37); 1.1628 (0.32); 1.1002 (3.2); 1.0946 (0.33); 1.0849 (3.1); 0.9253 (0.39); 0.9129 (0.72); 0.9043 (0.46); 0.901 (0.48); 0.8924 (0.78); 0.8803 (0.51); 0.8718 (0.34); 0.4825 (0.34); 0.4738 (0.8); 0.4644 (0.6); 0.4604 (0.59); 0.4529 (0.7); 0.4436 (0.41); 0.4396 (0.44); 0.43 (0.43); 0.3876 (0.41); 0.3774 (0.49); 0.3743 (0.49); 0.3675 (0.43); 0.3642 (0.68); 0.3546 (0.65); 0.3438 (0.74); 0.2899 (0.5); 0.2797 (0.7); 0.267 (0.96); 0.2571 (0.94); 0.2478 (0.71); 0.245 (0.64); 0.2393 (0.63); 0.2356 (0.98); 0.2264 (0.81); 0.2134 (0.63); 0.2036 (0.38); 0.1457 (0.44); 0.0206 (0.33); 0.0192 (0.37); 0.017 (0.47); 0.0162 (0.49); 0.0155 (0.5); 0.0147 (0.55); 0.014 (0.6); 0.0132 (0.64); 0.0125 (0.69); 0.0118 (0.76); 0.0081 (3.74); 0.0061 (2.33); −0.0002 (96.84); −0.0069 (2.4); −0.0086 (3.81); −0.1497 (0.39)
Compound No. C-44, solvent: [CD3CN],
8.4773 (0.48); 8.4734 (0.51); 8.4655 (0.51); 8.4617 (0.5); 8.0612 (1.51); 7.9971 (0.47); 7.9933 (0.47); 7.9769 (0.53); 7.9732 (0.52); 7.5517 (0.79); 7.5348 (0.71); 7.5161 (0.54); 7.5043 (0.53); 7.4959 (0.49); 7.4841 (0.48); 7.1954 (0.65); 5.5511 (1.48); 5.4312 (1.48); 3.9696 (1.43); 3.9253 (5.73); 3.5999 (9.67); 2.7082 (0.74); 2.1944 (3.8); 2.1405 (20.68); 1.9638 (1.77); 1.9577 (2.44); 1.9518 (14.16); 1.9457 (25.67); 1.9395 (34.85); 1.9333 (24.07); 1.9272 (12.54); 1.3475 (16); 1.2585 (0.32); 0.008 (1.83); −0.0002 (44.06); −0.0085 (1.93)
Compound No. C-45, solvent: [CD3CN],
10.0319 (0.78); 8.4814 (1.37); 8.4778 (1.44); 8.4697 (1.42); 8.4659 (1.42); 8.3721 (0.65); 8.3684 (0.7); 8.3603 (0.69); 8.3567 (0.69); 8.2547 (0.49); 8.1542 (2.01); 8.1063 (1.01); 8.0625 (4.27); 8.0002 (1.38); 7.9962 (1.6); 7.9841 (0.84); 7.98 (2.18); 7.9761 (1.58); 7.9639 (0.82); 7.9601 (0.8); 7.8026 (0.82); 7.6194 (1.77); 7.6152 (2.04); 7.555 (1.85); 7.5182 (1.5); 7.5065 (1.42); 7.4981 (1.42); 7.4863 (1.48); 7.4426 (0.74); 7.4309 (0.71); 7.4223 (0.69); 7.4107 (0.66); 7.1963 (1.73); 7.1275 (1.18); 7.124 (1.19); 7.0256 (0.47); 6.9321 (0.35); 5.59 (2.34); 5.5564 (4.35); 5.4699 (2.35); 5.4364 (4.35); 4.0401 (0.62); 3.9922 (0.6); 3.977 (0.45); 3.9697 (2.11); 3.9395 (1.37); 3.9333 (7.93); 3.9234 (16); 3.8736 (1.01); 3.7116 (7.58); 2.8189 (7.39); 2.8069 (7.44); 2.7925 (0.53); 2.7803 (0.46); 2.7099 (1.24); 2.7038 (0.49); 2.2835 (0.71); 2.2017 (10.96); 2.1701 (1.7); 2.1408 (241.93); 2.1194 (1.32); 2.1132 (1.53); 2.107 (2); 2.1009 (1.28); 2.0947 (0.68); 1.9859 (5.3); 1.9638 (13.37); 1.9577 (18.31); 1.9519 (106.67); 1.9458 (194.08); 1.9396 (265.94); 1.9334 (183.23); 1.9272 (94.77); 1.7802 (0.57); 1.7742 (1.07); 1.768 (1.55); 1.7619 (1.04); 1.7557 (0.52); 1.3871 (0.71); 1.2851 (0.52); 1.2699 (2.5); 1.0998 (2.05); 1.0845 (2.03); 0.8816 (0.35); 0.1458 (1.43); 0.0077 (13.09); −0.0002 (311.34); −0.0084 (14.78); −0.0198 (0.78); −0.0221 (0.54); −0.0228 (0.51); −0.0236 (0.49); −0.0251 (0.4); −0.1498 (1.43)
Compound No. C-46, solvent: [CD3CN],
9.8941 (0.78); 8.5577 (0.66); 8.5538 (0.68); 8.5459 (0.69); 8.542 (0.67); 8.4498 (1.44); 8.4459 (1.48); 8.438 (1.52); 8.4341 (1.47); 8.1312 (1.95); 8.101 (0.7); 8.0972 (0.71); 8.0808 (0.8); 8.0769 (0.82); 8.0702 (0.9); 8.0656 (1.05); 8.0598 (4.29); 7.9688 (1.48); 7.9649 (1.45); 7.9486 (1.6); 7.9448 (1.53); 7.8656 (0.77); 7.6057 (1.69); 7.6012 (1.94); 7.5858 (0.74); 7.5773 (0.7); 7.5655 (0.7); 7.5443 (1.75); 7.472 (1.58); 7.4602 (1.55); 7.4519 (1.48); 7.4401 (1.41); 7.0718 (0.48); 6.7828 (2.46); 6.5728 (2.56); 6.3721 (0.4); 6.3631 (0.75); 6.3542 (0.37); 6.2352 (0.77); 6.2262 (1.51); 6.2171 (0.74); 6.0983 (0.36); 6.0893 (0.76); 6.0804 (0.36); 4.5319 (0.58); 4.5228 (0.63); 4.5153 (1.18); 4.5062 (1.21); 4.4959 (1.24); 4.4869 (1.28); 4.4794 (2.44); 4.4703 (2.37); 4.46 (0.69); 4.4509 (0.64); 4.4435 (1.24); 4.4344 (1.14); 3.9992 (0.38); 3.9741 (1.02); 3.9705 (0.4); 3.9413 (7.59); 3.9238 (16); 3.8894 (0.33); 3.6007 (1.45); 3.3509 (0.56); 3.3361 (0.76); 3.3327 (1.83); 3.3184 (1.93); 3.3146 (1.97); 3.3003 (1.84); 3.2966 (0.77); 3.2822 (0.59); 2.2462 (0.37); 2.1931 (14.94); 2.1778 (138.64); 2.1759 (139.14); 2.1203 (0.34); 2.1142 (0.41); 2.108 (0.45); 2.102 (0.33); 1.9648 (2.48); 1.9588 (3.35); 1.9529 (20.86); 1.9468 (38.1); 1.9406 (51.87); 1.9344 (35.78); 1.9282 (18.56); 1.7848 (4.63); 1.7755 (0.42); 1.769 (0.37); 1.2692 (0.34); 1.1486 (3.82); 1.1305 (7.75); 1.1124 (3.7); 0.008 (2.27); −0.0002 (60.99); −0.0085 (2.62)
Compound No. C-47, solvent: [CD3CN],
9.8738 (0.71); 8.5509 (0.62); 8.547 (0.65); 8.5391 (0.64); 8.5353 (0.67); 8.4445 (1.2); 8.4407 (1.27); 8.4328 (1.26); 8.4289 (1.29); 8.1294 (2.09); 8.0886 (0.63); 8.0849 (0.67); 8.0604 (4.79); 7.9556 (1.26); 7.9517 (1.27); 7.9354 (1.4); 7.9316 (1.39); 7.8595 (0.85); 7.6072 (1.58); 7.6033 (1.81); 7.5816 (0.7); 7.5698 (0.74); 7.5614 (0.79); 7.5461 (1.75); 7.4557 (1.32); 7.4439 (1.34); 7.4356 (1.31); 7.4238 (1.21); 7.0584 (0.44); 6.7153 (2.32); 6.5053 (2.4); 4.0342 (0.38); 3.982 (0.34); 3.9702 (1.35); 3.9456 (8.06); 3.9399 (8.24); 3.9265 (15.3); 3.9231 (16); 3.8891 (1.46); 3.8723 (0.38); 3.5999 (9.08); 3.3509 (0.5);

| 1H NMR data[b] |
|---|
| 3.3329 (1.61); 3.3186 (1.73); 3.3148 (1.78); 3.3005 (1.66); 3.2824 (0.57); 2.5671 (0.91); 2.2474 (0.91); 2.1945 (9.34); 2.1469 (96.83); 2.1195 (0.88); 2.1132 (0.96); 2.107 (0.95); 2.1008 (0.65); 2.0947 (0.43); 1.9638 (4.65); 1.9577 (6.4); 1.9519 (39.79); 1.9458 (72.74); 1.9396 (98.98); 1.9334 (68.17); 1.9272 (35.24); 1.7865 (4.8); 1.7742 (0.59); 1.768 (0.72); 1.7619 (0.52); 1.3871 (0.74); 1.2698 (1.06); 1.1489 (3.39); 1.1308 (6.8); 1.1127 (3.34); 0.1458 (0.49); 0.0079 (4.39); −0.0003 (111.28); −0.0086 (4.13); −0.1496 (0.51) |
| Compound No. C-48, solvent: [CD3CN], 8.4449 (0.82); 8.441 (0.84); 8.4331 (0.87); 8.4292 (0.85); 8.0573 (2.29); 7.9522 (0.85); 7.9483 (0.86); 7.9321 (0.98); 7.9282 (0.96); 7.5989 (0.87); 7.5945 (1.07); 7.5568 (0.98); 7.5535 (0.86); 7.4496 (0.94); 7.4378 (0.93); 7.4295 (0.9); 7.4177 (0.87); 6.5185 (1.26); 4.0726 (1); 4.0664 (1.16); 4.059 (1.09); 4.0526 (0.98); 3.9881 (0.56); 3.9447 (0.47); 3.9423 (0.35); 3.9403 (0.36); 3.9358 (0.99); 3.926 (16); 3.5989 (13.45); 2.4702 (0.76); 2.4639 (1.48); 2.4575 (0.74); 2.22 (0.51); 2.1951 (5.56); 2.1586 (3.12); 1.9749 (0.34); 1.9716 (0.35); 1.9636 (0.49); 1.9575 (0.64); 1.9517 (3.72); 1.9455 (6.75); 1.9393 (9.16); 1.9331 (6.3); 1.9269 (3.23); 0.008 (0.53); −0.0002 (12.54); −0.0086 (0.47) |
| Compound No. C-49, solvent: [CD3CN], 9.9178 (0.65); 8.7815 (0.76); 8.7781 (0.74); 8.763 (0.72); 8.7596 (0.72); 8.4772 (1.3); 8.4733 (1.38); 8.4654 (1.36); 8.4616 (1.36); 8.2835 (0.74); 8.2785 (0.76); 8.2507 (1.86); 8.1008 (1); 8.0652 (3.93); 7.9947 (1.41); 7.9908 (1.42); 7.9861 (0.46); 7.9745 (1.47); 7.9706 (1.46); 7.8604 (0.67); 7.8568 (0.72); 7.8424 (0.7); 7.839 (0.68); 7.599 (1.5); 7.5945 (1.79); 7.5519 (1.64); 7.5149 (1.48); 7.5032 (1.49); 7.4947 (1.41); 7.483 (1.51); 7.1953 (1.52); 6.9482 (0.71); 6.9301 (1.37); 6.912 (0.96); 6.9007 (0.46); 5.5529 (3.85); 5.4329 (3.84); 4.1059 (0.48); 4.0897 (0.7); 4.087 (0.59); 4.0703 (0.72); 4.0536 (0.55); 4.0401 (0.94); 3.9697 (8.12); 3.9428 (1.6); 3.9328 (1.14); 3.9266 (16); 3.8721 (1.4); 2.706 (4.22); 2.2793 (0.87); 2.2002 (10.12); 2.159 (167.72); 2.1198 (0.61); 2.1137 (0.78); 2.1075 (0.94); 2.1012 (0.69); 2.0952 (0.38); 2.0592 (0.4); 1.9644 (6); 1.9583 (7.94); 1.9524 (46.89); 1.9463 (84.83); 1.9401 (114.52); 1.9339 (78.93); 1.9277 (40.44); 1.7747 (0.5); 1.7685 (0.68); 1.7623 (0.45); 1.6772 (0.44); 1.6603 (0.49); 1.3871 (0.84); 1.2688 (1.71); 1.215 (1.05); 1.1991 (1.07); 1.1622 (13.42); 1.1457 (13.28); 1.1308 (1.38); 1.1143 (1.31); 1.0633 (0.55); 1.047 (0.47); 0.1458 (0.51); 0.025 (0.32); 0.0081 (5.57); −0.0002 (131.86); −0.0085 (4.59); −0.1497 (0.51) |
| Compound No. C-50, solvent: [CD3CN], 9.6886 (0.84); 8.4885 (0.74); 8.4764 (0.74); 8.4347 (1.19); 8.4308 (1.24); 8.4229 (1.24); 8.419 (1.24); 8.1303 (0.43); 8.1132 (0.33); 8.1107 (0.53); 8.1083 (0.33); 8.0832 (3.84); 7.9537 (1.23); 7.9498 (1.25); 7.9467 (0.61); 7.9423 (0.54); 7.9336 (1.35); 7.9297 (1.31); 7.7293 (0.52); 7.7249 (0.43); 7.71 (0.33); 7.6991 (1.99); 7.6963 (1.87); 7.6839 (1.2); 7.6794 (1.26); 7.6646 (1.04); 7.6602 (1.1); 7.5856 (1.6); 7.5826 (1.53); 7.4582 (1.39); 7.4464 (1.34); 7.438 (1.28); 7.4262 (1.23); 7.3552 (0.42); 7.3353 (0.39); 7.3196 (1.13); 7.3 (1.01); 7.2291 (0.62); 7.215 (0.6); 7.2101 (0.56); 7.1978 (0.52); 6.4642 (2.38); 6.3522 (0.53); 6.2245 (0.51); 6.2154 (1.07); 6.2063 (0.53); 6.0785 (0.54); 5.4463 (16); 4.7043 (1.25); 4.6898 (1.23); 4.5949 (2.96); 4.5805 (2.93); 4.4924 (0.97); 4.4833 (0.99); 4.4566 (2.02); 4.4474 (1.99); 4.2207 (1.05); 4.4115 (0.99); 3.9276 (14.33); 2.2161 (8.92); 2.1342 (22.41); 2.1066 (0.36); 1.9712 (0.65); 1.9635 (3.08); 1.9574 (5); 1.9515 (22.55); 1.9453 (39.49); 1.9392 (51.74); 1.933 (35.48); 1.9268 (18.17); 0.0078 (1.33); −0.0002 (38.15); −0.0086 (1.13) |
| Compound No. C-51, solvent: [CD3CN], 9.674 (0.77); 8.4929 (0.77); 8.4807 (0.78); 8.4296 (1.3); 8.4257 (1.33); 8.4178 (1.35); 8.4139 (1.32); 8.0846 (4.03); 7.942 (1.36); 7.9381 (1.33); 7.9219 (1.49); 7.918 (1.41); 7.7008 (2); 7.698 (1.85); 7.6857 (1.22); 7.6812 (1.24); 7.6665 (1.02); 7.662 (1.11); 7.5887 (1.67); 7.5852 (1.52); 7.4436 (1.51); 7.4318 (1.46); 7.4234 (1.39); 7.4117 (1.36); 7.3185 (1.18); 7.2989 (1.20); 7.2321 (0.67); 7.2187 (0.63); 7.2133 (0.59); 7.1995 (0.53); 6.4181 (2.4); 5.4464 (1.77); 4.5963 (3.08); 4.5819 (3.04); 4.43 (0.74); 3.9272 (16); 3.9038 (15.47); 2.218 (9.47); 2.1324 (46.64); 2.1191 (0.62); 2.1129 (0.73); 2.1066 (0.91); 2.1005 (0.65); 2.0943 (0.33); 1.9635 (8.02); 1.9575 (12.3); 1.9516 (58.43); 1.9454 (103.85); 1.9393 (137.89); 1.9331 (95.14); 1.9269 (48.68); 1.9139 (0.56); 1.78 (0.32); 1.7739 (0.59); 1.7677 (0.8); 1.7616 (0.54); 1.3873 (0.4); 1.2697 (0.36); 0.146 (0.36); 0.0081 (3.01); −0.0002 (92.02); −0.0086 (2.68); −0.1494 (0.38) |
| Compound No. C-52, solvent: [CD3CN], 9.6592 (0.77); 8.4556 (1.36); 8.4517 (1.36); 8.4438 (1.41); 8.4399 (1.37); 8.072 (3.99); 7.9706 (1.36); 7.9667 (1.32); 7.9504 (1.5); 7.9465 (1.42); 7.6174 (1.48); 7.613 (1.8); 7.58 (1.64); 7.4719 (1.53); 7.4601 (1.49); 7.4517 (1.41); 7.44 (1.39); 7.3774 (0.44); 6.5855 (2.12); 6.3632 (0.57); 6.2354 (0.57); 6.2263 (1.15); 6.2171 (0.56); 6.0894 (0.59); 4.5164 (1.02); 4.5073 (1.04); 4.4805 (2.19); 4.4714 (2.11); 4.4446 (1.1); 4.4355 (1.05); 4.0782 (2.43); 4.0718 (2.49); 4.0644 (2.46); 4.0577 (2.37); 3.9286 (16); 2.4679 (1.34); 2.4617 (2.34); 2.4552 (1.1); 2.2087 (9.11); 2.1499 (96.06); 2.126 (0.4); 2.1195 (0.6); 2.1133 (0.83); 2.1071 (0.99); 2.101 (0.7); 2.0948 (0.37); 1.964 (8.83); 1.958 (14.13); 1.9521 (66.59); 1.9459 (117.63); 1.9397 (154.99); 1.9335 (106.75); 1.9274 (54.62); 1.9146 (0.78); 1.7805 (0.38); 1.7743 (0.65); 1.7682 (0.9); 1.7621 (0.61); 0.1459 (0.43); 0.008 (3.78); −0.0002 (113.57); −0.0086 (3.31); −0.1496 (0.45) |
| Compound No. C-53, solvent: [CD3CN], 9.9788 (0.45); 8.4776 (1.34); 8.4738 (1.38); 8.4659 (1.42); 8.462 (1.39); 8.0632 (3.77); 7.997 (1.41); 7.9931 (1.41); 7.9768 (1.57); 7.9729 (1.51); 7.6111 (1.38); 7.6065 (1.57); 7.5497 (1.4); 7.5454 (1.25); 7.5161 (1.64); 7.5043 (1.59); 7.4959 (1.52); 7.4841 (1.49); 7.1991 (1.32); 7.0883 (0.33); 5.5529 (3.84); 5.4329 (3.84); 3.9757 (0.38); 3.9698 (0.93); 3.9326 (0.51); 3.9255 (16); 3.6011 (2.81); 3.3451 (0.51); 3.3308 (0.61); 3.327 (1.64); 3.3127 (1.7); 3.3089 (1.74); 3.2946 (1.66); 3.2908 (0.65); 3.2765 (0.54); 2.7083 (0.4); 2.1925 (71.91); 2.1084 (0.36); 1.9654 (2.42); 1.9593 (3.49); 1.9534 (17.67); 1.9472 (31.34); 1.9411 (41.82); 1.9349 (29.02); 1.9287 (14.97); 1.9221 (0.49); 1.2694 (0.39); 1.14 (3.4); 1.1219 (6.98); 1.1038 (3.31); 0.008 (0.54); −0.0002 (17.42); −0.0086 (0.5) |
| Compound No. C-54, solvent: [CD3CN], 8.4767 (1.23); 8.4729 (1.26); 8.4649 (1.3); 8.4611 (1.27); 8.0715 (3.58); 8.0005 (1.21); 7.9967 (1.2); 7.9803 (1.37); 7.9765 (1.28); 7.5903 (1.31); 7.5857 (1.71); 7.5605 (1.55); 7.5179 (1.37); 7.5061 (1.35); 7.4977 (1.27); 7.4859 (1.27); 7.2177 (1.37); 6.9983 (0.36); 6.9787 (0.37); 5.5535 (3.5); 5.4336 (3.51); 4.1857 (0.35); 4.1689 (0.44); 4.1519 (0.36); 3.9703 (0.55); 3.9275 (14.76); 3.6024 (2.29); 3.3763 (0.72); 3.3614 (0.71); 3.3521 (1.59); 3.3373 (1.55); 3.3175 (1.51); 3.3044 (1.53); 3.2934 (0.82); 3.2878 |

| 1H NMR data[b] |
| --- |

(0.62); 3.2802 (0.7); 3.2659 (0.87); 3.2601 (16); 3.2529 (0.52); 2.2618 (178.58); 2.2048 (9.18); 2.1681 (0.37); 2.1102 (0.37); 1.9671 (2.64); 1.9611 (4.01); 1.9552 (19.66); 1.949 (35); 1.9428 (46.33); 1.9366 (31.89); 1.9304 (16.39); 1.9176 (0.37); 1.3868 (0.38); 1.269 (0.42); 1.1346 (6.28); 1.1176 (6.24); 0.008 (0.71); −0.0002 (19.89); −0.0086 (0.55)

Compound No. C-55, solvent: [CD3CN],
8.4789 (0.92); 8.4751 (0.93); 8.4672 (0.95); 8.4633 (0.95); 8.0485 (2.7); 8.007 (0.88); 8.0032 (0.87); 7.9868 (0.99); 7.983 (0.97); 7.5162 (1.03); 7.5044 (1.01); 7.496 (1.01); 7.4841 (1.89); 7.3154 (1.18); 7.3114 (1.15); 7.1863 (1.33); 7.1835 (1.23); 5.5371 (2.35); 5.417 (2.35); 3.9334 (0.47); 3.9162 (11.29); 3.6004 (16); 2.9543 (8.25); 2.7188 (8.06); 2.3471 (0.35); 2.1942 (6.7); 2.1564 (57.29); 2.1199 (0.64); 2.1136 (0.6); 2.1074 (0.64); 2.1013 (0.5); 2.095 (0.35); 1.9643 (4.18); 1.9582 (6.23); 1.9523 (30.45); 1.9462 (54.16); 1.94 (71.91); 1.9338 (49.65); 1.9276 (25.58); 1.9147 (0.48); 1.7745 (0.32); 1.7684 (0.43); 1.3873 (0.48); 1.2697 (1.06); 0.008 (0.85); −0.0002 (26.33); −0.0086 (0.83)

Compound No. C-56, solvent: [CD3CN],
9.8301 (0.71); 8.4803 (1.17); 8.4765 (1.2); 8.4685 (1.21); 8.4647 (1.18); 8.0714 (3.8); 7.9995 (1.12); 7.9957 (1.11); 7.9793 (1.25); 7.9755 (1.18); 7.6141 (1.52); 7.6096 (1.77); 7.5677 (1.62); 7.5169 (1.31); 7.5051 (1.26); 7.4966 (1.19); 7.4849 (1.14); 7.2009 (1.44); 7.0971 (0.41); 5.5549 (3.74); 5.4349 (3.75); 3.9269 (14.77); 3.4494 (4.57); 3.4428 (8.8); 3.2618 (16); 2.4635 (0.32); 2.2084 (9.27); 2.1523 (100.39); 2.1196 (0.64); 2.1134 (0.82); 2.1072 (0.94); 2.101 (0.66); 2.0948 (0.35); 1.9641 (8.3); 1.958 (12.32); 1.9521 (60.98); 1.946 (108.04); 1.9398 (142.71); 1.9336 (97.79); 1.9275 (50.11); 1.9148 (0.66); 1.7805 (0.35); 1.7743 (0.61); 1.7683 (0.84); 1.7621 (0.57); 1.3716 (0.45); 1.2765 (0.59); 1.2708 (0.36); 0.0079 (1.56); −0.0003 (48.22); −0.0087 (1.36)

Compound No. C-57, solvent: [CD3CN],
9.7204 (0.35); 8.4825 (1.32); 8.4787 (1.34); 8.4707 (1.38); 8.4669 (1.36); 8.2524 (0.38); 8.0705 (4.09); 7.9962 (1.32); 7.9923 (1.39); 7.976 (1.51); 7.9722 (1.38); 7.6184 (1.61); 7.6139 (1.97); 7.5791 (1.77); 7.5144 (1.45); 7.5027 (1.43); 7.4942 (1.4); 7.4824 (1.32); 7.3472 (0.41); 7.2056 (1.54); 5.5545 (4.06); 5.4345 (4.07); 4.0709 (1.94); 4.0646 (2.11); 4.0571 (2.08); 4.0508 (1.95); 3.9695 (1.66); 3.9459 (0.62); 3.9382 (1.15); 3.9292 (16); 3.8739 (0.49); 3.5998 (2.19); 2.7078 (0.89); 2.4544 (1.12); 2.4482 (2.09); 2.4418 (1); 2.2348 (0.41); 2.2099 (9.89); 2.1679 (0.43); 2.1394 (23.48); 2.1196 (0.35); 2.1131 (0.35); 2.1069 (0.41); 1.9638 (3.48); 1.9577 (4.74); 1.9518 (22.67); 1.9457 (40.07); 1.9395 (52.91); 1.9333 (36.24); 1.9271 (18.51); 1.9205 (0.62); 1.3872 (0.63); 0.9745 (0.57); 0.8875 (0.58); 0.008 (0.72); −0.0002 (21.14); −0.0085 (0.62)

Compound No. C-58, solvent: [CD3CN],
9.725 (0.78); 9.7008 (0.36); 8.5338 (1.2); 8.495 (1.62); 8.4912 (1.64); 8.4832 (1.62); 8.4794 (1.53); 8.4411 (0.82); 8.432 (0.81); 8.1032 (0.59); 8.0686 (3.99); 8.0078 (1.45); 8.004 (1.38); 7.9876 (1.67); 7.9837 (1.49); 7.9616 (0.48); 7.6723 (1.1); 7.6678 (0.75); 7.6581 (0.83); 7.6524 (1.08); 7.647 (2.05); 7.6422 (1.97); 7.6334 (0.41); 7.5824 (1.75); 7.5379 (1.97); 7.5261 (1.81); 7.5176 (1.59); 7.5058 (1.45); 7.2552 (0.77); 7.2429 (0.8); 7.2357 (0.79); 7.2224 (0.99); 7.216 (1.91); 7.074 (0.94); 6.9377 (2.04); 6.8014 (1.01); 4.4884 (2.93); 4.4733 (2.99); 4.4512 (0.41); 3.9713 (0.92); 3.9404 (1.23); 3.937 (2.72); 3.9205 (16); 3.8696 (1.86); 2.2946 (0.62); 2.2835 (1.25); 2.2088 (10.16); 2.1726 (1.5); 2.1464 (49.79); 2.1195 (0.52); 2.1132 (0.67); 2.107 (0.8); 2.1009 (0.53); 1.9639 (6.71); 1.9579 (10.03); 1.952 (48.66); 1.9458 (86.02); 1.9396 (113.39); 1.9335 (78.16); 1.9273 (40.03); 1.9144 (0.59); 1.7742 (0.48); 1.7681 (0.67); 1.7619 (0.45); 1.3716 (0.43); 1.3403 (0.92); 1.2851 (1.13); 1.2765 (0.57); 1.2703 (0.47); 1.0996 (0.89); 1.0843 (0.9); 0.008 (1.4); −0.0002 (43.31); −0.0086 (1.28)

Compound No. C-59, solvent: [CD3CN],
8.7602 (1.39); 8.7567 (1.39); 8.7417 (1.43); 8.7383 (1.26); 8.2448 (1.61); 8.24 (1.62); 8.2276 (3.83); 8.1437 (0.58); 8.0711 (1.5); 8.0689 (1.43); 7.8449 (1.32); 7.8415 (1.26); 7.8271 (1.38); 7.8236 (1.24); 7.4192 (0.42); 6.9782 (0.34); 6.9363 (1.2); 6.9181 (2.16); 6.8999 (1.11); 4.4468 (0.55); 4.0393 (0.55); 3.9693 (16); 3.9608 (0.91); 3.9567 (0.49); 3.9417 (0.37); 3.9337 (2.42); 3.7802 (0.52); 3.7663 (0.76); 3.6682 (0.37); 3.5999 (1.32); 3.322 (2.05); 3.3051 (2.48); 2.701 (1.09); 2.6857 (8.66); 2.667 (0.33); 2.1488 (29.49); 2.1076 (0.34); 2.0443 (1.33); 1.9644 (2.78); 1.9584 (4.25); 1.9525 (19.87); 1.9463 (35.16); 1.9402 (46.34); 1.934 (31.78); 1.9278 (16.2); 1.3871 (0.51); 0.008 (0.6); −0.0002 (17.34); −0.0086 (0.54)

Compound No. C-60, solvent: [CD3CN],
9.8159 (0.34); 8.4912 (1.27); 8.4874 (1.28); 8.4794 (1.32); 8.4756 (1.29); 8.253 (0.49); 8.1049 (0.35); 8.0705 (3.74); 8.0162 (1.25); 8.0124 (1.23); 7.996 (1.37); 7.9921 (1.34); 7.5958 (1.42); 7.5915 (1.76); 7.562 (1.62); 7.5423 (1.48); 7.5305 (1.4); 7.5221 (1.29); 7.5103 (1.26); 7.3186 (1.69); 7.0775 (0.87); 6.9493 (0.33); 6.9412 (2.03); 6.931 (0.73); 6.9128 (0.56); 6.8049 (0.91); 4.19 (0.36); 4.1712 (0.47); 4.1545 (0.4); 3.9696 (2.18); 3.961 (0.71); 3.957 (0.34); 3.9436 (0.79); 3.9282 (14.93); 3.8718 (0.59); 3.6003 (1.3); 3.376 (0.72); 3.3612 (0.72); 3.3518 (1.67); 3.3371 (1.66); 3.3198 (1.63); 3.3067 (1.67); 3.2956 (0.78); 3.2826 (0.82); 3.2655 (1.11); 3.2594 (16); 3.253 (0.58); 3.1924 (0.65); 2.708 (1.11); 2.2793 (0.36); 2.2047 (9.18); 2.1645 (77.08); 2.12 (0.41); 2.1137 (0.51); 2.1076 (0.58); 2.1014 (0.49); 1.9645 (4.25); 1.9584 (6.37); 1.9525 (31.49); 1.9464 (56.09); 1.9402 (74.42); 1.934 (51.38); 1.9278 (26.48); 1.9148 (0.55); 1.7747 (0.36); 1.7687 (0.48); 1.7625 (0.34); 1.3872 (0.54); 1.3403 (0.33); 1.285 (0.41); 1.2694 (0.35); 1.1374 (6.44); 1.1205 (6.38); 1.1086 (0.4); 1.0916 (0.33); 0.008 (1.11); −0.0002 (32.41); −0.0086 (0.97)

Compound No. C-61, solvent: [CD3CN],
8.8536 (0.48); 8.4939 (1.24); 8.4901 (1.29); 8.4821 (1.3); 8.4783 (1.31); 8.0534 (3.67); 8.0435 (0.46); 8.0271 (1.24); 8.0232 (1.18); 8.0068 (1.38); 8.003 (1.39); 7.5445 (1.39); 7.5327 (1.4); 7.5242 (1.36); 7.5124 (2.59); 7.3244 (1.73); 7.3202 (1.53); 7.2833 (2.04); 7.0665 (0.74); 6.9301 (1.61); 6.7939 (0.8); 3.9331 (0.42); 3.9277 (0.82); 3.9158 (16); 3.2628 (0.63); 2.9495 (11); 2.7224 (11.36); 2.4636 (0.35); 2.3564 (1.11); 2.2109 (8.52); 2.1476 (313.07); 2.1196 (1.9); 2.1134 (2.38); 2.1072 (2.49); 2.1011 (1.71); 2.0949 (0.93); 2.0158 (1.11); 1.9641 (19.61); 1.9581 (29.77); 1.9522 (144.72); 1.946 (257.34); 1.9398 (340.73); 1.9336 (234.21); 1.9275 (120.24); 1.9147 (2.19); 1.7805 (0.91); 1.7744 (1.54); 1.7683 (2.04); 1.7621 (1.38); 1.7559 (0.78); 1.3716 (2.08); 1.2853 (0.52); 1.2766 (2.5); 1.2703 (0.81); 1.2037 (0.38); 1.1996 (0.42); 1.1805 (0.45); 1.1242 (0.32); 0.1459 (0.48); 0.008 (3.99); −0.0002 (123.46); −0.0086 (3.81); −0.1497 (0.52)

-continued

1H NMR data[b]

Compound No. C-62, solvent: [CD3CN],
9.711 (0.71); 8.497 (1.31); 8.4932 (1.33); 8.4852 (1.35); 8.4814 (1.32); 8.0734 (4.12); 8.0153 (1.3); 8.0115 (1.25); 7.9951 (1.43); 7.9912 (1.35); 7.621 (1.57); 7.6166 (1.91); 7.585 (1.78); 7.5416 (1.49); 7.5299 (1.44); 7.5214 (1.35); 7.5096 (1.32); 7.3426 (0.4); 7.3387 (0.43); 7.3169 (2.14); 7.0772 (0.93); 6.9409 (1.97); 6.8046 (0.98); 4.0716 (2.52); 4.0652 (2.58); 4.0575 (2.56); 4.0511 (2.53); 3.9487 (0.67); 3.9434 (0.33); 3.9303 (16); 3.8703 (0.44); 2.9746 (1.16); 2.447 (1.02); 2.4407 (2.08); 2.4343 (1); 2.3048 (0.37); 2.2128 (9.87); 2.1323 (18.82); 2.1067 (0.36); 1.9713 (0.42); 1.9636 (3.45); 1.9575 (5.11); 1.9516 (24.66); 1.9454 (43.61); 1.9393 (57.68); 1.9331 (39.57); 1.9269 (20.25); 1.9203 (0.66); 1.7677 (0.33); 1.3717 (1.2); 1.2766 (1.39); 1.2701 (0.37); 0.0081 (0.76); −0.0002 (24.04); −0.0086 (0.72)

Compound No. C-63, solvent: [CD3CN],
10.0088 (0.79); 8.4929 (1.34); 8.4891 (1.36); 8.4812 (1.37); 8.4774 (1.34); 8.0678 (4.11); 8.0151 (1.36); 8.0114 (1.31); 7.9949 (1.47); 7.9911 (1.38); 7.6211 (1.69); 7.6167 (1.91); 7.5587 (1.76); 7.5429 (1.53); 7.5311 (1.47); 7.5227 (1.39); 7.5109 (1.34); 7.3127 (1.89); 7.0775 (1.28); 6.9412 (2.04); 6.8049 (1.02); 3.9422 (0.32); 3.9265 (16); 3.3462 (0.57); 3.3317 (0.76); 3.328 (1.82); 3.3137 (1.92); 3.3099 (1.99); 3.2956 (1.85); 3.292 (0.8); 3.2775 (0.59); 2.4691 (0.35); 2.4644 (0.5); 2.4597 (0.34); 2.2035 (10.27); 2.1607 (243.89); 2.1199 (0.56); 2.1136 (0.81); 2.1074 (1); 2.1013 (0.68); 2.0952 (0.39); 1.9643 (8.81); 1.9583 (13.26); 1.9524 (63.65); 1.9462 (113); 1.94 (149.85); 1.9339 (103.49); 1.9277 (53.17); 1.915 (0.83); 1.7808 (0.36); 1.7746 (0.66); 1.7685 (0.88); 1.7623 (0.6); 1.3716 (3.61); 1.2851 (0.42); 1.2766 (3.9); 1.1405 (3.69); 1.1224 (7.54); 1.1043 (3.6); 0.0079 (1.6); −0.0003 (44.62); −0.0086 (1.44)

Compound No. C-65, solvent: [CD3CN],
9.8751 (0.88); 8.4358 (1.47); 8.432 (1.39); 8.4241 (1.49); 8.4202 (1.36); 8.1525 (0.33); 8.095 (0.32); 8.058 (4.11); 7.9579 (1.49); 7.954 (1.37); 7.9377 (1.62); 7.9339 (1.41); 7.6076 (2.04); 7.6036 (2.07); 7.545 (2.02); 7.4499 (1.51); 7.4381 (1.47); 7.4297 (1.4); 7.4179 (1.32); 6.9924 (0.49); 6.986 (0.48); 6.4604 (2.48); 6.3995 (0.41); 4.867 (0.38); 4.8516 (0.95); 4.8363 (1.29); 4.8209 (0.96); 4.8056 (0.37); 3.9396 (0.79); 3.9319 (1.49); 3.9214 (16); 3.8736 (0.65); 3.6876 (1.22); 2.8256 (7.31); 2.8136 (7.28); 2.283 (0.44); 2.1961 (10.7); 2.171 (0.55); 2.1311 (46.09); 2.1128 (0.57); 2.1066 (0.64); 2.1004 (0.54); 2.0099 (0.82); 1.9634 (3.6); 1.9571 (5.24); 1.9515 (33.9); 1.9453 (62.53); 1.9392 (85.47); 1.933 (58.55); 1.9268 (29.67); 1.9066 (0.57); 1.7737 (0.36); 1.7676 (0.49); 1.7614 (0.33); 1.4052 (1.28); 1.3898 (1.49); 1.3738 (15.19); 1.3585 (15.05); 0.008 (0.64); −0.0002 (17.47); −0.0086 (0.63)

[b]The $^1$H NMR data are determined with a Bruker Avance 400 equipped with a flow probe head (volume 60 μl), with tetramethylsilane as a reference (0.0) and the solvents CD$_3$CN, CDCl$_3$, D$_6$-DMSO.

The NMR data for selected examples are listed either in conventional form (δ values, multiplet splitting, number of hydrogen atoms) or as NMR peak lists.

NMR peak list method:

When the $^1$H NMR data for selected examples are noted in the form of $^1$H NMR peak lists, first the δ-value in ppm and then the signal intensity in brackets were listed behind it for each signal peak. The δ value-signal intensity-number pairs for different signal peaks are listed with separation from one another by semicolons.

The peak list for one example therefore takes the form of:
δ$_1$ (intensity$_1$); δ$_2$ (intensity$_2$); . . . ; δ$_i$ (intensity$_i$); . . . ; δ$_n$ (intensity$_n$).

The solvent in which the NMR spectrum was recorded is listed in square brackets after the number of the example and before the NMR peak list or the conventional NMR interpretation list.

Use Examples

*Boophilus microplus*—Injection Test (BOOPMI Inj)

Solvent: dimethyl sulfoxide

To produce a suitable preparation of active compound, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

The activity is assessed after the desired time by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal: A-04, A-17, A-22, A-39, A-41, A-42, B-02, C-02, C-19, C-20, C-24, C-28, C-29, C-34, C-42, C-46

In this test, for example, the following compounds from the preparation examples show an efficacy of 95% at an application rate of 20 μg/animal: A-19, A-29

*Lucilia cuprina*-Test (LUCICU)

Solvent: dimethyl sulfoxide

To produce a suitable preparation of active compound, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After the desired time, the kill in % is determined. 100% means that all the larvae have been killed; 0% means that no larvae have been killed.

In this test, for example, the following compounds from the preparation examples show an efficacy of 100% at an application rate of 100 ppm: A-04, A-17, A-19, A-22, A-29, A-39, A-41, A-42, B-02, C-02, C-19, C-20, C-24, C-28, C-29, C-34, C-42, C-46

*Musca domestica*-Test (MUSCDO)

Solvent: dimethyl sulfoxide

To produce a suitable preparation of active compound, 10 mg of active compound are mixed with 0.5 ml of dimethyl sulfoxide, and the concentrate is diluted with water to the desired concentration.

Vessels containing a sponge treated with sugar solution and the active compound preparation of the desired concentration are populated with 10 adult houseflies (*Musca domestica*).

After the desired time, the kill in % is determined. 100% means that all of the flies have been killed; 0% means that none of the flies have been killed.

In this test, for example, the following compounds from the preparation examples show an efficacy of 100% at an application rate of 100 ppm: C-24

In this test, for example, the following compounds from the preparation examples show an efficacy of 90% at an application rate of 100 ppm: C-42

In this test, for example, the following compounds from the preparation examples show an efficacy of 80% at an application rate of 100 ppm: A-39, A-41, A-42, C-02, C-28

In this test, for example, the following compounds from the preparation examples show an efficacy of 100% at an application rate of 20 ppm: A-22, C-29

In this test, for example, the following compounds from the preparation examples show an efficacy of 80% at an application rate of 20 ppm: A-17, C-19

*Myzus persicae*—Spray Test (MYZUPE)

Solvent: 78 parts by weight of acetone 1.5 parts by weight of dimethylformamide

Emulsifier: 0.5 parts by weight of alkylaryl polyglycol ether

To produce a suitable active compound preparation, 1 part by weight of active compound is mixed with the stated amounts of solvent and emulsifier, and the concentrate is diluted with emulsifier-containing water to the desired concentration.

Disks of Chinese cabbage leaves (*Brassica pekinensis*) infested by all stages of the green peach aphid (*Myzus persicae*) are sprayed with an active compound preparation of the desired concentration.

After the desired period of time, the efficacy in % is determined. 100% means that all the aphids have been killed; 0% means that none of the aphids have been killed.

In this test, for example, the following compounds from the preparation examples show an efficacy of 100% at an application rate of 100 g/ha: A-04, A-05, A-08, A-11, A-22, A-23, A-33, A-36, A-37, A-42, A-43, A-45, A-48, B-02, B-03, B-09, B-10, B-11, C-02, C-04, C-05, C-09, C-10, C-11, C-16, C-21, C-22, C-23, C-24, C-25, C-26, C-29, C-34, C-39, C-41, C-44, C-45, C-46, C-47, C-48, C-60, C-63 In this test, for example, the following compounds from the preparation examples show an efficacy of 90% at an application rate of 100 g/ha: A-01, A-02, A-09, A-10, A-13, A-14, A-15, A-17, A-20, A-21, A-29, A-32, A-34, A-35, A-39, A-40, A-41, A-44, A-46, A-47, A-49, B-01, B-04, B-05, B-06, B-08, C-07, C-08, C-12, C-13, C-15, C-17, C-18, C-19, C-20, C-27, C-28, C-32, C-33, C-35, C-36, C-37, C-42, C-43, C-49, C-51, C-52, C-53, C-54, C-57, C-58, C-59, C-62

In this test, for example, the following compounds from the preparation examples show an efficacy of 90% at an application rate of 20 g/ha: C-56

*Phaedon cochleariae*—Spray Test (PHAECO)

Solvent: 78.0 parts by weight of acetone 1.5 parts by weight of dimethylformamide Emulsifier: 0.5 parts by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Disks of Chinese cabbage leaves (*Brassica pekinensis*) are sprayed with an active compound preparation of the desired concentration and, after drying, populated with larvae of the mustard beetle (*Phaedon cochleariae*).

After the desired period of time, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: A-01, A-02, A-03, A-04, A-06, A-08, A-17, A-18, A-19, A-20, A-21, A-22, A-23, A-25, A-31, A-32, A-33, A-34, A-35, A-38, A-39, A-41, A-42, A-43, A-44, A-45, A-46, A-47, A-48, A-49, B-01, B-02, B-03, B-05, B-06, B-10, B-11, B-12, C-01, C-02, C-03, C-04, C-05, C-06, C-07, C-08, C-09, C-10, C-11, C-12, C-13, C-15, C-16, C-17, C-22, C-23, C-24, C-25, C-26, C-27, C-28, C-29, C-30, C-31, C-32, C-33, C-34, C-35, C-36, C-37, C-42, C-43, C-44, C-45, C-47, C-48, C-49, C-51, C-53, C-56, C-57, C-58, C-59, C-60, C-62, C-63, C-64, C-65

In this test, for example, the following compounds from the preparation examples show an efficacy of 83% at an application rate of 100 g/ha: A-36, C-20, C-21

*Spodoptera frugiperda*—Spray Test (SPODFR)

Solvent: 78.0 parts by weight of acetone 1.5 parts by weight of dimethylformamide Emulsifier: 0.5 parts by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Leaf disks of maize (*Zea mays*) are sprayed with an active compound preparation of the desired concentration and, after drying, populated with caterpillars of the armyworm (*Spodoptera frugiperda*).

After the desired period of time, the efficacy in % is determined. 100% means that all the caterpillars have been killed; 0% means that no caterpillars have been killed.

In this test, for example, the following compounds from the preparation examples show an efficacy of 100% at an application rate of 100 g/ha: A-01, A-02, A-03, A-04, A-05, A-06, A-07, A-08, A-09, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, B-01, B-02, B-03, B-04, B-05, B-06, B-07, B-08, B-09, B-10, B-11, C-01, C-02, C-03, C-04, C-05, C-06, C-07, C-08, C-09, C-10, C-11, C-12, C-13, C-14, C-16, C-17, C-18, C-19, C-20, C-21, C-22, C-23, C-24, C-25, C-26, C-27, C-28, C-29, C-30, C-31, C-32, C-33, C-34, C-35, C-36, C-37, C-38, C-39, C-41, C-42, C-43, C-44, C-45, C-46, C-47, C-48, C-49, C-50, C-51, C-52, C-53, C-54, C-55, C-56, C-57, C-58, C-59, C-60, C-61, C-62, C-63, C-64, C-65

In this test, for example, the following compounds from the preparation examples show an efficacy of 83% at an application rate of 100 g/ha: C-15

*Tetranychus urticae*—Spray Test, OP-Resistant (TETRUR)

Solvent: 78.0 parts by weight of acetone 1.5 parts by weight of dimethylformamide Emulsifier: 0.5 parts by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Disks of bean leaves (*Phaseolus vulgaris*) infested with all stages of the greenhouse red spider mite (*Tetranychus urticae*) are sprayed with an active compound preparation of the desired concentration.

After the desired period of time, the efficacy in % is determined. 100% means that all the spider mites have been killed; 0% means that none of the spider mites have been killed.

In this test, for example, the following compounds from the preparation examples shows an efficacy of 100% at an application rate of 100 g/ha: A-22, A-43, A-46, B-01, C-42, C-45

In this test, for example, the following compounds from the preparation examples shows an efficacy of 90% at an application rate of 100 g/ha: A-01, A-02, A-17, A-19, A-26, A-29, B-02, C-41, C-43, C-44

The invention claimed is:
1. An anthranilic acid diamide derivative compound of formula (I)

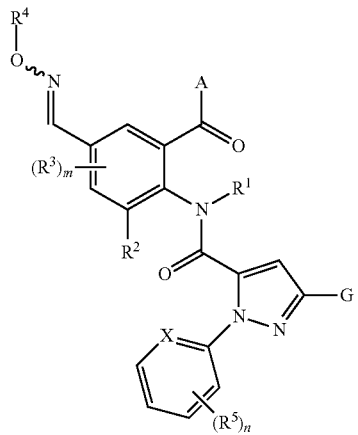

(I)

in which
if
A represents $N(R^6)R^7$,
G represents fluoromethyl, difluoromethyl, chlorodifluoromethyl, $C_2$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, fluoromethoxy, fluoroethoxy, difluoroethoxy, tetrafluoroethoxy, chlorodifluoroethoxy, dichlorofluoroethoxy, $C_3$-$C_6$-haloalkoxy, $C_1$-$C_6$-haloalkoxy-$C_1$-$C_4$-alkyl, $C_2$-$C_4$-haloalkylthio, $C_2$-$C_4$-haloalkylsulfinyl, $C_2$-$C_4$-haloalkylsulfonyl or represents —W-Q,
if
A represents)$N(R^8)$—$N(R^9)(R^{10})$,
G represents $C_1$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, $C_1$-$C_6$-haloalkoxy, $C_1$-$C_6$-haloalkoxy-$C_1$-$C_4$-alkyl, $C_1$-$C_4$-haloalkylthio, $C_1C_4$-haloalkylsulfinyl, $C_1$-$C_4$-haloalkylsulfonyl, halogen or represents —W-Q,
if
A represents $N(R^6)$-L,
G represents $C_1$-$C_6$-haloalkyl, $C_2$-$C_6$-haloalkenyl, $C_2$-$C_6$-haloalkynyl, $C_3$-$C_6$-halocycloalkyl, $C_1$-$C_6$-alkoxy, $C_1$-$C_6$-haloalkoxy, $C_1$-$C_6$-haloalkoxy-$C_1$-$C_4$-alkyl, $C_1$-$C_4$-haloalkylthio, $C_1$-$C_4$-haloalkylsulfinyl, $C_1$-$C_4$-haloalkylsulfonyl, halogen or represents —W-Q, $R^1$ represents hydrogen or represents $C_1$-$C_6$-alkyl, $C_2$-$C_6$-alkenyl, $C_2$-$C_6$-alkynyl or $C_3$-$C_6$-cycloalkyl, each of which is optionally mono- or polysubstituted by identical or different substituents, where the substituents may be selected independently of one another from the group consisting of halogen, cyano, nitro, hydroxy, $C_1$-$C_4$-alkoxy, $C_1$-$C_4$-alkylthio, $C_1$-$C_4$-alkylsulfinyl, $C_1$-$C_4$-alkylsulfonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl)-$C_3$-$C_6$-cycloalkylamino, $R^2$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, halogen, cyano, nitro or $C_3$-$C_6$-trialkylsilyl, $R^3$ independently of one another represent hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 2, $R^4$ represents $C_1$-$C_6$-alkyl, $C_3$-$C_6$-cycloalkyl, $C_2$-$C_6$-alkenyl, $C_2$-$C_6$-alkynyl, $C_1$-$C_6$-alkylsulfonyl, $C_1$-$C_4$-alkoxycarbonyl, $C_1$-$C_6$-alkylcarbonyl, aminocarbonyl, $C_1$-$C_6$-alkylaminocarbonyl or $C_1$-$C_6$-dialkylaminocarbonyl, each of which is optionally mono- or polysubstituted by identical or different substituents, where the substituents may be selected independently of one another from the group consisting of halogen, cyano, nitro, hydroxy, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, $C_1$-$C_4$-alkoxycarbonyl, $R^5$ independently of one another represent hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, n represents 0 to 4, X represents N, CH, CF, CCl, CBr or CI, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_2$-$C_6$-alkoxycarbonyl and $C_2$-$C_6$-alkylcarbonyl, $R^7$ represents hydrogen or represents $C_1$-$C_6$-alkyl, $C_2$-$C_6$-alkenyl, $C_2$-$C_6$-alkynyl, each of which is mono- or polysubstituted by identical or different substituents, where the substituents may be selected independently of one another from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl and $C_3$-$C_6$-trialkylsilyl, $R^7$ also furthermore represents optionally substituted aryl-$C_1$-$C_4$-alkyl, heteroaryl-$C_1$-$C_4$-alkyl, $C_3$-$C_{12}$-cycloalkyl, $C_3$-$C_{12}$-cycloalkyl-$C_1$-$C_6$-alkyl and $C_4$-$C_{12}$-bicycloalkyl, where the substituents may be selected independently of one another from the group consisting of halogen, cyano, nitro, hydroxy, amino, $C_1$-$C_6$-alkyl, $C_3$-$C_6$-cycloalkyl, $C_3$-$C_6$-cycloalkylamino, $C_1$-$C_4$- alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, $C_2$-$C_6$-alkylcarbonyl, $R^7$ furthermore represents a 5- or 6-membered aromatic or heteroaromatic ring, a 5- or 6-membered partially saturated ring or saturated heterocyclic ring, or a saturated or aromatic heterobicyclic ring which is mono- or polysubstituted by identical or different substituents and which may optionally contain one to three heteroatoms from the group consisting of O, S and N, where the substituents independently of one another may be selected from the group consisting of halogen, cyano, nitro, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl and $C_2$-$C_6$-alkylcarbonyl, $R^6$ and $R^7$ may be linked to one another via two to six carbon atoms and form a ring which optionally additionally contains a further nitrogen, sulfur or oxygen atom and may optionally be mono- to tetrasubstituted by $C_1$-$C_2$-alkyl, halogen, cyano, amino or $C_1$-$C_2$-alkoxy, $R^8$, $R^9$ independently of one another represent hydrogen, $C_2$-$C_6$-alkoxycarbonyl, $C_2$-$C_6$-alkylcarbonyl, $C_2$-$C_6$-alkylaminocarbonyl, $C_2$-$C_6$-dialkylaminocarbonyl, $C_2$-$C_6$-alkylsulfonyl, or represent $C_1$-$C_6$-alkyl, $C_1$-$C_6$-alkoxy, $C_2$-$C_6$-alkenyl, $C_3$-$C_6$-alkynyl, $C_3$-$C_6$-cycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, $C_2$-$C_6$-alkylcarbonyl and $C_3$-$C_6$-trialkylsilyl, or $R^8$, $R^9$ independently of one another represent a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or $R^8$ and $R^9$ may be linked to one another via two to six carbon atoms and form a ring which optionally additionally contains a further nitrogen, sulfur or oxygen atom and may optionally be mono- to tetrasubstituted by $C_1$-$C_2$-alkyl, $C_1$-$C_2$-haloalkyl, halogen, cyano, amino, $C_1$-$C_2$-alkoxy or $C_1$-$C_2$-haloalkoxy, $R^{10}$ represents a group selected from the group consisting of —C(=S)—$R^{11}$, —C(=O)—$R^{11}$, —C(=O)—OR$^{12}$, —C(=S)—OR$^{12}$, —C(=O)—SR$^{13}$, —C(=S)—SR$^{13}$, —C(=O)—NR$^{14}$R$^{15}$, —C(=S)—NR$^{14}$R$^{15}$, —S(O)$_2$—$R^{16}$ and —S(O)$_2$—NR$^{17}$R$^{18}$, $R^{11}$, $R^{12}$, $R^{13}$, $R^{16}$ independently of one another represent $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or aryl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^{14}$, $R^{15}$, $R^{17}$, $R^{18}$ independently of one another represent hydrogen or represent $R^{11}$, L represents

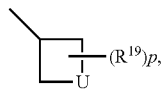

U represents O, S, SO, SO$_2$, S(O)=N—$R^{20}$, N—$R^{21}$, C=O, C=N—O—$R^{22}$, $R^{19}$ independently of one another represent hydrogen, $C_1$-$C_6$-alkyl, $C_1$-$C_6$-haloalkyl, $C_2$-$C_6$-alkenyl, $C_2$-$C_6$-alkynyl, halogen, cyano, nitro, hydroxy, COOH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl or $C_1$-$C_4$-haloalkylsulfonyl, $R^{20}$, $R^{21}$, $R^{22}$ independently of one another represent $C_1$-$C_6$-alkyl, P represents 0, 1, 2, 3, W represents a radical from the group consisting of —CH$_2$—, —CH$_2$O—, —OCH$_2$—, —CH$_2$OCH$_2$—, —CH$_2$S—, —CH$_2$SCH$_2$—, —CH(CN)—, —CH(F)—, —CH(Cl)—, —CH($C_1$-$C_6$-alkyl)-, —C(Di-$C_1$-$C_6$-alkyl)-, —CH$_2$CH$_2$—, Q represents a 5- or 6-membered aromatic heterocyclic ring from the group of Q-1 to Q-61 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro or $C_1$-$C_2$-haloalkoxy

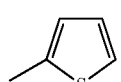

Q-1

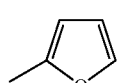

Q-2

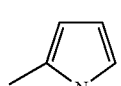

Q-3

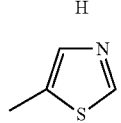

Q-4

Q-5 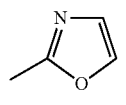
Q-6 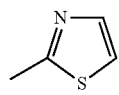
Q-7 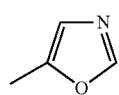
Q-8 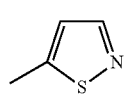
Q-9 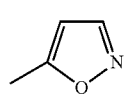
Q-10 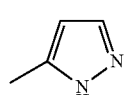
Q-11 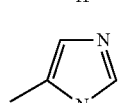
Q-12 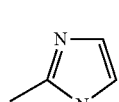
Q-13 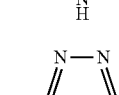
Q-14 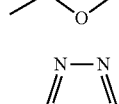
Q-15 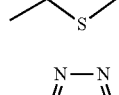
Q-16 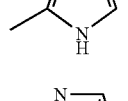
Q-17 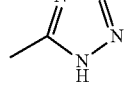
Q-18 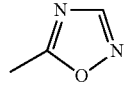
Q-19 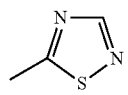
Q-20 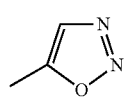
Q-21 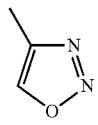
Q-22 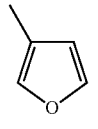
Q-23 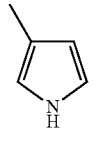
Q-24 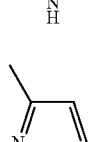
Q-25 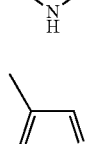
Q-26 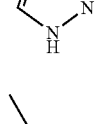
Q-27 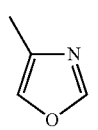
Q-28 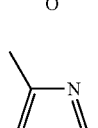
Q-29 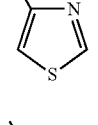
Q-30 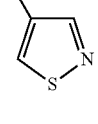

-continued
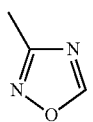
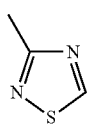
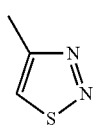
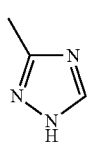
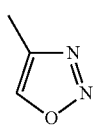
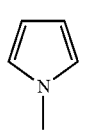
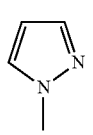
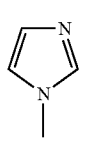
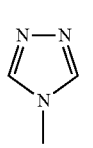
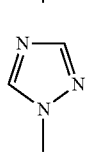
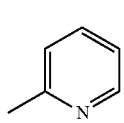
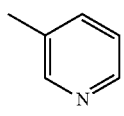
-continued
Q-31 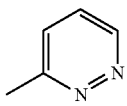
Q-32 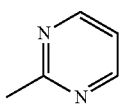
Q-33 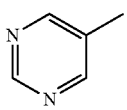
Q-34 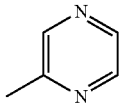
Q-35 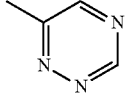
Q-36 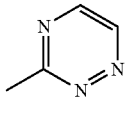
Q-37 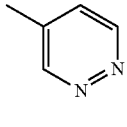
Q-38 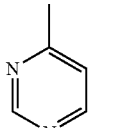
Q-39 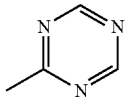
Q-40 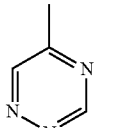
Q-41 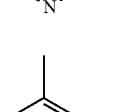
Q-42 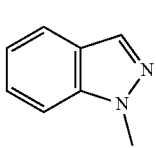
Q-43
Q-44
Q-45
Q-46
Q-47
Q-48
Q-49
Q-50
Q-51
Q-52
Q-53
Q-54

-continued

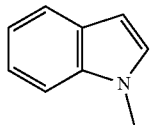
Q-55

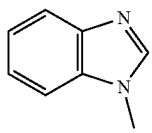
Q-56

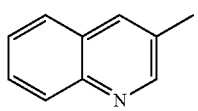
Q-57

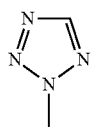
Q-58

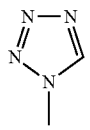
Q-59

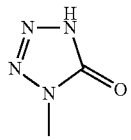
Q-60

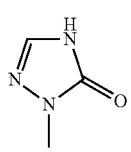
Q-61

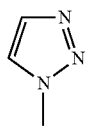
Q-62

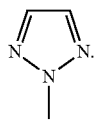
Q-63

2. The compound of formula (I) as claimed in claim 1, wherein

A represents $N(R^6)R^7$,

G represents fluoromethyl, difluoromethyl, chlorodifluoromethyl, $C_2$-$C_4$-haloalkyl, $C_2$-$C_4$-haloalkenyl, $C_2$-$C_4$-haloalkynyl, $C_3$-$C_4$-halocycloalkyl, $C_1$-$C_4$-alkoxy, fluoromethoxy, fluoroethoxy, difluoroethoxy, tetrafluoroethoxy, chlorodifluoroethoxy, dichlorofluoroethoxy, $C_3$-$C_4$-haloalkoxy, $C_1$-$C_4$-haloalkoxy-$C_1$-$C_4$-alkyl, $C_2$-$C_4$-haloalkylthio, $C_2$-$C_4$-haloalkylsulfinyl, $C_2$-$C_4$-haloalkylsulfonyl or represents —W-Q, $R^1$ represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl or $C_1$-$C_4$-alkylsulfonyl-$C_1$-$C_4$-alkyl, $R^2$ represents hydrogen, $C_1$-$C_4$-alkyl, halogen, cyano, $C_1$-$C_4$-alkoxy, $R^3$ represents hydrogen, $C_1$-$C_6$-alkyl, $C_1$-$C_4$-alkoxy, halogen, cyano or nitro, m represents 0 to 2, $R^4$ represents $C_1$-$C_4$-alkyl, $C_3$-$C_6$-cycloalkyl, $C_2$-$C_4$-alkenyl, $C_2$-$C_4$-alkynyl, $C_1$-$C_4$-alkylsulfonyl, $C_1$-$C_4$-alkoxycarbonyl, $C_1$-$C_4$-alkylcarbonyl, aminocarbonyl, $C_1$-$C_4$-alkylaminocarbonyl which is optionally mono- or polysubstituted by identical or different substituents, where the substituents independently of one another may be selected from the group consisting of halogen, cyano, $C_1$-$C_4$-alkyl, $C_1$-$C_4$-alkoxy, $C_1$-$C_4$-alkylthio, $C_1$-$C_4$-alkylsulfinyl or $C_1$-$C_4$-alkylsulfonyl, $R^5$ independently of one another represent hydrogen, halogen, cyano, $C_1$-$C_4$-alkyl, $C_1$-$C_4$-alkoxy, $C_1$-$C_4$-haloalkyl, $C_1$-$C_4$-haloalkoxy, n is 1, 2 or 3, X represents N, CH, CF or CCl, $R^6$ represents hydrogen or $C_1$-$C_6$-alkyl, $R^7$ represents hydrogen or represents $C_1$-$C_6$-alkyl, $C_2$-$C_6$-alkenyl, $C_3$-$C_6$-alkynyl which is optionally mono- or polysubstituted by identical or different substituents, where the substituents independently of one another may be selected from the group consisting of halogen, cyano, nitro, $C_1$-$C_6$-alkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_6$-alkoxycarbonyl, $C_1$-$C_6$-alkylcarbonyl, $R^7$ likewise furthermore represents optionally substituted phenylmethyl, pyridylmethyl, $C_3$-$C_6$-cycloalkyl, $C_3$-$C_6$-cycloalkyl-$C_1$-$C_4$-alkyl or $C_4$-$C_8$-bicycloalkyl, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^7$ likewise furthermore represents phenyl, pyridyl, pyrimidinyl, thiazolyl, oxazolyl, pyrazolyl, thienyl or furanyl which are optionally mono- or polysubstituted by identical or different substituents, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl or $C_1$-$C_4$-alkylsulfonyl, $C_2$-$C_6$-alkoxycarbonyl, $C_2$-$C_6$-alkylcarbonyl, W represents —$CH_2$—, —$CH_2O$—, —$OCH_2$—, —$CH_2OCH_2$—, —$CH_2S$—, —$CH_2SCH_2$—, —CH(CN)—, —CH($C_1$-$C_6$-alkyl)-, —C(di-$C_1$-$C_6$-alkyl)-, —$CH_2CH_2$—, Q represents a 5- or 6-membered aromatic heterocyclic ring from the group of Q-15, Q-16, Q-24, Q-25, Q-34, Q-37, Q-38, Q-39, Q-40, Q-41, Q-42, Q-58, Q-59 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro or $C_1$-$C_2$-haloalkoxy.

3. The compound of formula (I) as claimed in claim 1, wherein

A represents $N(R^8)$—$N(R^9)(R^{10})$,

G represents $C_1$-$C_4$-haloalkyl, $C_2$-$C_4$-haloalkenyl, $C_1$-$C_4$-alkoxy, $C_1$-$C_4$-haloalkoxy, $C_1$-$C_4$-haloalkoxy-$C_1$-$C_4$- alkyl, $C_1$-$C_4$-haloalkylthio, $C_1$-$C_4$-haloalkylsulfinyl, $C_1$-$C_4$-haloalkylsulfonyl, halogen or represents —W-Q, $R^1$ represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl or $C_1$-$C_4$-alkylsulfonyl-$C_1$-$C_4$-alkyl, $R^2$ represents hydrogen, $C_1$-$C_4$-alkyl, halogen, cyano, $C_1$-$C_4$-alkoxy, $R^3$ represents hydrogen, $C_1$-$C_6$-alkyl, $C_1$-$C_4$-alkoxy, halogen, cyano or nitro, m represents 0 to 2, $R^4$ represents $C_1$-$C_4$-alkyl, $C_3$-$C_6$-cycloalkyl, $C_2$-$C_4$-alkenyl, $C_2$-$C_4$-alkynyl, $C_1$-$C_4$-alkylsulfonyl, $C_1$-$C_4$-alkoxycarbonyl, $C_1$-$C_4$-alkylcarbonyl, aminocarbonyl, $C_1$-$C_4$-alkylaminocarbonyl which is optionally mono- or polysubstituted by identical or different substituents, where the substituents independently of one another may be selected from the group consisting of halogen, cyano, $C_1$-$C_4$-alkyl, $C_1$-$C_4$-alkoxy, $C_1$-$C_4$-alkylthio, $C_1$-$C_4$-alkylsulfinyl or $C_1$-$C_4$-alkylsulfonyl, $R^5$ independently of one another represent hydrogen, halogen, cyano, $C_1$-$C_4$-alkyl, $C_1$-$C_4$-alkoxy, $C_1$-$C_4$-haloalkyl, $C_1$-$C_4$-haloalkoxy, n is 1, 2 or 3, X represents N, CH, CF or CCl, $R^6$ represents hydrogen or $C_1$-$C_6$-alkyl, $R^7$ represents hydrogen or represents $C_1$-$C_6$-alkyl, $C_2$-$C_6$-alkenyl, $C_3$-$C_6$-alkynyl, each of which is optionally mono- or polysubstituted by identical or different substituents, where the substituents independently of one another may be selected from the group consisting of halogen, cyano, nitro, $C_1$-$C_6$-alkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_6$-alkoxycarbonyl, $C_1$-$C_6$-alkylcarbonyl, $R^7$ likewise furthermore represents optionally substituted phenylmethyl, pyridylmethyl, $C_3$-$C_6$-cycloalkyl, $C_3$-$C_6$-cycloalkyl-$C_1$-$C_4$-alkyl or $C_4$-$C_8$-bicycloalkyl, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^7$ likewise furthermore represents phenyl, pyridyl, pyrimidinyl, thiazolyl, oxazolyl, pyrazolyl, thienyl or furanyl which are optionally mono- or polysubstituted by identical or different substituents, where the substituents independently of one another may be selected from the group consisting of halogen, cyano, nitro, hydroxy, amino, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl or $C_1$-$C_4$-alkylsulfonyl, $C_2$-$C_6$-alkoxycarbonyl, $C_2$-$C_6$-alkylcarbonyl, $R^8$, $R^9$ independently of one another represent hydrogen or represent $C_1$-$C_4$-alkyl, $C_2$-$C_4$-alkenyl, $C_3$-$C_4$-alkynyl, $C_3$-$C_4$-cycloalkyl, $C_2$-$C_4$-alkylcarbonyl or $C_2$-$C_4$-alkylsulfonyl each of which is optionally mono- or polysubstituted by identical or different substituents, where the substituents independently of one another may be selected from the group consisting of halogen, cyano, nitro, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_4$-alkoxycarbonyl and $C_2$-$C_4$-alkylcarbonyl, $R^{10}$ represents a group selected from the group consisting of —C(=O)—$R^{11}$, —C(=O)—$OR^{12}$, —C(=O)—$NR^{14}R^{15}$, —S(O)$_2$—$R^{16}$, $R^{11}$, $R^{12}$, $R^{16}$, independently of one another represent $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl or aryl, each of which is optionally mono- or polysubstituted by identical or different substituents, where the substituents independently of one another may be selected from the group consisting of halogen, cyano, nitro, hydroxy, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_2$-$C_6$-alkoxycarbonyl, $C_2$-$C_6$-alkylcarbonyl, $R^{14}$, $R^{15}$ independently of one another represent hydrogen or represent $R^{11}$, W represents —$CH_2$—, —$CH_2O$—, —$OCH_2$—, —$CH_2OCH_2$—, —$CH_2S$—, —$CH_2SCH_2$—, —CH(CN)—, —CH($C_1$-$C_6$-alkyl)-, —C(di-$C_1$-$C_6$-alkyl)-, —$CH_2CH_2$—, Q represents a 5- or 6-membered aromatic heterocyclic ring from the group of Q-15, Q-16, Q-24, Q-25, Q-34, Q-37, Q-38, Q-39, Q-40, Q-41, Q-42, Q-58, Q-59 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro and $C_1$-$C_2$-haloalkoxy.

4. The compound of formula (I) as claimed in claim 1, wherein

A represents N($R^6$)-L,

G represents $C_1$-$C_4$-haloalkyl, $C_2$-$C_4$-haloalkenyl, $C_1$-$C_4$-alkoxy, $C_1$-$C_4$-haloalkoxy, $C_1$-$C_4$-haloalkoxy-$C_1$-$C_4$-alkyl, $C_1$-$C_4$-haloalkylthio, $C_1$-$C_4$-haloalkylsulfinyl, $C_1$-$C_4$-haloalkylsulfonyl, halogen or represents —W-Q, $R^1$ represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl or $C_1$-$C_4$-alkylsulfonyl-$C_1$-$C_4$-alkyl, $R^2$ represents hydrogen, $C_1$-$C_4$-alkyl, halogen, cyano, $C_1$-$C_4$-alkoxy, $R^3$ represents hydrogen, $C_1$-$C_6$-alkyl, $C_1$-$C_4$-alkoxy, halogen, cyano or nitro, m represents 0 to 2, $R^4$ represents $C_1$-$C_4$-alkyl, $C_3$-$C_6$-cycloalkyl, $C_2$-$C_4$-alkenyl, $C_2$-$C_4$-alkynyl, $C_1$-$C_4$-alkylsulfonyl, $C_1$-$C_4$-alkoxycarbonyl, $C_1$-$C_4$-alkylcarbonyl, aminocarbonyl, $C_1$-$C_4$-alkylaminocarbonyl, each of which is optionally mono- or polysubstituted by identical or different substituents, where the substituents independently of one another may be selected from the group consisting of halogen, cyano, $C_1$-$C_4$-alkyl, $C_1$-$C_4$-alkoxy, $C_1$-$C_4$-alkylthio, $C_1$-$C_4$-alkylsulfinyl and $C_1$-$C_4$-alkylsulfonyl, $R^5$ independently of one another represent hydrogen, halogen, cyano, $C_1$-$C_4$-alkyl, $C_1$-$C_4$-alkoxy, $C_1$-$C_4$-haloalkyl, $C_1$-$C_4$-haloalkoxy, n is 1, 2 or 3, X represents N, CH, CF or CCl, $R^6$ represents hydrogen or $C_1$-$C_6$-alkyl, W represents —$CH_2$—, —$CH_2O$—, —$OCH_2$—, —$CH_2OCH_2$—, —$CH_2S$—, —$CH_2SCH_2$—, —CH(CN)—, —CH($C_1$-$C_6$-alkyl)-, —C(di-$C_1$-$C_6$-alkyl)-, —$CH_2CH_2$—, Q represents a 5- or 6-membered aromatic heterocyclic ring from the group of Q-15, Q-16, Q-24, Q-25, Q-34, Q-37, Q-38, Q-39, Q-40, Q-41, Q-42, Q-58, Q-59 which is optionally mono- or polysubstituted, where the substituents independently of one another may be selected from the group consisting of $C_1$-$C_3$-alkyl, $C_1$-$C_3$-haloalkyl, $C_1$-$C_2$-alkoxy, halogen, cyano, hydroxy, nitro or $C_1$-$C_2$-haloalkoxy.

L represents

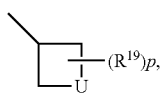

U represents O, S, SO or $SO_2$, $R^{19}$ represents hydrogen or $C_1$-$C_4$-alkyl, P represents 0, 1, 2.

5. The compound of formula (I) as claimed in claim 1, wherein

W represents $OCH_2$,

Q represents Q-42.

6. The compound of formula (I) as claimed in claim 1, wherein

W represents $CH_2$,

Q represents Q-58.

7. A process for preparing a compound of formula (I) as claimed in claim 1, comprising (A) for the synthesis of anthranilamides of formula (I) in which $R^1$ represents hydrogen, reacting a benzoxazinone of formula (II)

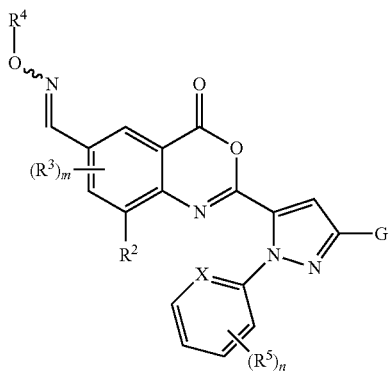

in which $R^2$, $R^3$, $R^4$, $R^5$, G, X, m and n have the meanings given above with a compound of formula (III)

A-H     (III)

in which A has the meanings given above
in the presence of a diluent,
or (B) reacting an aniline of formula (IV)

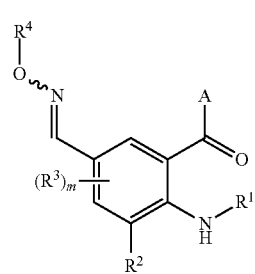

in which A, $R^1$, $R^2$, $R^3$, $R^4$ and m have the meanings given above with carbonyl chloride of formula (V)

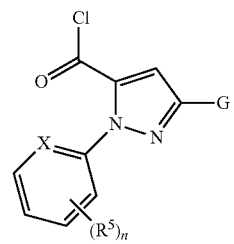

in which $R^5$, G, X and n have the meanings given above, in the presence of an acid binder, or (C) reacting an aniline of formula (IV)

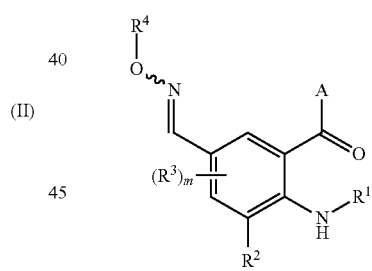

in which A, $R^1$, $R^2$, $R^3$, $R^4$ and m have the meanings given above with a carboxylic acid of formula (VI)

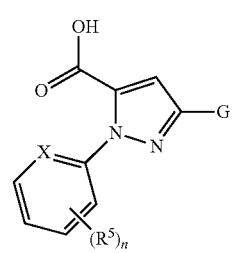

in which $R^5$, G, X and n have the meanings given above, in the presence of a condensing agent, or (D) for the synthesis of anthranilamides of formula (I) in which A represents $N(R^8)$—$N(R^9)(R^{10})$, reacting an anthranilic acid hydrazide of formula (VII)

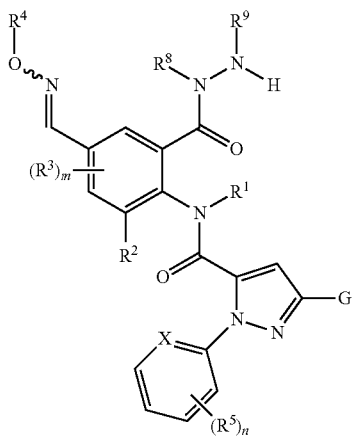
(VII)

in which $R^1$, $R^2$, $R^3$, $R^4$, $R^5$, $R^8$, $R^9$, G, X, m and n have the meanings given above, with a unit Y—$R^{10}$, where $R^{10}$ has the meaning given above and Y represents a suitable leaving group.

8. An agrochemical composition comprising at least one compound of formula (I) as claimed in claim 1 and one or more extenders and/or surfactants.

9. A process for preparing an agrochemical composition, comprising mixing at least one compound of formula (I) as claimed in claim 1 with one or more extenders and/or surfactants.

10. A compound of formula (I) as claimed in claim 1 capable of being used for controlling one or more animal pests.

11. A method for controlling one or more animal pests, comprising allowing a compound of formula (I) as claimed in claim 1 to act on one or more animal pests and/or a habitat thereof and/or seed.

\* \* \* \* \*